US007368285B2

(12) United States Patent
Zoller et al.

(10) Patent No.: US 7,368,285 B2
(45) Date of Patent: May 6, 2008

(54) HETEROMERIC UMAMI T1R1/T1R3 TASTE RECEPTORS AND ISOLATED CELLS THAT EXPRESS SAME

(75) Inventors: Mark Zoller, San Diego, CA (US); Xiaodong Li, San Diego, CA (US); Lena Staszewski, San Diego, CA (US); Shawn O'Connell, Encinitas, CA (US); Sergey Zozulya, San Diego, CA (US); Jon Elliot Adler, San Diego, CA (US); Hong Xu, San Diego, CA (US); Fernando Echeverri, Chula Vista, CA (US)

(73) Assignee: Senomyx, Inc., San Diego, CA (US)

(*) Notice: Subject to any disclaimer, the term of this patent is extended or adjusted under 35 U.S.C. 154(b) by 804 days.

(21) Appl. No.: 10/179,373

(22) Filed: Jun. 26, 2002
(Under 37 CFR 1.47)

(65) Prior Publication Data

US 2003/0232407 A1 Dec. 18, 2003
US 2008/0020424 A9 Jan. 24, 2008

Related U.S. Application Data

(63) Continuation-in-part of application No. 10/035,045, filed on Jan. 3, 2002, now Pat. No. 7,241,880, and a continuation-in-part of application No. 09/897,427, filed on Jul. 3, 2001, now Pat. No. 6,955,887, and a continuation-in-part of application No. 09/799,629, filed on Jul. 3, 2001.

(60) Provisional application No. 60/300,434, filed on Jun. 26, 2001, provisional application No. 60/304,749, filed on Jul. 13, 2001, provisional application No. 60/310,493, filed on Aug. 8, 2001, provisional application No. 60/331,771, filed on Nov. 21, 2001, provisional application No. 60/339,472, filed on Dec. 14, 2001, provisional application No. 60/372,090, filed on Apr. 15, 2002, provisional application No. 60/374,143, filed on Apr. 22, 2002.

(51) Int. Cl.

| | |
|---|---|
| *C12N 5/00* | (2006.01) |
| *C12N 5/02* | (2006.01) |
| *C12N 5/06* | (2006.01) |
| *C12N 5/10* | (2006.01) |
| *C12N 5/08* | (2006.01) |

(52) U.S. Cl. ...................... 435/325; 435/358; 435/361; 435/363; 435/364; 435/365; 435/366; 435/367

(58) Field of Classification Search ................ 530/350, 530/300, 402
See application file for complete search history.

(56) References Cited

U.S. PATENT DOCUMENTS

| | | | |
|---|---|---|---|
| 5,993,778 A | 11/1999 | Firestein et al. | |
| 6,383,778 B1 | 5/2002 | Zuker et al. | |
| 6,540,978 B1 | 4/2003 | Margolskee et al. | |
| 2002/0051997 A1 | 5/2002 | Zuker et al. | |
| 2002/0094551 A1 | 7/2002 | Adler et al. | |
| 2002/0151052 A1 | 10/2002 | Chaudhari et al. | |
| 2002/0160424 A1 | 10/2002 | Adler et al. | |
| 2002/0168635 A1 | 11/2002 | Zuker et al. | |
| 2003/0008344 A1 | 1/2003 | Adler et al. | |
| 2003/0022278 A1 | 1/2003 | Zuker et al. | |
| 2003/0022288 A1 | 1/2003 | Zuker et al. | |
| 2003/0036089 A1 | 2/2003 | Wei et al. | |
| 2003/0040045 A1 | 2/2003 | Zuker et al. | |
| 2003/0054448 A1 | 3/2003 | Adler et al. | |
| 2003/0166137 A1* | 9/2003 | Zuker et al. | 435/69.1 |
| 2004/0086877 A1* | 5/2004 | Lal et al. | 435/6 |
| 2005/0106571 A1 | 5/2005 | Erlenbach et al. | |
| 2007/0105159 A1 | 5/2007 | Erlenbach et al. | |

FOREIGN PATENT DOCUMENTS

| | | |
|---|---|---|
| WO | WO 00/06592 | 2/2000 |
| WO | WO 00/06593 | 2/2000 |
| WO | WO 00/06593 A | 2/2000 |
| WO | WO 01/64882 | 9/2001 |
| WO | WO 01/66563 A2 | 9/2001 |

(Continued)

OTHER PUBLICATIONS

Kinnamon SC et al. Annual Review of Physiol. 54:715-731, 1992.*

(Continued)

*Primary Examiner*—Robert S. Landsman
(74) *Attorney, Agent, or Firm*—Hunton & Williams LLP

(57) ABSTRACT

The present invention relates to the discovery that the T1R receptors assemble to form functional taste receptors. Particularly, it has been discovered that co-expression of T1R1 and T1R3 results in a taste receptor that responds to umami taste stimuli, including monosodium glutamate. Also, it has been discovered that co-expression of the T1R2 and T1R3 receptors results in a taste receptor that responds to sweet taste stimuli including naturally occurring and artificial sweeteners.

Also the present invention relates to the use of hetero-oligomeric taste receptors comprising T1R1/T1R3 and T1R2/T1R3 in assays to identify compounds that respectively respond to umami taste stimuli and sweet taste stimuli.

Further, the invention relates to the constitutive of cell lines that stably or transiently co-express a combination of T1R1 and T1R3; or T1R2 and T1R3; under constitutive or inducible conditions. The use of these cells lines in cell-based assays to identify umami and sweet taste modulatory compounds is also provided, particularly high throughput screening assays that detect receptor activity by use of fluorometric imaging.

Finally, the invention relates to the discovery that some compounds, e.g., lactisole, inhibit both the activities of human T1R2/T1R3 and T1R1/T1R3 receptors, and accordingly the sweet and umami taste, suggesting that these receptors may be the only sweet and umami receptors.

33 Claims, 16 Drawing Sheets

FOREIGN PATENT DOCUMENTS

| | | | |
|---|---|---|---|
| WO | WO 01/83749 | | 11/2001 |
| WO | WO 03/025137 | | 3/2002 |
| WO | WO 02/064631 | A2 | 8/2002 |
| WO | WO 02/064631 | A3 | 8/2002 |
| WO | WO 03/001876 | A2 | 1/2003 |
| WO | WO 2005/015158 | A2 | 2/2005 |

OTHER PUBLICATIONS

Montmayeur, J-P., et al., "A Candidate Taste Receptor Gene Near a Sweet Taste Locus," Nature Neuroscience, May 2001, pp. 492-498, vol. 4, No. 5, Nature America, Inc., US.

Kitagawa M., et al., "Molecular Genetic Identification of a Candidate Receptor Gene for Sweet Taste," Biochemical and Biophysical Research Communications, Apr. 27, 2001, pp. 236-242, vol. 283, No. 1, Academic Press, San Diego, California, US.

Max Marianna, et al., "Tas1r3, Encoding a New Candidate Taste Receptor, is Allelic to the Sweet Responsiveness Locus Sac," Nature Genetics, May 2001, pp. 58-63, vol. 28, No. 1, Nature America, New York, US.

Sainz E., et al., "Identification of a Novel Member of the T1R Family of Putative Taste Receptors," Journal of Neurochemistry, May 2001, pp. 896-903, vol. 77, No. 3, New York, NY, US.

Johnson C., et al., "The Effect of the Sweetness Inhibitor 2(-4-methoxyphenoxy) Propanoic Acid (Sodium Salt) (Na-PMP) on the Taste of Bitter-sweet Stimuli," Chemical Sense, Aug. 1994, pp. 349-358, vol. 19, No. 4. Oxford, UK.

Xiadong Li, et al., "Human Receptors for Sweet and umami taste", Proceeding of the National Academy of Science, vol. 99, No. 7, p. 4692-4696, Apr. 2, 2002.

Database EMBL 'Online!, embl heidelberg; Acc#: Ac062024, Jun. 21, 2000.

E. Adler, et al., "A Novel Family of Mammalian Taste Receptors", Cell, vol. 100, No. 6, p. 693-702, Mar. 17, 2000.

Guo, et al., "Protein Tolerance to Random Amino Acid change", PNAS, vol. 101, No. 25, p. 9205-9210, Jun. 22, 2004.

Nelson, et al., "Mammalian Sweet Taste Receptors", Cell, vol. 106, p. 381-390, Aug. 10, 2001.

Nelson,et al., "An Amino-acid Taste Receptor", Nature, vol. 416, p. 199-202, Mar. 14, 2002.

Alexander, et al., "Altering the Antigenicity of proteins", Proc. Natl. Acad. Sci. USA, vol. 89, p. 3352-3356, Apr. 1992.

Bowie, et al., "Deciphering the Message in Protein Sequences: Tolerance to Amino Acid Substitutions", Science, vol. 247, p. 13061310, Mar. 16, 1990.

Krautwurst, et al., "Identification of Ligands for Olfactory Receptors by Functional Expression of a Receptor Library", Cell, vol. 95, p. 917-926, Dec. 23, 1998.

GenBank Accession No. AL139287, clone RP5-89003, Feb. 13, 2000.

GenBank Accession No. AA907022, May 19, 1998.

Hoon, et al., "Putative Mammalian Taste Receptors: A Class of Taste-Specific GPCRs with Distinct Topographic Selectivity", Cell, vol. 96, p. 541-551, Feb. 19, 1999.

Lindemann, "A Taste for Umami", Nature Neuroscience, ol. 3, No. 2, p. 99-100, Feb. 2000.

Perruccio, et al., "Possible Role for gustducin in Taste Transduction in Hirudo Medicinalis", Society for Neuroscience Abstracts, vol. 26, No. 1-2, Abstract No. 66.15, 2000.

Wolfgang Bönigk, et al., "The Native Rat Olfactory Cyclic Nucleotide-Gated Channel is Composed of Three Distinct Subunits", The Journal of Neuroscience, vol. 19, No. 136, p. 5332-5347, Jul. 1, 1999.

Sue C. Kinnamon and Thomas A. Cummings, "Chemosensory Transduction Mechanisms in Taste", Annu. Rev. Physoil., vol. 54, p. 715-731, 1992.

* cited by examiner

```
hT1R1 1    -MLLCTARLVGLQLLISCCWAFACHSTES------SHDFTLPGDYLLAGLFPL-HSGCLQVRHR--PEVTLCDRSCSFNEHGYHLFQAMRLGVEEINNSTALLPNITLGYQLYDVCSD-SANVYATLRVL 119
rT1R1 1    MLFWAAHLLLSLQL--VYCWAFSCQRTES------SPGFSLPGDFLLAGLFSL-HGDCLQVRHR--PLVTSCDRPDSFNGHGYHLFQAMRFTVEEINNSSALLPNITLGYELYDVCSE-SANVYATLRVL 118
hT1R2 1    -MGPRAKTICSLFF---LLWVLAEP--AE------NSDFYLPGDYLLGGLFSL-HANMKGIVHLNFLQVPMCK-EYEVKVIGYNLMQAMRFAVEEINNDSSLLPGVLLGYEIVDVCYI-SNNVQPVLYFL 115
rT1R2 1    -MGPQARTLCLLSL---LLHVLPKPGKLVE------NSDFHLAGDYLLGGLFTL-HANVKSISHLSYLQVPKCN-EFTMKVLGYNLMQAMRFAVEEINNCSSLLPGVLLGYEMVDVCYL-SNNIHPGLYFL 118
hT1R3 1    ---MLGPAVLGLSLWALLHPGTGAPLCLS-------QQLRMKGDYVLGGLFPLGEAEEAGLRSRTRPSSPVCT---RFSSNGLLWALAMKMAVEEINNKSDLLPGLRLGYDLFDTCSEPVVAMKPSLMFL 117
rT1R3 1    ---MPGLAILGLSLAAFLELGMGSSLCLS-------QQFKAQGDYILGGLFPLGTTEEATLNQRTQPNGILCT---RFSPLGLFLAMAMKMAVEEINNGSALLPGLRLGYDLFDTCSEPVVTMKPSLMFM 117
mGluR1 1   MVRLLLIFFPMIFLEMSILPRMPDRKVLLAGASSQRSVARMDGDVIIGALFSVHHQPPAEKVPE-----RKCG--EIREQYGIQRVEAMFHTLDKINADPVLLPNITLGSEIRDSCWHSSVALEQSIEFI 123

hT1R1 120  SLPG-------QHHIELQGDLLHYSP-----TVLAVIGPDSTNRAATTAALLSPFLVPMISYAASSETLSVKRQYPSFLRTIPNDKYQVETMVLLLQKFGWTWISLVGSSDDYGQLGVQALENQATGQ-G 236
rT1R1 119  ALQG-------PRHIEIQKDLRNHSS-----KVVAFIGPDNTDHAVTTAALLGPFLMPLVSYEASSVVLSAKRKFPSFLRTVPSDRHQVEVMVQLLQSFGWVWISLIGSYGDYGQLGVQALEELAVPR-G 235
hT1R2 116  AHE--------DNLLPIQEDYSNYIS-----RVVAVIGPDNSESVMTVANFLSLFLLPQITYSAISDELRDKVRFPALLRTTPSADHHVEAMVQLMLHFRWNWIIVLVSSDTYGRDNGQLLGERVARR-D 231
rT1R2 119  AQD--------DDLLPILKDYSQYMP-----HVVAVIGPDNSESAITVSNILSHFLIPQITYSAISDKLRDKRHFPSMLRTVPSATHHIEAMVQLMVHFQWNWIVVLVSDDDYGRENSHLLSQRLTKTSD 235
hT1R3 118  AKAG-------SRDIAAYCNYTQYQP-----RVLAVIGPHSSELAMVTGKFFSFFLMPQVSYGASMELLSARETFPSFFRTVPSDRVQLTAAAELLQEFGWNWVAALGSDDEYGRQGLSIFSALAAAR-G 234
rT1R3 118  AKVG-------SQSIAAYCNYTQYQP-----RVLAVIGPHSSELALITGKFFSFFLMPQVSYSASMDRLSDRETFPSFFRTVPSDRVQLQAVVTLLQNFSWNWVAALGSDDDYGREGLSIFSGLANSR-G 234
mGluR1 124 RDSLISIRDEKDGINRCLPDGQTLPPGRTKKPIAGVIGPGSSSVAIQVQNLLQLFDIPQIAYSATSIDLSDKTLYKYFLRVVPSDTLQARAMLDIVKRYNWTYVSAVHTEGNYGESGMDAFKELAAQE-G 252

hT1R1 237  ICIAFKDIMPFSAQVG----DER--MQCLMRHLAQ--AGATVVVVFSSRQLARVFFESVVLTNLTGKVWVA-SEAWALSRHITGVPGIQRIGMVLGVAIQKRAVPGLKAFEEAYAR---ADKKAPRPCHK 354
rT1R1 236  ICVAFKDIVPFSARVG----DER--MQSMMQHLAQ--ARTTVVVVFSNRHLARVFFRSVVLANLTGKVWVA-SEDWAISTYITSVTGIQGIGTVLGVAVQQRQVPGLKEFEESYVR---AVTAAPSACPE 353
hT1R2 232  ICIAFQETLPTLQPNQNMTSEERQRLVTIVDKLQQ--STARVVVVFSPDLTLYHFFNEVLRQNFTGAVWIA-SESWAIDPVLHNLTELGHLGTFLGITIQSVPIPGFSEFREWGPQ---AGPPPLSRTSQ 355
rT1R2 236  ICIAFQEVLPIPESSQVMRSEEQRQLDNILDKLRR--TSARVVVVFSPELSLYSFFHEVLRWNFTGFVWIA-SESWAIDPVLHNLTELRHTGTFLGVTIQRVSIPGFSQFRVRRDK---PGYPVPNTTNL 359
hT1R3 235  ICIAHEGLVPLPRADD----SRLGKVQDVLHQVNQ--SSVQVVLLFASVHAAHALFNYSISSRLSPKVWVA-SEAWLTSDLVMGLPGMAQMGTVLGFLQRGAQLHEFPQYVKTHLA--LATDPAFCSALG 355
rT1R3 235  ICIAHEGLVPQHDTSG----QQLGKVVDVLRQVNQ--SKVQVVVLFASARAVYSLFSYSILHDLSPKVWVA-SESWLTSDLVMTLPNIARVGTVLGFLQRGALLPEFSHYVETRLA--LAADPTFCASLK 355
mGluR1 253 LCIAHSDKIYSNAGEK--------SFDRLLRKLRERLPKARVVVCFCEGMTVRGLLSAMRRLGVVGEFSLIGSDGWADRDEVIEGYEVEANGGIT-IKLQSPEVRSFDDYFLKLRLDTNTRNPWFPEFWQ 373

hT1R1 355  G-----SWCSSNQLCRECQAFMAHTMPKLKAFS------MSSAYNAYRAVYAVAHGLHQLLGCA----SGACSR-GRVYPWQLLEQIHKVHFL-LHKDTVAFNDNRDPLSSYNIIAWDWNGPKW-TFTVL 466
rT1R1 354  G-----SWCSTNQLCRECHTFTTRNMPTLGAFS------MSAAYRVYEAVYAVAHGLHQLLGCT----SEICSR-GPVYPWQLLQQIYKVNFL-LHENTVAFDDNGDTLGYYDIIAWDWNGPEW-TFEII 465
hT1R2 356  S-----YTC--NQECDNCLNATLSFNTILRLSG------ERVVYSVYSAVYAVAHALHSLLGCD----KSTCTK-RVVYPWQLLEEIWKVNFT-LLDHQIFFDPQGDVALHLEIVQWQWDRSQN-PFQSV 465
rT1R2 360  R-----TTC--NQDCDACLNTTKSFNNILILSG------ERVVYSVYSAVYAVAHALHRLLGCN----RVRCTK-QKVYPWQLLREIWHVNFT-LLGNRLFFDQQGDMPMLLDIIQWQWDLSQN-PFQSI 469
hT1R3 356  EREQGLEEDVVGQRCPQCDCITLQNVSAGLN--------HHQTFSVYAAVYSVAQALHNTLQCN----ASGCPAQDPVKPWQLLENMYNLTFH-VGGLPLRFDSSGNVDMEYDLKLWVWQGSVP-RLHDV 471
rT1R3 355  -AELDLEERVMGPRCSQCDYIMLQNLSSGLMQNLSAGQLHHQIFATYAAVYSVAQALHNTLQCN----VSHCHTSEPVQPWQLLENMYNMSFR-ARDLTLQFDAKGSVDMEYDLKMWVWQSPTP-VLHTV 478
mGluR1 374 HR----FQCRLPGHLLENPNFKKVCTGNESLEENYVQ--DSKMGFVINAIYAMAHGLQNMHHALCPGHVGLCDAMKPIDGRKLLDFLIKSSFVGVSGEEVWFDEKGDAPGRYDIMNLQYTEANRYDYVHV 497
```

FROM FIG. 1A

```
hT1R1  467 GSSTWSPVQLNINETKIQWHGKDNQVPKSVCSSDCLEGHQR-VVTGFHHCCFECVPCGAGTFLN-KSDLYRCQPCGKEEWAPEGSQTCFPRTVVFLALREHTSWVLLAANTLLLLLLLGTAGLFAWHLDT   594
rT1R1  466 GSASLSPVHLDINKTKIQWHGKNNQVPVSVCTTDCLAGHHR-VVVGSHHCCFECVPCEAGTFLN-MSELHICQPCGTEEWAPKESTTCFPRTVEFLAWHEPISLVLIAANTLLLLLLVGTAGLFAWHFHT   593
hT1R2  466 ASYYPLQRQLKN-IQDISWHTVNNTIPMSMCSKRCQSGQKK-KPVGIHVCCFECIDCLPGTFLNHTEDEYECQACPNNEWSYQSETSCFKRQLVFLEWHEAPTIAVALLAALGFLSTLAILVIFWRHFQT   593
rT1R2  470 ASYSPTSKRLTY-INNVSWYTPNNTVPVSMCSKSCQPGQMK-KSVGLHPCCFECLDCMPGTYLNRSADEFNCLSCPGSMWSYKNDITCFQRRPTFLEWHEVPTIVVAILAALGFFSTLAILFIFWRHFQT   597
hT1R3  472 GRFN-GSLRTER--LKIRWHTSDNQKPVSRCSRQCQEGQVR-RVKGFHSCCYDCVDCEAGSYRQ-NPDDIACTFCGQDEWSPERSTRCFRRRSRFLAWGEPAVLLLLLLLSLALGLVLAALGLFVHHRDS   596
rT1R3  479 GTFN-GTLQLQH--SKMYWPG--NQVPVSQCSRQCKDGQVR-RVKGFHSCCYDCVDCKAGSYRK-HPDDFTCTPCGKDQWSPEKSTTCLPRRPKFLAWGEPAVLSLLLLLCLVLGLTLAALGLFVHYWDS   601
mGluR1 498 GTWH--EGVLNIDDYKIQMNK--SGMVRSVCSEPCLKGQIKVIRKGEVSCCWICTACKENEFVQ---DEFTCRACDLGWWPNAELTGCEPIPVRYLEWSDIESIIAIAFSCLGILVTLFVTLIFVLYRDT   620

hT1R1  595 PVVRSAGGRLCFLMLGSLAAGSGSLYGFFGEPTRPACLLRQALFALGFTIFLSCLTVRSFQLIIIFKFSTKVPTFYHAWVQNHGAGLFVM-ISSAAQLLICLTWLVVWTPLPA-REYQRFPHLVMLECTE   722
rT1R1  594 PVVRSAGGRLCFLMLGSLVAGSCSFYSFFGEPTVPACLLRQPLFSLGFAIFLSCLTIRSFQLVIIFKFSTKVPTFYRTWAQNHGAGLFVI-VSSTVHLLICLTWLVMWTPRPT-REYQRFPHLVILECTE   721
hT1R2  594 PIVRSAGGPMCFLMLTLLLVAYMVVPVYVGPPKVSTCLCRQALFPLCFTICISCIAVRSFQIVCAFKMASRFPRAYSYWVRYQGPYVSMA-FITVLKMVIVVIGMLATGLSPTTRTDPDDPKITIVSCNP   722
rT1R2  598 PMVRSAGGPMCFLMLVPLLLAFGMVPVYVGPPTVFSCFCRQAFFTVCFSICLSCITVRSFQIVCVFKMARRLPSAYSFWMRYHGPYVFVA-FITAIKVALVVGNMLATTINPIGRTDPDDPNIMILSCHP   726
hT1R3  597 PLVQASGGPLACFGLVCLGLVCLSVLLFPGQPSPARCLAQQPLSHLPLTGCLSTLFLQAAEIFVESELPLSWADRLSGCLRGPWAWLVVL-LAMLVEVALCTWYLVAFPPEVV-TDWHMLPTEALVHCRT   724
rT1R3  602 PLVQASGGSLFCFGLICLGLFCLSVLLFPGRPRSASCLAQQPMAHLPLTGCLSTLFLQAAEIFVESELPLSWANWLCSYLRGPWAWLVVL-LATLVEAALCAWYLMAFPPEVV-TDWQVLPTEVLEHCRM   729
mGluR1 621 PVVKSSSRELCYIILAGIFLGYVCPFTLIAKPTTTSCYLQRLLVGLSSAMCYSALVTKTNRIARILAGSKKKICTRKPRFMSAWAQVIIASILISVQLTLVVTLIIMEPPMPI-LSYPSIK-EVYLICNT   748

hT1R1  723 TNSLGFLLAFLYNGLLSISAFACSYLGKDLPENYNEAKCVTFSLLFNFVSWIAFFTTASVYDGKYLPAANMMAGLSSLSSGFGGYFLPKCYVILCRPDLNSTEHFQASIQDYTRRCGST----------   841
rT1R1  722 VNSVGFLLAFTHNILLSISTFVCSYLGKELPENYNEAKCVTFSLLLNFVSWIAFFTMASIYQGSYLPAVNVLAGLTTLSGGFSGYFLPKCYVILCRPELNNTEHFQASIQDYTRRCGTT----------   840
hT1R2  723 NYRNSLLFNTSLDLLLSVVGFSFAYMGKELPTNYNEAKFITLSMTFYFTSSVSLCTFMSAYSGVLVTIVDLLVTVLNLLAISLGYFGPKCYMILFYPERNTPAYFNSMIQGYTMRRD------------   839
rT1R2  727 NYRNGLLFNTSMDLLLSVLGFSFAYMGKELPTNYNEAKFITLSMTFSFTSSISLCTFMSVHDGVLVTIMDLLVTVLNFLAIGLGYFGPKCYMILFYPERNTSAYFNSMIQGYTMRKS------------   843
hT1R3  725 RSWVSFGLAHATNATLAFLCFLGTFLVRSQPGRYNRARGLTFAMLAYFITWVSFVPLLANVQVVLRPAVQMGALLLCVLGILAAFHLPRCYLLMRQPGLNTPEFFLGGGPGDAQGQNDGN-TGNQGKHE   852
rT1R3  730 RSWVSLGLVHITNAVLAFLCFLGTFLVQSQPGRYNRARGLTFAMLAYFIIWVSFVPLLANVQVAYQPAVQMGAILFCALGILATFHLPKCYVLLWLPELNTQEFFLGRSPKEASDGNSGSSEATRGHSE   858
mGluR1 749 SN-LGVVAPVGYNGLLIMSCTYYAFKTRNVPANFNEAKYIAFTMYTTCIIWLAFVPIYFGSN--YKIITTCFAVSLSVTVALGCMFTPKMYIIIAKPERN------------------------------   845
```

FIG. 1B

SEQUENCE LISTING

```
<160> NUMBER OF SEQ ID NOS: 19

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: PDZIP
      sequence

<400> SEQUENCE: 1

Ser Val Ser Thr Trp
  1             5


<210> SEQ ID NO 2
<211> LENGTH: 14
<212> TYPE: PRT
<213> ORGANISM: Artificial Sequence
<220> FEATURE:
<223> OTHER INFORMATION: Description of Artificial Sequence: Consensus
      sequence
```

<220> FEATURE:
<221> NAME/KEY: MOD_RES
<222> LOCATION: (1)
<223> OTHER INFORMATION: Thr or Arg
<220> FEATURE:
<221> NAME/KEY: MOD_RES
<222> LOCATION: (3)
<223> OTHER INFORMATION: Phe or Leu
<220> FEATURE:
<221> NAME/KEY: MOD_RES
<222> LOCATION: (4)
<223> OTHER INFORMATION: Arg, Gln or Pro
<220> FEATURE:
<221> NAME/KEY: MOD_RES
<222> LOCATION: (6)
<223> OTHER INFORMATION: Arg or Thr
<220> FEATURE:
<221> NAME/KEY: MOD_RES
<222> LOCATION: (7)
<223> OTHER INFORMATION: Ser, Pro or Val
<220> FEATURE:
<221> NAME/KEY: MOD_RES
<222> LOCATION: (8)
<223> OTHER INFORMATION: Val, Glu, Arg, Lys or Thr
<220> FEATURE:
<221> NAME/KEY: MOD_RES
<222> LOCATION: (11)
<223> OTHER INFORMATION: Ala or Glu
<220> FEATURE:
<221> NAME/KEY: MOD_RES
<222> LOCATION: (12)
<223> OTHER INFORMATION: Trp or Leu
<220> FEATURE:
<221> NAME/KEY: MOD_RES
<222> LOCATION: (13)
<223> OTHER INFORMATION: Arg, His or Gly

<400> SEQUENCE: 2

```
Xaa Cys Xaa Xaa Arg Xaa Xaa Xaa Phe Leu Xaa Xaa Xaa Glu
  1               5                  10
```

<210> SEQ ID NO 3
<211> LENGTH: 15
<212> TYPE: PRT
<213> ORGANISM: Artificial Sequence
<220> FEATURE:
<223> OTHER INFORMATION: Description of Artificial Sequence: Consensus sequence
<220> FEATURE:
<221> NAME/KEY: MOD_RES
<222> LOCATION: (1)
<223> OTHER INFORMATION: Leu or Gln
<220> FEATURE:
<221> NAME/KEY: MOD_RES
<222> LOCATION: (3)
<223> OTHER INFORMATION: Glu, Gly or Thr
<220> FEATURE:
<221> NAME/KEY: MOD_RES
<222> LOCATION: (4)
<223> OTHER INFORMATION: Asn, Arg or Cys
<220> FEATURE:
<221> NAME/KEY: MOD_RES
<222> LOCATION: (7)
<223> OTHER INFORMATION: Arg or Glu
<220> FEATURE:
<221> NAME/KEY: MOD_RES
<222> LOCATION: (9)
<223> OTHER INFORMATION: Arg or Lys
<220> FEATURE:
<221> NAME/KEY: MOD_RES
<222> LOCATION: (10)
<223> OTHER INFORMATION: Cys, Gly or Phe
<220> FEATURE:
<221> NAME/KEY: MOD_RES
<222> LOCATION: (11)
<223> OTHER INFORMATION: Val, Leu or Ile

```
<220> FEATURE:
<221> NAME/KEY: MOD_RES
<222> LOCATION: (13)
<223> OTHER INFORMATION: Phe or Leu
<220> FEATURE:
<221> NAME/KEY: MOD_RES
<222> LOCATION: (14)
<223> OTHER INFORMATION: Ala or Ser
<220> FEATURE:
<221> NAME/KEY: MOD_RES
<222> LOCATION: (15)
<223> OTHER INFORMATION: Met or Leu

<400> SEQUENCE: 3

Xaa Pro Xaa Xaa Tyr Asn Xaa Ala Xaa Xaa Xaa Thr Xaa Xaa Xaa
  1               5                  10                  15


<210> SEQ ID NO 4
<211> LENGTH: 858
<212> TYPE: PRT
<213> ORGANISM: Rattus sp.

<400> SEQUENCE: 4

Met Pro Gly Leu Ala Ile Leu Gly Leu Ser Leu Ala Ala Phe Leu Glu
  1               5                  10                  15

Leu Gly Met Gly Ser Ser Leu Cys Leu Ser Gln Gln Phe Lys Ala Gln
             20                  25                  30

Gly Asp Tyr Ile Leu Gly Gly Leu Phe Pro Leu Gly Thr Thr Glu Glu
         35                  40                  45

Ala Thr Leu Asn Gln Arg Thr Gln Pro Asn Gly Ile Leu Cys Thr Arg
     50                  55                  60

Phe Ser Pro Leu Gly Leu Phe Leu Ala Met Ala Met Lys Met Ala Val
 65                  70                  75                  80

Glu Glu Ile Asn Asn Gly Ser Ala Leu Leu Pro Gly Leu Arg Leu Gly
                 85                  90                  95

Tyr Asp Leu Phe Asp Thr Cys Ser Glu Pro Val Val Thr Met Lys Pro
            100                 105                 110

Ser Leu Met Phe Met Ala Lys Val Gly Ser Gln Ser Ile Ala Ala Tyr
        115                 120                 125

Cys Asn Tyr Thr Gln Tyr Gln Pro Arg Val Leu Ala Val Ile Gly Pro
    130                 135                 140

His Ser Ser Glu Leu Ala Leu Ile Thr Gly Lys Phe Phe Ser Phe Phe
145                 150                 155                 160

Leu Met Pro Gln Val Ser Tyr Ser Ala Ser Met Asp Arg Leu Ser Asp
                165                 170                 175

Arg Glu Thr Phe Pro Ser Phe Phe Arg Thr Val Pro Ser Asp Arg Val
            180                 185                 190

Gln Leu Gln Ala Val Val Thr Leu Leu Gln Asn Phe Ser Trp Asn Trp
        195                 200                 205

Val Ala Ala Leu Gly Ser Asp Asp Asp Tyr Gly Arg Glu Gly Leu Ser
    210                 215                 220

Ile Phe Ser Gly Leu Ala Asn Ser Arg Gly Ile Cys Ile Ala His Glu
225                 230                 235                 240

Gly Leu Val Pro Gln His Asp Thr Ser Gly Gln Gln Leu Gly Lys Val
                245                 250                 255

Val Asp Val Leu Arg Gln Val Asn Gln Ser Lys Val Gln Val Val Val
            260                 265                 270

Leu Phe Ala Ser Ala Arg Ala Val Tyr Ser Leu Phe Ser Tyr Ser Ile
        275                 280                 285
```

-continued

```
Leu His Asp Leu Ser Pro Lys Val Trp Val Ala Ser Glu Ser Trp Leu
    290                 295                 300

Thr Ser Asp Leu Val Met Thr Leu Pro Asn Ile Ala Arg Val Gly Thr
305                 310                 315                 320

Val Leu Gly Phe Leu Gln Arg Gly Ala Leu Leu Pro Glu Phe Ser His
                325                 330                 335

Tyr Val Glu Thr Arg Leu Ala Leu Ala Ala Asp Pro Thr Phe Cys Ala
            340                 345                 350

Ser Leu Lys Ala Glu Leu Asp Leu Glu Glu Arg Val Met Gly Pro Arg
        355                 360                 365

Cys Ser Gln Cys Asp Tyr Ile Met Leu Gln Asn Leu Ser Ser Gly Leu
    370                 375                 380

Met Gln Asn Leu Ser Ala Gly Gln Leu His His Gln Ile Phe Ala Thr
385                 390                 395                 400

Tyr Ala Ala Val Tyr Ser Val Ala Gln Ala Leu His Asn Thr Leu Gln
                405                 410                 415

Cys Asn Val Ser His Cys His Thr Ser Glu Pro Val Gln Pro Trp Gln
            420                 425                 430

Leu Leu Glu Asn Met Tyr Asn Met Ser Phe Arg Ala Arg Asp Leu Thr
        435                 440                 445

Leu Gln Phe Asp Ala Lys Gly Ser Val Asp Met Glu Tyr Asp Leu Lys
    450                 455                 460

Met Trp Val Trp Gln Ser Pro Thr Pro Val Leu His Thr Val Gly Thr
465                 470                 475                 480

Phe Asn Gly Thr Leu Gln Leu Gln His Ser Lys Met Tyr Trp Pro Gly
                485                 490                 495

Asn Gln Val Pro Val Ser Gln Cys Ser Arg Gln Cys Lys Asp Gly Gln
            500                 505                 510

Val Arg Arg Val Lys Gly Phe His Ser Cys Cys Tyr Asp Cys Val Asp
        515                 520                 525

Cys Lys Ala Gly Ser Tyr Arg Lys His Pro Asp Asp Phe Thr Cys Thr
    530                 535                 540

Pro Cys Gly Lys Asp Gln Trp Ser Pro Glu Lys Ser Thr Thr Cys Leu
545                 550                 555                 560

Pro Arg Arg Pro Lys Phe Leu Ala Trp Gly Glu Pro Ala Val Leu Ser
                565                 570                 575

Leu Leu Leu Leu Leu Cys Leu Val Leu Gly Leu Thr Leu Ala Ala Leu
            580                 585                 590

Gly Leu Phe Val His Tyr Trp Asp Ser Pro Leu Val Gln Ala Ser Gly
        595                 600                 605

Gly Ser Leu Phe Cys Phe Gly Leu Ile Cys Leu Gly Leu Phe Cys Leu
    610                 615                 620

Ser Val Leu Leu Phe Pro Gly Arg Pro Arg Ser Ala Ser Cys Leu Ala
625                 630                 635                 640

Gln Gln Pro Met Ala His Leu Pro Leu Thr Gly Cys Leu Ser Thr Leu
                645                 650                 655

Phe Leu Gln Ala Ala Glu Ile Phe Val Glu Ser Glu Leu Pro Leu Ser
            660                 665                 670

Trp Ala Asn Trp Leu Cys Ser Tyr Leu Arg Gly Pro Trp Ala Trp Leu
        675                 680                 685

Val Val Leu Leu Ala Thr Leu Val Glu Ala Ala Leu Cys Ala Trp Tyr
    690                 695                 700
```

```
Leu Met Ala Phe Pro Pro Glu Val Val Thr Asp Trp Gln Val Leu Pro
705                 710                 715                 720

Thr Glu Val Leu Glu His Cys Arg Met Arg Ser Trp Val Ser Leu Gly
                725                 730                 735

Leu Val His Ile Thr Asn Ala Val Leu Ala Phe Leu Cys Phe Leu Gly
            740                 745                 750

Thr Phe Leu Val Gln Ser Gln Pro Gly Arg Tyr Asn Arg Ala Arg Gly
        755                 760                 765

Leu Thr Phe Ala Met Leu Ala Tyr Phe Ile Ile Trp Val Ser Phe Val
    770                 775                 780

Pro Leu Leu Ala Asn Val Gln Val Ala Tyr Gln Pro Ala Val Gln Met
785                 790                 795                 800

Gly Ala Ile Leu Phe Cys Ala Leu Gly Ile Leu Ala Thr Phe His Leu
                805                 810                 815

Pro Lys Cys Tyr Val Leu Leu Trp Leu Pro Glu Leu Asn Thr Gln Glu
            820                 825                 830

Phe Phe Leu Gly Arg Ser Pro Lys Glu Ala Ser Asp Gly Asn Ser Gly
        835                 840                 845

Ser Ser Glu Ala Thr Arg Gly His Ser Glu
    850                 855


<210> SEQ ID NO 5
<211> LENGTH: 841
<212> TYPE: PRT
<213> ORGANISM: Homo sapiens

<400> SEQUENCE: 5

Met Leu Leu Cys Thr Ala Arg Leu Val Gly Leu Gln Leu Leu Ile Ser
  1               5                  10                  15

Cys Cys Trp Ala Phe Ala Cys His Ser Thr Glu Ser Ser Pro Asp Phe
            20                  25                  30

Thr Leu Pro Gly Asp Tyr Leu Leu Ala Gly Leu Phe Pro Leu His Ser
        35                  40                  45

Gly Cys Leu Gln Val Arg His Arg Pro Glu Val Thr Leu Cys Asp Arg
    50                  55                  60

Ser Cys Ser Phe Asn Glu His Gly Tyr His Leu Phe Gln Ala Met Arg
 65                  70                  75                  80

Leu Gly Val Glu Glu Ile Asn Asn Ser Thr Ala Leu Leu Pro Asn Ile
                85                  90                  95

Thr Leu Gly Tyr Gln Leu Tyr Asp Val Cys Ser Asp Ser Ala Asn Val
            100                 105                 110

Tyr Ala Thr Leu Arg Val Leu Ser Leu Pro Gly Gln His His Ile Glu
        115                 120                 125

Leu Gln Gly Asp Leu Leu His Tyr Ser Pro Thr Val Leu Ala Val Ile
    130                 135                 140

Gly Pro Asp Ser Thr Asn Arg Ala Ala Thr Thr Ala Ala Leu Leu Ser
145                 150                 155                 160

Pro Phe Leu Val Pro Met Ile Ser Tyr Ala Ala Ser Ser Glu Thr Leu
                165                 170                 175

Ser Val Lys Arg Gln Tyr Pro Ser Phe Leu Arg Thr Ile Pro Asn Asp
            180                 185                 190

Lys Tyr Gln Val Glu Thr Met Val Leu Leu Leu Gln Lys Phe Gly Trp
        195                 200                 205

Thr Trp Ile Ser Leu Val Gly Ser Ser Asp Asp Tyr Gly Gln Leu Gly
    210                 215                 220
```

-continued

```
Val Gln Ala Leu Glu Asn Gln Ala Thr Gly Gln Gly Ile Cys Ile Ala
225                 230                 235                 240

Phe Lys Asp Ile Met Pro Phe Ser Ala Gln Val Gly Asp Glu Arg Met
                245                 250                 255

Gln Cys Leu Met Arg His Leu Ala Gln Ala Gly Ala Thr Val Val Val
            260                 265                 270

Val Phe Ser Ser Arg Gln Leu Ala Arg Val Phe Phe Glu Ser Val Val
        275                 280                 285

Leu Thr Asn Leu Thr Gly Lys Val Trp Val Ala Ser Glu Ala Trp Ala
    290                 295                 300

Leu Ser Arg His Ile Thr Gly Val Pro Gly Ile Gln Arg Ile Gly Met
305                 310                 315                 320

Val Leu Gly Val Ala Ile Gln Lys Arg Ala Val Pro Gly Leu Lys Ala
                325                 330                 335

Phe Glu Glu Ala Tyr Ala Arg Ala Asp Lys Lys Ala Pro Arg Pro Cys
            340                 345                 350

His Lys Gly Ser Trp Cys Ser Ser Asn Gln Leu Cys Arg Glu Cys Gln
        355                 360                 365

Ala Phe Met Ala His Thr Met Pro Lys Leu Lys Ala Phe Ser Met Ser
    370                 375                 380

Ser Ala Tyr Asn Ala Tyr Arg Ala Val Tyr Ala Val Ala His Gly Leu
385                 390                 395                 400

His Gln Leu Leu Gly Cys Ala Ser Gly Ala Cys Ser Arg Gly Arg Val
                405                 410                 415

Tyr Pro Trp Gln Leu Leu Glu Gln Ile His Lys Val His Phe Leu Leu
            420                 425                 430

His Lys Asp Thr Val Ala Phe Asn Asp Asn Arg Asp Pro Leu Ser Ser
        435                 440                 445

Tyr Asn Ile Ile Ala Trp Asp Trp Asn Gly Pro Lys Trp Thr Phe Thr
    450                 455                 460

Val Leu Gly Ser Ser Thr Trp Ser Pro Val Gln Leu Asn Ile Asn Glu
465                 470                 475                 480

Thr Lys Ile Gln Trp His Gly Lys Asp Asn Gln Val Pro Lys Ser Val
                485                 490                 495

Cys Ser Ser Asp Cys Leu Glu Gly His Gln Arg Val Val Thr Gly Phe
            500                 505                 510

His His Cys Cys Phe Glu Cys Val Pro Cys Gly Ala Gly Thr Phe Leu
        515                 520                 525

Asn Lys Ser Asp Leu Tyr Arg Cys Gln Pro Cys Gly Lys Glu Glu Trp
    530                 535                 540

Ala Pro Glu Gly Ser Gln Thr Cys Phe Pro Arg Thr Val Val Phe Leu
545                 550                 555                 560

Ala Leu Arg Glu His Thr Ser Trp Val Leu Leu Ala Ala Asn Thr Leu
                565                 570                 575

Leu Leu Leu Leu Leu Leu Gly Thr Ala Gly Leu Phe Ala Trp His Leu
            580                 585                 590

Asp Thr Pro Val Val Arg Ser Ala Gly Gly Arg Leu Cys Phe Leu Met
        595                 600                 605

Leu Gly Ser Leu Ala Ala Gly Ser Gly Ser Leu Tyr Gly Phe Phe Gly
    610                 615                 620

Glu Pro Thr Arg Pro Ala Cys Leu Leu Arg Gln Ala Leu Phe Ala Leu
625                 630                 635                 640
```

```
Gly Phe Thr Ile Phe Leu Ser Cys Leu Thr Val Arg Ser Phe Gln Leu
                645                 650                 655

Ile Ile Ile Phe Lys Phe Ser Thr Lys Val Pro Thr Phe Tyr His Ala
            660                 665                 670

Trp Val Gln Asn His Gly Ala Gly Leu Phe Val Met Ile Ser Ser Ala
        675                 680                 685

Ala Gln Leu Leu Ile Cys Leu Thr Trp Leu Val Val Trp Thr Pro Leu
    690                 695                 700

Pro Ala Arg Glu Tyr Gln Arg Phe Pro His Leu Val Met Leu Glu Cys
705                 710                 715                 720

Thr Glu Thr Asn Ser Leu Gly Phe Ile Leu Ala Phe Leu Tyr Asn Gly
                725                 730                 735

Leu Leu Ser Ile Ser Ala Phe Ala Cys Ser Tyr Leu Gly Lys Asp Leu
            740                 745                 750

Pro Glu Asn Tyr Asn Glu Ala Lys Cys Val Thr Phe Ser Leu Leu Phe
        755                 760                 765

Asn Phe Val Ser Trp Ile Ala Phe Phe Thr Thr Ala Ser Val Tyr Asp
    770                 775                 780

Gly Lys Tyr Leu Pro Ala Ala Asn Met Met Ala Gly Leu Ser Ser Leu
785                 790                 795                 800

Ser Ser Gly Phe Gly Gly Tyr Phe Leu Pro Lys Cys Tyr Val Ile Leu
                805                 810                 815

Cys Arg Pro Asp Leu Asn Ser Thr Glu His Phe Gln Ala Ser Ile Gln
            820                 825                 830

Asp Tyr Thr Arg Arg Cys Gly Ser Thr
        835                 840


<210> SEQ ID NO 6
<211> LENGTH: 839
<212> TYPE: PRT
<213> ORGANISM: Homo sapiens

<400> SEQUENCE: 6

Met Gly Pro Arg Ala Lys Thr Ile Cys Ser Leu Phe Phe Leu Leu Trp
  1               5                  10                  15

Val Leu Ala Glu Pro Ala Glu Asn Ser Asp Phe Tyr Leu Pro Gly Asp
            20                  25                  30

Tyr Leu Leu Gly Gly Leu Phe Ser Leu His Ala Asn Met Lys Gly Ile
        35                  40                  45

Val His Leu Asn Phe Leu Gln Val Pro Met Cys Lys Glu Tyr Glu Val
     50                  55                  60

Lys Val Ile Gly Tyr Asn Leu Met Gln Ala Met Arg Phe Ala Val Glu
 65                  70                  75                  80

Glu Ile Asn Asn Asp Ser Ser Leu Leu Pro Gly Val Leu Leu Gly Tyr
                 85                  90                  95

Glu Ile Val Asp Val Cys Tyr Ile Ser Asn Asn Val Gln Pro Val Leu
            100                 105                 110

Tyr Phe Leu Ala His Glu Asp Asn Leu Leu Pro Ile Gln Glu Asp Tyr
        115                 120                 125

Ser Asn Tyr Ile Ser Arg Val Val Ala Val Ile Gly Pro Asp Asn Ser
    130                 135                 140

Glu Ser Val Met Thr Val Ala Asn Phe Leu Ser Leu Phe Leu Leu Pro
145                 150                 155                 160

Gln Ile Thr Tyr Ser Ala Ile Ser Asp Glu Leu Arg Asp Lys Val Arg
                165                 170                 175
```

-continued

```
Phe Pro Ala Leu Leu Arg Thr Thr Pro Ser Ala Asp His His Val Glu
            180                 185                 190

Ala Met Val Gln Leu Met Leu His Phe Arg Trp Asn Trp Ile Ile Val
        195                 200                 205

Leu Val Ser Ser Asp Thr Tyr Gly Arg Asp Asn Gly Gln Leu Leu Gly
    210                 215                 220

Glu Arg Val Ala Arg Arg Asp Ile Cys Ile Ala Phe Gln Glu Thr Leu
225                 230                 235                 240

Pro Thr Leu Gln Pro Asn Gln Asn Met Thr Ser Glu Glu Arg Gln Arg
                245                 250                 255

Leu Val Thr Ile Val Asp Lys Leu Gln Gln Ser Thr Ala Arg Val Val
            260                 265                 270

Val Val Phe Ser Pro Asp Leu Thr Leu Tyr His Phe Phe Asn Glu Val
        275                 280                 285

Leu Arg Gln Asn Phe Thr Gly Ala Val Trp Ile Ala Ser Glu Ser Trp
    290                 295                 300

Ala Ile Asp Pro Val Leu His Asn Leu Thr Glu Leu Gly His Leu Gly
305                 310                 315                 320

Thr Phe Leu Gly Ile Thr Ile Gln Ser Val Pro Ile Pro Gly Phe Ser
                325                 330                 335

Glu Phe Arg Glu Trp Gly Pro Gln Ala Gly Pro Pro Pro Leu Ser Arg
            340                 345                 350

Thr Ser Gln Ser Tyr Thr Cys Asn Gln Glu Cys Asp Asn Cys Leu Asn
        355                 360                 365

Ala Thr Leu Ser Phe Asn Thr Ile Leu Arg Leu Ser Gly Glu Arg Val
    370                 375                 380

Val Tyr Ser Val Tyr Ser Ala Val Tyr Ala Val Ala His Ala Leu His
385                 390                 395                 400

Ser Leu Leu Gly Cys Asp Lys Ser Thr Cys Thr Lys Arg Val Val Tyr
                405                 410                 415

Pro Trp Gln Leu Leu Glu Glu Ile Trp Lys Val Asn Phe Thr Leu Leu
            420                 425                 430

Asp His Gln Ile Phe Phe Asp Pro Gln Gly Asp Val Ala Leu His Leu
        435                 440                 445

Glu Ile Val Gln Trp Gln Trp Asp Arg Ser Gln Asn Pro Phe Gln Ser
    450                 455                 460

Val Ala Ser Tyr Tyr Pro Leu Gln Arg Gln Leu Lys Asn Ile Gln Asp
465                 470                 475                 480

Ile Ser Trp His Thr Val Asn Asn Thr Ile Pro Met Ser Met Cys Ser
                485                 490                 495

Lys Arg Cys Gln Ser Gly Gln Lys Lys Lys Pro Val Gly Ile His Val
            500                 505                 510

Cys Cys Phe Glu Cys Ile Asp Cys Leu Pro Gly Thr Phe Leu Asn His
        515                 520                 525

Thr Glu Asp Glu Tyr Glu Cys Gln Ala Cys Pro Asn Asn Glu Trp Ser
    530                 535                 540

Tyr Gln Ser Glu Thr Ser Cys Phe Lys Arg Gln Leu Val Phe Leu Glu
545                 550                 555                 560

Trp His Glu Ala Pro Thr Ile Ala Val Ala Leu Leu Ala Ala Leu Gly
                565                 570                 575

Phe Leu Ser Thr Leu Ala Ile Leu Val Ile Phe Trp Arg His Phe Gln
            580                 585                 590
```

```
Thr Pro Ile Val Arg Ser Ala Gly Gly Pro Met Cys Phe Leu Met Leu
        595                 600                 605

Thr Leu Leu Leu Val Ala Tyr Met Val Val Pro Val Tyr Val Gly Pro
    610                 615                 620

Pro Lys Val Ser Thr Cys Leu Cys Arg Gln Ala Leu Phe Pro Leu Cys
625                 630                 635                 640

Phe Thr Ile Cys Ile Ser Cys Ile Ala Val Arg Ser Phe Gln Ile Val
                645                 650                 655

Cys Ala Phe Lys Met Ala Ser Arg Phe Pro Arg Ala Tyr Ser Tyr Trp
            660                 665                 670

Val Arg Tyr Gln Gly Pro Tyr Val Ser Met Ala Phe Ile Thr Val Leu
        675                 680                 685

Lys Met Val Ile Val Val Ile Gly Met Leu Ala Thr Gly Leu Ser Pro
    690                 695                 700

Thr Thr Arg Thr Asp Pro Asp Asp Pro Lys Ile Thr Ile Val Ser Cys
705                 710                 715                 720

Asn Pro Asn Tyr Arg Asn Ser Leu Leu Phe Asn Thr Ser Leu Asp Leu
                725                 730                 735

Leu Leu Ser Val Val Gly Phe Ser Phe Ala Tyr Met Gly Lys Glu Leu
            740                 745                 750

Pro Thr Asn Tyr Asn Glu Ala Lys Phe Ile Thr Leu Ser Met Thr Phe
        755                 760                 765

Tyr Phe Thr Ser Ser Val Ser Leu Cys Thr Phe Met Ser Ala Tyr Ser
    770                 775                 780

Gly Val Leu Val Thr Ile Val Asp Leu Leu Val Thr Val Leu Asn Leu
785                 790                 795                 800

Leu Ala Ile Ser Leu Gly Tyr Phe Gly Pro Lys Cys Tyr Met Ile Leu
                805                 810                 815

Phe Tyr Pro Glu Arg Asn Thr Pro Ala Tyr Phe Asn Ser Met Ile Gln
            820                 825                 830

Gly Tyr Thr Met Arg Arg Asp
        835


<210> SEQ ID NO 7
<211> LENGTH: 852
<212> TYPE: PRT
<213> ORGANISM: Homo sapiens

<400> SEQUENCE: 7

Met Leu Gly Pro Ala Val Leu Gly Leu Ser Leu Trp Ala Leu Leu His
 1               5                  10                  15

Pro Gly Thr Gly Ala Pro Leu Cys Leu Ser Gln Gln Leu Arg Met Lys
            20                  25                  30

Gly Asp Tyr Val Leu Gly Gly Leu Phe Pro Leu Gly Glu Ala Glu Glu
        35                  40                  45

Ala Gly Leu Arg Ser Arg Thr Arg Pro Ser Ser Pro Val Cys Thr Arg
    50                  55                  60

Phe Ser Ser Asn Gly Leu Leu Trp Ala Leu Ala Met Lys Met Ala Val
65                  70                  75                  80

Glu Glu Ile Asn Asn Lys Ser Asp Leu Leu Pro Gly Leu Arg Leu Gly
                85                  90                  95

Tyr Asp Leu Phe Asp Thr Cys Ser Glu Pro Val Val Ala Met Lys Pro
            100                 105                 110

Ser Leu Met Phe Leu Ala Lys Ala Gly Ser Arg Asp Ile Ala Ala Tyr
        115                 120                 125
```

-continued

```
Cys Asn Tyr Thr Gln Tyr Gln Pro Arg Val Leu Ala Val Ile Gly Pro
    130                 135                 140

His Ser Ser Glu Leu Ala Met Val Thr Gly Lys Phe Phe Ser Phe Phe
145                 150                 155                 160

Leu Met Pro Gln Val Ser Tyr Gly Ala Ser Met Glu Leu Leu Ser Ala
                165                 170                 175

Arg Glu Thr Phe Pro Ser Phe Phe Arg Thr Val Pro Ser Asp Arg Val
            180                 185                 190

Gln Leu Thr Ala Ala Ala Glu Leu Leu Gln Glu Phe Gly Trp Asn Trp
        195                 200                 205

Val Ala Ala Leu Gly Ser Asp Asp Glu Tyr Gly Arg Gln Gly Leu Ser
    210                 215                 220

Ile Phe Ser Ala Leu Ala Ala Ala Arg Gly Ile Cys Ile Ala His Glu
225                 230                 235                 240

Gly Leu Val Pro Leu Pro Arg Ala Asp Asp Ser Arg Leu Gly Lys Val
                245                 250                 255

Gln Asp Val Leu His Gln Val Asn Gln Ser Ser Val Gln Val Val Leu
            260                 265                 270

Leu Phe Ala Ser Val His Ala Ala His Ala Leu Phe Asn Tyr Ser Ile
        275                 280                 285

Ser Ser Arg Leu Ser Pro Lys Val Trp Val Ala Ser Glu Ala Trp Leu
    290                 295                 300

Thr Ser Asp Leu Val Met Gly Leu Pro Gly Met Ala Gln Met Gly Thr
305                 310                 315                 320

Val Leu Gly Phe Leu Gln Arg Gly Ala Gln Leu His Glu Phe Pro Gln
                325                 330                 335

Tyr Val Lys Thr His Leu Ala Leu Ala Thr Asp Pro Ala Phe Cys Ser
            340                 345                 350

Ala Leu Gly Glu Arg Glu Gln Gly Leu Glu Glu Asp Val Val Gly Gln
        355                 360                 365

Arg Cys Pro Gln Cys Asp Cys Ile Thr Leu Gln Asn Val Ser Ala Gly
    370                 375                 380

Leu Asn His His Gln Thr Phe Ser Val Tyr Ala Ala Val Tyr Ser Val
385                 390                 395                 400

Ala Gln Ala Leu His Asn Thr Leu Gln Cys Asn Ala Ser Gly Cys Pro
                405                 410                 415

Ala Gln Asp Pro Val Lys Pro Trp Gln Leu Leu Glu Asn Met Tyr Asn
            420                 425                 430

Leu Thr Phe His Val Gly Gly Leu Pro Leu Arg Phe Asp Ser Ser Gly
        435                 440                 445

Asn Val Asp Met Glu Tyr Asp Leu Lys Leu Trp Val Trp Gln Gly Ser
    450                 455                 460

Val Pro Arg Leu His Asp Val Gly Arg Phe Asn Gly Ser Leu Arg Thr
465                 470                 475                 480

Glu Arg Leu Lys Ile Arg Trp His Thr Ser Asp Asn Gln Lys Pro Val
                485                 490                 495

Ser Arg Cys Ser Arg Gln Cys Gln Glu Gly Gln Val Arg Arg Val Lys
            500                 505                 510

Gly Phe His Ser Cys Cys Tyr Asp Cys Val Asp Cys Glu Ala Gly Ser
        515                 520                 525

Tyr Arg Gln Asn Pro Asp Asp Ile Ala Cys Thr Phe Cys Gly Gln Asp
    530                 535                 540
```

-continued

```
Glu Trp Ser Pro Glu Arg Ser Thr Arg Cys Phe Arg Arg Arg Ser Arg
545                 550                 555                 560

Phe Leu Ala Trp Gly Glu Pro Ala Val Leu Leu Leu Leu Leu Leu Leu
                565                 570                 575

Ser Leu Ala Leu Gly Leu Val Leu Ala Ala Leu Gly Leu Phe Val His
            580                 585                 590

His Arg Asp Ser Pro Leu Val Gln Ala Ser Gly Gly Pro Leu Ala Cys
        595                 600                 605

Phe Gly Leu Val Cys Leu Gly Leu Val Cys Leu Ser Val Leu Leu Phe
    610                 615                 620

Pro Gly Gln Pro Ser Pro Ala Arg Cys Leu Ala Gln Gln Pro Leu Ser
625                 630                 635                 640

His Leu Pro Leu Thr Gly Cys Leu Ser Thr Leu Phe Leu Gln Ala Ala
                645                 650                 655

Glu Ile Phe Val Glu Ser Glu Leu Pro Leu Ser Trp Ala Asp Arg Leu
            660                 665                 670

Ser Gly Cys Leu Arg Gly Pro Trp Ala Trp Leu Val Val Leu Leu Ala
        675                 680                 685

Met Leu Val Glu Val Ala Leu Cys Thr Trp Tyr Leu Val Ala Phe Pro
    690                 695                 700

Pro Glu Val Val Thr Asp Trp His Met Leu Pro Thr Glu Ala Leu Val
705                 710                 715                 720

His Cys Arg Thr Arg Ser Trp Val Ser Phe Gly Leu Ala His Ala Thr
                725                 730                 735

Asn Ala Thr Leu Ala Phe Leu Cys Phe Leu Gly Thr Phe Leu Val Arg
            740                 745                 750

Ser Gln Pro Gly Arg Tyr Asn Arg Ala Arg Gly Leu Thr Phe Ala Met
        755                 760                 765

Leu Ala Tyr Phe Ile Thr Trp Val Ser Phe Val Pro Leu Leu Ala Asn
    770                 775                 780

Val Gln Val Val Leu Arg Pro Ala Val Gln Met Gly Ala Leu Leu Leu
785                 790                 795                 800

Cys Val Leu Gly Ile Leu Ala Ala Phe His Leu Pro Arg Cys Tyr Leu
                805                 810                 815

Leu Met Arg Gln Pro Gly Leu Asn Thr Pro Glu Phe Phe Leu Gly Gly
            820                 825                 830

Gly Pro Gly Asp Ala Gln Gly Gln Asn Asp Gly Asn Thr Gly Asn Gln
        835                 840                 845

Gly Lys His Glu
    850


<210> SEQ ID NO 8
<211> LENGTH: 2526
<212> TYPE: DNA
<213> ORGANISM: Homo sapiens

<400> SEQUENCE: 8

atgctgctct gcacggctcg cctggtcggc ctgcagcttc tcatttcctg ctgctgggcc      60

tttgcctgcc atagcacgga gtcttctcct gacttcaccc tccccggaga ttacctcctg     120

gcaggcctgt tccctctcca ttctggctgt ctgcaggtga ggcacagacc cgaggtgacc     180

ctgtgtgaca ggtcttgtag cttcaatgag catggctacc acctcttcca ggctatgcgg     240

cttggggttg aggagataaa caactccacg gccctgctgc ccaacatcac cctggggtac     300

cagctgtatg atgtgtgttc tgactctgcc aatgtgtatg ccacgctgag agtgctctcc     360
```

-continued

```
ctgccagggc aacaccacat agagctccaa ggagaccttc tccactattc ccctacggtg    420

ctggcagtga ttgggcctga cagcaccaac cgtgctgcca ccacagccgc cctgctgagc    480

cctttcctgg tgcccatgat tagctatgcg gccagcagcg agacgctcag cgtgaagcgg    540

cagtatccct ctttcctgcg caccatcccc aatgacaagt accaggtgga gaccatggtg    600

ctgctgctgc agaagttcgg gtggacctgg atctctctgg ttggcagcag tgacgactat    660

gggcagctag ggtgcaggc actggagaac caggccactg gtcaggggat ctgcattgct    720

ttcaaggaca tcatgccctt ctctgcccag gtgggcgatg agaggatgca gtgcctcatg    780

cgccacctgg cccaggccgg ggccaccgtc gtggttgttt tttccagccg gcagttggcc    840

agggtgtttt tcgagtccgt ggtgctgacc aacctgactg gcaaggtgtg ggtcgcctca    900

gaagcctggg ccctctccag gcacatcact ggggtgcccg ggatccagcg cattgggatg    960

gtgctgggcg tggccatcca gaagagggct gtccctggcc tgaaggcgtt tgaagaagcc   1020

tatgcccggg cagacaagaa ggcccctagg ccttgccaca agggctcctg gtgcagcagc   1080

aatcagctct gcagagaatg ccaagctttc atggcacaca cgatgcccaa gctcaaagcc   1140

ttctccatga gttctgccta caacgcatac cgggctgtgt atgcggtggc ccatggcctc   1200

caccagctcc tgggctgtgc ctctggagct tgttccaggg gccgagtcta cccctggcag   1260

cttttggagc agatccacaa ggtgcatttc cttctacaca aggacactgt ggcgtttaat   1320

gacaacagag atcccctcag tagctataac ataattgcct gggactggaa tggacccaag   1380

tggaccttca cggtcctcgg ttcctccaca tggtctccag ttcagctaaa cataaatgag   1440

accaaaatcc agtggcacgg aaaggacaac caggtgccta agtctgtgtg ttccagcgac   1500

tgtcttgaag ggcaccagcg agtggttacg ggtttccatc actgctgctt tgagtgtgtg   1560

ccctgtgggg ctgggacctt cctcaacaag agtgacctct acagatgcca gccttgtggg   1620

aaagaagagt gggcacctga gggaagccag acctgcttcc cgcgcactgt ggtgtttttg   1680

gctttgcgtg agcacacctc ttgggtgctg ctggcagcta acacgctgct gctgctgctg   1740

ctgcttggga ctgctggcct gtttgcctgg cacctagaca cccctgtggt gaggtcagca   1800

gggggccgcc tgtgctttct tatgctgggc tccctggcag caggtagtgg cagcctctat   1860

ggcttctttg gggaacccac aaggcctgcg tgcttgctac gccaggccct ctttgccctt   1920

ggtttcacca tcttcctgtc ctgcctgaca gttcgctcat tccaactaat catcatcttc   1980

aagttttcca ccaaggtacc tacattctac cacgcctggg tccaaaacca cggtgctggc   2040

ctgtttgtga tgatcagctc agcggcccag ctgcttatct gtctaacttg gctggtggtg   2100

tggaccccac tgcctgctag ggaataccag cgcttccccc atctggtgat gcttgagtgc   2160

acagagacca actccctggg cttcatactg gccttcctct acaatggcct cctctccatc   2220

agtgcctttg cctgcagcta cctgggtaag gacttgccag agaactacaa cgaggccaaa   2280

tgtgtcacct tcagcctgct cttcaacttc gtgtcctgga tcgccttctt caccacggcc   2340

agcgtctacg acggcaagta cctgcctgcg gccaacatga tggctgggct gagcagcctg   2400

agcagcggct tcggtgggta ttttctgcct aagtgctacg tgatcctctg ccgcccagac   2460

ctcaacagca cagagcactt ccaggcctcc attcaggact acacgaggcg ctgcggctcc   2520

acctga                                                               2526
```

<210> SEQ ID NO 9
<211> LENGTH: 2559
<212> TYPE: DNA
<213> ORGANISM: Homo sapiens -continued

<400> SEQUENCE: 9

```
atgctgggcc ctgctgtcct gggcctcagc ctctgggctc tcctgcaccc tgggacgggg     60
gccccattgt gcctgtcaca gcaacttagg atgaaggggg actacgtgct ggggggggctg    120
ttcccctgg gcgaggccga ggaggctggc ctccgcagcc ggacacggcc cagcagccct    180
gtgtgcacca ggttctcctc aaacggcctg ctctgggcac tggccatgaa aatggccgtg    240
gaggagatca acaacaagtc ggatctgctg cccgggctgc gcctgggcta cgacctcttt    300
gatacgtgct cggagcctgt ggtggccatg aagcccagcc tcatgttcct ggccaaggca    360
ggcagccgcg acatcgccgc ctactgcaac tacacgcagt accagccccg tgtgctggct    420
gtcatcgggc cccactcgtc agagctcgcc atggtcaccg gcaagttctt cagcttcttc    480
ctcatgcccc aggtcagcta cggtgctagc atggagctgc tgagcgcccg ggagaccttc    540
ccctccttct tccgcaccgt gcccagcgac cgtgtgcagc tgacggccgc cgcggagctg    600
ctgcaggagt tcggctggaa ctgggtggcc gccctgggca gcgacgacga gtacggccgg    660
cagggcctga gcatcttctc ggccctggcc gcggcacgcg gcatctgcat cgcgcacgag    720
ggcctggtgc cgctgccccg tgccgatgac tcgcggctgg ggaaggtgca ggacgtcctg    780
caccaggtga accagagcag cgtgcaggtg gtgctgctgt tcgcctccgt gcacgccgcc    840
cacgccctct tcaactacag catcagcagc aggctctcgc ccaaggtgtg ggtggccagc    900
gaggcctggc tgacctctga cctggtcatg gggctgcccg gcatggccca gatgggcacg    960
gtgcttggct tcctccagag gggtgcccag ctgcacgagt tcccccagta cgtgaagacg   1020
cacctggccc tggccaccga cccggccttc tgctctgccc tgggcgagag ggagcagggt   1080
ctggaggagg acgtggtggg ccagcgctgc ccgcagtgtg actgcatcac gctgcagaac   1140
gtgagcgcag ggctaaatca ccaccagacg ttctctgtct acgcagctgt gtatagcgtg   1200
gcccaggccc tgcacaacac tcttcagtgc aacgcctcag gctgccccgc gcaggacccc   1260
gtgaagccct ggcagctcct ggagaacatg tacaacctga ccttccacgt gggcgggctg   1320
ccgctgcggt tcgacagcag cggaaacgtg gacatggagt acgacctgaa gctgtgggtg   1380
tggcagggct cagtgcccag gctccacgac gtgggcaggt tcaacggcag cctcaggaca   1440
gagcgcctga agatccgctg gcacacgtct gacaaccaga agcccgtgtc ccggtgctcg   1500
cggcagtgcc aggagggcca ggtgcgccgg gtcaaggggt tccactcctg ctgctacgac   1560
tgtgtggact gcgaggcggg cagctaccgg caaaacccag acgacatcgc ctgcaccttt   1620
tgtggccagg atgagtggtc cccggagcga agcacacgct gcttccgccg caggtctcgg   1680
ttcctggcat ggggcgagcc ggctgtgctg ctgctgctcc tgctgctgag cctggcgctg   1740
ggccttgtgc tggctgcttt ggggctgttc gttcaccatc gggacagccc actggttcag   1800
gcctcggggg ggcccctggc ctgctttggc ctggtgtgcc tgggcctggt ctgcctcagc   1860
gtcctcctgt tccctggcca gcccagccct gcccgatgcc tggcccagca gcccttgtcc   1920
cacctcccgc tcacgggctg cctgagcaca ctcttcctgc aggcggccga gatcttcgtg   1980
gagtcagaac tgcctctgag ctgggcagac cggctgagtg gctgcctgcg ggggccctgg   2040
gcctggctgg tggtgctgct ggccatgctg gtggaggtcg cactgtgcac ctggtacctg   2100
gtggccttcc cgccggaggt ggtgacggac tggcacatgc tgcccacgga ggcgctggtg   2160
cactgccgca cacgctcctg ggtcagcttc ggcctagcgc acgccaccaa tgccacgctg   2220
gcctttctct gcttcctggg cactttcctg gtgcggagcc agccgggctg ctacaaccgt   2280
gcccgtggcc tcacctttgc catgctggcc tacttcatca cctgggtctc ctttgtgccc   2340
```

-continued

```
ctcctggcca atgtgcaggt ggtcctcagg cccgccgtgc agatgggcgc cctcctgctc   2400

tgtgtcctgg gcatcctggc tgccttccac ctgcccaggt gttacctgct catgcggcag   2460

ccagggctca acacccccga gttcttcctg ggagggggcc ctggggatgc ccaaggccag   2520

aatgacggga acacaggaaa tcaggggaaa catgagtga                          2559


<210> SEQ ID NO 10
<211> LENGTH: 2519
<212> TYPE: DNA
<213> ORGANISM: Homo sapiens

<400> SEQUENCE: 10

atggggccca gggcaaagac catctgctcc ctgttcttcc tcctatgggt cctggctgag     60

ccggctgaga actcggactt ctacctgcct ggggattacc tcctgggtgg cctcttctcc    120

ctccatgcca acatgaaggg cattgttcac cttaacttcc tgcaggtgcc catgtgcaag    180

gagtatgaag tgaaggtgat aggctacaac ctcatgcagg ccatgcgctt cgcggtggag    240

gagatcaaca atgacagcag cctgctgcct ggtgtgctgc tgggctatga gatcgtggat    300

gtgtgctaca tctccaacaa tgtccagccg gtgctctact tcctggcaca cgaggacaac    360

ctccttccca tccaagagga ctacagtaac tacatttccc gtgtggtggc tgtcattggc    420

cctgacaact ccgagtctgt catgactgtg gccaacttcc tctccctatt tctccttcca    480

cagatcacct acagcgccat cagcgatgag ctgcgagaca aggtgcgctt cccggctttg    540

ctgcgtacca cacccagcgc cgaccaccac gtcgaggcca tggtgcagct gatgctgcac    600

ttccgctgga actggatcat tgtgctggtg agcagcgaca cctatggccg cgacaatggc    660

agctgcttgg cgagcgcgtg gcccggcgcg acatctgcat cgccttccag gagacgctgc    720

ccacactgca gcccaaccag aacatgacgt cagaggagcg ccagcgcctg gtgaccattg    780

tggacaagct gcagcagagc acagcgcgcg tcgtggtcgt gttctcgccc gacctgaccc    840

tgtaccactt cttcaatgag gtgctgcgcc agaacttcac gggcgccgtg tggatcgcct    900

ccgagtcctg ggccatcgac ccggtcctgc acaacctcac ggagctgggc cacttgggca    960

ccttcctggg catcaccatc cagagcgtgc ccatcccggg cttcagtgag ttccgcgagt   1020

ggggcccaca ggctgggccg ccacccctca gcaggaccag ccagagctat acctgcaacc   1080

aggagtgcga caactgcctg aacgccacct tgtccttcaa caccattctc aggctctctg   1140

gggagcgtgt cgtctacagc gtgtactctg cggtctatgc tgtggcccat gccctgcaca   1200

gcctcctcgg ctgtgacaaa agcacctgca ccaagagggt ggtctacccc tggcagctgc   1260

ttgaggagat ctggaaggtc aacttcactc tcctggacca ccaaatcttc ttcgacccgc   1320

aaggggacgt ggctctgcac ttggagattg tccagtggca atgggaccgg agccagaatc   1380

ccttccagag cgtcgcctcc tactaccccc tgcagcgaca gctgaagaac atccaagaca   1440

tctcctggca caccgtcaac aacacgatcc ctatgtccat gtgttccaag aggtgccagt   1500

cagggcaaaa gaagaagcct gtgggcatcc acgtctgctg cttcgagtgc atcgactgcc   1560

ttcccggcac cttcctcaac cacactgaag atgaatatga atgccaggcc tgcccgaata   1620

acgagtggtc ctaccagagt gagacctcct gcttcaagcg gcagctggtc ttcctggaat   1680

ggcatgaggc acccaccatc gctgtggccc tgctggccgc cctgggcttc ctcagcaccc   1740

tggccatcct ggtgatattc tggaggcact tccagacacc catagttcgc tcggctgggg   1800

gccccatgtg cttcctgatg ctgacactgc tgctggtggc atacatggtg gtcccggtgt   1860

acgtggggcc gcccaaggtc tccacctgcc tctgccgcca ggccctcttt cccctctgct   1920
```

-continued tcacaatttg catctcctgt atcgccgtgc gttctttcca gatcgtctgc gccttcaaga 1980
tggccagccg cttcccacgc gcctacagct actgggtccg ctaccagggg ccctacgtct 2040
ctatggcatt tatcacggta ctcaaaatgg tcattgtggt aattggcatg ctggccacgg 2100
gcctcagtcc caccacccgt actgaccccg atgaccccaa gatcacaatt gtctcctgta 2160
accccaacta ccgcaacagc ctgctgttca acaccagcct ggacctgctg ctctcagtgg 2220
tgggtttcag cttcgcctac atgggcaaag agctgcccac caactacaac gaggccaagt 2280
tcatcaccct cagcatgacc ttctatttca cctcatccgt ctccctctgc accttcatgt 2340
ctgcctacag cggggtgctg gtcaccatcg tggacctctt ggtcactgtg ctcaacctcc 2400
tggccatcag cctgggctac ttcggcccca agtgctacat gatcctcttc tacccggagc 2460
gcaacacgcc cgcctacttc aacagcatga tccagggcta caccatgagg agggactag 2519

<210> SEQ ID NO 11
<211> LENGTH: 2577
<212> TYPE: DNA
<213> ORGANISM: Rattus sp.

<400> SEQUENCE: 11
atgccgggtt tggctatctt gggcctcagt ctggctgctt tcctggagct tgggatgggg 60
tcctctttgt gtctgtcaca gcaattcaag gcacaagggg actatatatt gggtggacta 120
tttcccctgg gcacaactga ggaggccact ctcaaccaga gaacacagcc caacggcatc 180
ctatgtacca ggttctcgcc ccttggtttg ttcctggcca tggctatgaa gatggctgta 240
gaggagatca acaatggatc tgccttgctc cctgggctgc gactgggcta tgacctgttt 300
gacacatgct cagagccagt ggtcaccatg aagcccagcc tcatgttcat ggccaaggtg 360
ggaagtcaaa gcattgctgc ctactgcaac tacacacagt accaaccccg tgtgctggct 420
gtcattggtc cccactcatc agagcttgcc ctcattacag gcaagttctt cagcttcttc 480
ctcatgccac aggtcagcta tagtgccagc atggatcggc taagtgaccg ggaaacattt 540
ccatccttct tccgcacagt gcccagtgac cgggtgcagc tgcaggccgt tgtgacactg 600
ttgcagaatt tcagctggaa ctgggtggct gccttaggta gtgatgatga ctatggccgg 660
gaaggtctga gcatcttttc tggtctggcc aactcacgag gtatctgcat tgcacacgag 720
ggcctggtgc cacaacatga cactagtggc caacaattgg gcaaggtggt ggatgtgcta 780
cgccaagtga accaaagcaa agtacaggtg gtggtgctgt ttgcatctgc ccgtgctgtc 840
tactcccttt ttagctacag catccttcat gacctctcac ccaaggtatg ggtggccagt 900
gagtcctggc tgacctctga cctggtcatg acacttccca atattgcccg tgtgggcact 960
gttcttgggt ttctgcagcg cggtgcccta ctgcctgaat ttcccattta tgtggagact 1020
cgccttgccc tagctgctga cccaacattc tgtgcctccc tgaaagctga gttggatctg 1080
gaggagcgcg tgatggggcc acgctgttca caatgtgact acatcatgct acagaacctg 1140
tcatctgggc tgatgcagaa cctatcagct gggcagttgc accaccaaat atttgcaacc 1200
tatgcagctg tgtacagtgt ggctcaggcc cttcacaaca ccctgcagtg caatgtctca 1260
cattgccaca catcagagcc tgttcaaccc tggcagctcc tggagaacat gtacaatatg 1320
agtttccgtg ctcgagactt gacactgcag tttgatgcca aagggagtgt agacatggaa 1380
tatgacctga agatgtgggt gtggcagagc cctacacctg tactacatac tgtaggcacc 1440
ttcaacggca cccttcagct gcagcactcg aaaatgtatt ggccaggcaa ccaggtgcca 1500
gtctcccagt gctcccggca gtgcaaagat ggccaggtgc gcagagtaaa gggctttcat 1560

-continued

```
tcctgctgct atgactgtgt ggactgcaag gcagggagct accggaagca tccagatgac   1620

ttcacctgta ctccatgtgg caaggatcag tggtccccag aaaaaagcac aacctgctta   1680

cctcgcaggc ccaagtttct ggcttggggg gagccagctg tgctgtcact tctcctgctg   1740

ctttgcctgg tgctgggcct gacactggct gccctggggc tctttgtcca ctactgggac   1800

agccctcttg ttcaggcctc aggtgggtca ctgttctgct ttggcctgat ctgcctaggc   1860

ctcttctgcc tcagtgtcct tctgttccca ggacgaccac gctctgccag ctgccttgcc   1920

caacaaccaa tggctcacct ccctctcaca ggctgcctga gcacactctt cctgcaagca   1980

gccgagatct ttgtggagtc tgagctgcca ctgagttggg caaactggct ctgcagctac   2040

cttcggggcc cctgggcttg gctggtggta ctgctggcca ctcttgtgga ggctgcacta   2100

tgtgcctggt acttgatggc tttccctcca gaggtggtga cagattggca ggtgctgccc   2160

acggaggtac tggaacactg ccgcatgcgt tcctgggtca gcctgggctt ggtgcacatc   2220

accaatgcag tgttagcttt cctctgcttt ctgggcactt tcctggtaca gagccagcct   2280

ggtcgctata accgtgcccg tggcctcacc ttcgccatgc tagcttattt catcatctgg   2340

gtctcttttg tgcccctcct ggctaatgtg caggtggcct accagccagc tgtgcagatg   2400

ggtgctatct tattctgtgc cctgggcatc ctggccacct tccacctgcc caaatgctat   2460

gtacttctgt ggctgccaga gctcaacacc caggagttct tcctgggaag gagccccaag   2520

gaagcatcag atgggaatag tggtagtagt gaggcaactc ggggacacag tgaatga      2577
```

<210> SEQ ID NO 12
<211> LENGTH: 137
<212> TYPE: PRT
<213> ORGANISM: Fugu rubripes

<400> SEQUENCE: 12

```
Pro Ser Pro Phe Arg Asp Ile Val Ser Tyr Pro Asp Lys Ile Ile Leu
  1               5                  10                  15

Gly Cys Phe Met Asn Leu Lys Thr Ser Ser Val Ser Phe Val Leu Leu
             20                  25                  30

Leu Leu Leu Cys Leu Leu Cys Phe Ile Phe Ser Tyr Met Gly Lys Asp
         35                  40                  45

Leu Pro Lys Asn Tyr Asn Glu Ala Lys Ala Ile Thr Phe Cys Leu Leu
     50                  55                  60

Leu Leu Ile Leu Thr Trp Ile Ile Phe Thr Thr Ala Ser Leu Leu Tyr
 65                  70                  75                  80

Gln Gly Lys Tyr Ile His Ser Leu Asn Ala Leu Ala Val Leu Ser Ser
                 85                  90                  95

Ile Tyr Ser Phe Leu Leu Trp Tyr Phe Leu Pro Lys Cys Tyr Ile Ile
            100                 105                 110

Ile Phe Gln Pro Gln Lys Asn Thr Gln Lys Tyr Phe Gln Gly Leu Ile
        115                 120                 125

Gln Asp Tyr Thr Lys Thr Ile Ser Gln
    130                 135
```

<210> SEQ ID NO 13
<211> LENGTH: 242
<212> TYPE: PRT
<213> ORGANISM: Tetraodon cutcutia
<220> FEATURE:
<221> NAME/KEY: MOD_RES
<222> LOCATION: (120)..(121)
<223> OTHER INFORMATION: Any amino acid

<400> SEQUENCE: 13

```
Phe Ala Val Asn Tyr Asn Thr Pro Val Val Arg Ser Ala Gly Gly Pro
  1               5                  10                  15

Met Cys Phe Leu Ile Leu Gly Cys Leu Ser Leu Cys Ser Ile Ser Val
             20                  25                  30

Phe Phe Tyr Phe Glu Arg Pro Thr Glu Ala Phe Cys Ile Leu Arg Phe
         35                  40                  45

Met Pro Phe Leu Leu Phe Tyr Ala Val Cys Leu Ala Cys Phe Ala Val
     50                  55                  60

Arg Ser Phe Gln Ile Val Ile Ile Phe Lys Ile Ala Ala Lys Phe Pro
 65                  70                  75                  80

Arg Val His Ser Trp Trp Met Lys Tyr His Gly Gln Trp Leu Val Ile
                 85                  90                  95

Ser Met Thr Phe Val Leu Gln Ala Val Val Ile Val Ile Gly Phe Ser
            100                 105                 110

Ser Asn Pro Pro Leu Pro Tyr Xaa Xaa Phe Val Ser Tyr Pro Asp Lys
        115                 120                 125

Ile Ile Leu Gly Cys Asp Val Asn Leu Asn Met Ala Ser Thr Ser Phe
    130                 135                 140

Phe Leu Leu Leu Leu Leu Cys Ile Leu Cys Phe Thr Phe Ser Tyr Met
145                 150                 155                 160

Gly Lys Asp Leu Pro Lys Asn Tyr Asn Glu Ala Lys Ala Ile Thr Phe
                165                 170                 175

Cys Leu Leu Leu Leu Ile Leu Thr Trp Ile Ile Phe Ala Thr Ala Phe
            180                 185                 190

Met Leu Tyr His Gly Lys Tyr Ile His Thr Leu Asn Ala Leu Ala Val
        195                 200                 205

Leu Ser Ser Ala Tyr Cys Phe Leu Leu Trp Tyr Phe Leu Pro Lys Cys
    210                 215                 220

Tyr Ile Ile Ile Phe Gln Pro His Lys Asn Thr Gln Lys Tyr Phe Gln
225                 230                 235                 240

Leu Ser
```

<210> SEQ ID NO 14
<211> LENGTH: 165
<212> TYPE: PRT
<213> ORGANISM: Fugu rubripes

<400> SEQUENCE: 14

```
Lys Lys Gln Gly Pro Glu Val Asp Ile Phe Ile Val Ser Val Thr Ile
  1               5                  10                  15

Leu Cys Ile Ser Val Leu Gly Val Ala Val Gly Pro Pro Glu Pro Ser
             20                  25                  30

Gln Asp Leu Asp Phe Tyr Met Asp Ser Ile Val Leu Glu Cys Ser Asn
         35                  40                  45

Thr Leu Ser Pro Gly Ser Phe Ile Glu Leu Cys Tyr Val Cys Val Leu
     50                  55                  60

Ser Val Leu Cys Phe Phe Phe Ser Tyr Met Gly Lys Asp Leu Pro Ala
 65                  70                  75                  80

Asn Tyr Asn Glu Ala Lys Cys Val Thr Phe Ser Leu Met Val Tyr Met
                 85                  90                  95

Ile Ser Trp Ile Ser Phe Phe Thr Val Tyr Leu Ile Ser Arg Gly Pro
            100                 105                 110
```

```
Phe Thr Val Ala Ala Tyr Val Cys Ala Thr Leu Val Ser Val Leu Ala
        115                 120                 125

Phe Phe Gly Gly Tyr Phe Leu Pro Lys Ile Tyr Ile Ile Val Leu Lys
    130                 135                 140

Pro Gln Met Asn Thr Thr Ala His Phe Gln Asn Cys Ile Gln Met Tyr
145                 150                 155                 160

Thr Met Ser Lys Gln
                165


<210> SEQ ID NO 15
<211> LENGTH: 236
<212> TYPE: PRT
<213> ORGANISM: Tetraodon cutcutia
<220> FEATURE:
<221> NAME/KEY: MOD_RES
<222> LOCATION: (8)
<223> OTHER INFORMATION: Any amino acid
<220> FEATURE:
<221> NAME/KEY: MOD_RES
<222> LOCATION: (15)
<223> OTHER INFORMATION: Any amino acid
<220> FEATURE:
<221> NAME/KEY: MOD_RES
<222> LOCATION: (59)
<223> OTHER INFORMATION: Any amino acid
<220> FEATURE:
<221> NAME/KEY: MOD_RES
<222> LOCATION: (62)
<223> OTHER INFORMATION: Any amino acid
<220> FEATURE:
<221> NAME/KEY: MOD_RES
<222> LOCATION: (76)
<223> OTHER INFORMATION: Any amino acid
<220> FEATURE:
<221> NAME/KEY: MOD_RES
<222> LOCATION: (117)
<223> OTHER INFORMATION: Any amino acid
<220> FEATURE:
<221> NAME/KEY: MOD_RES
<222> LOCATION: (128)
<223> OTHER INFORMATION: Any amino acid
<220> FEATURE:
<221> NAME/KEY: MOD_RES
<222> LOCATION: (136)
<223> OTHER INFORMATION: Any amino acid
<220> FEATURE:
<221> NAME/KEY: MOD_RES
<222> LOCATION: (168)
<223> OTHER INFORMATION: Any amino acid
<220> FEATURE:
<221> NAME/KEY: MOD_RES
<222> LOCATION: (173)
<223> OTHER INFORMATION: Any amino acid
<220> FEATURE:
<221> NAME/KEY: MOD_RES
<222> LOCATION: (175)..(176)
<223> OTHER INFORMATION: Any amino acid
<220> FEATURE:
<221> NAME/KEY: MOD_RES
<222> LOCATION: (203)
<223> OTHER INFORMATION: Any amino acid
<220> FEATURE:
<221> NAME/KEY: MOD_RES
<222> LOCATION: (226)
<223> OTHER INFORMATION: Any amino acid

<400> SEQUENCE: 15

Ala Pro Lys Ser Ser Gln Arg Xaa Leu Arg Arg Thr Arg Leu Xaa Leu
  1               5                  10                  15

Glu Trp Asp His Pro Met Ser Val Ala Leu Leu Phe Phe Leu Val Cys
             20                  25                  30
```

-continued

```
Cys Leu Leu Met Thr Ser Ser Ser Ala Val Ile Leu Leu Leu Asn Ile
        35                  40                  45

Asn Thr Pro Val Ala Lys Ser Ala Gly Gly Xaa Thr Cys Xaa Leu Lys
    50                  55                  60

Leu Ala Ala Leu Thr Ala Ala Ala Met Ser Ser Xaa Cys His Phe Gly
65                  70                  75                  80

Gln Pro Ser Pro Leu Ala Ser Lys Leu Lys Gln Pro Gln Phe Thr Phe
                85                  90                  95

Ser Phe Thr Val Cys Leu Ala Cys Asn Arg Cys Ala Leu Ala Thr Gly
            100                 105                 110

His Leu His Phe Xaa Ile Arg Val Ala Leu Pro Pro Ala Tyr Asn Xaa
        115                 120                 125

Trp Ala Lys Asn His Gly Pro Xaa Ala Thr Ile Phe Ile Ala Ser Ala
    130                 135                 140

Ala Ile Leu Cys Val Leu Cys Leu Arg Val Ala Val Gly Pro Pro Gln
145                 150                 155                 160

Pro Ser Gln Asx Leu Asx Phe Xaa Thr Asn Ser Ile Xaa Leu Xaa Xaa
                165                 170                 175

Ser Asn Thr Leu Ser Pro Gly Ser Phe Val Glu Leu Cys Asn Val Ser
            180                 185                 190

Leu Leu Ser Ala Val Cys Phe Val Phe Ser Xaa Met Gly Lys Asx Leu
        195                 200                 205

Pro Ala Asn Tyr Asn Glu Ala Lys Cys Val Thr Phe Ser Leu Met Val
    210                 215                 220

Asn Xaa Ile Ser Trp Ile Ser Phe Phe Thr Val Tyr
225                 230                 235


<210> SEQ ID NO 16
<211> LENGTH: 840
<212> TYPE: PRT
<213> ORGANISM: Rattus sp.

<400> SEQUENCE: 16

Met Leu Phe Trp Ala Ala His Leu Leu Leu Ser Leu Gln Leu Val Tyr
  1               5                  10                  15

Cys Trp Ala Phe Ser Cys Gln Arg Thr Glu Ser Ser Pro Gly Phe Ser
            20                  25                  30

Leu Pro Gly Asp Phe Leu Leu Ala Gly Leu Phe Ser Leu His Gly Asp
        35                  40                  45

Cys Leu Gln Val Arg His Arg Pro Leu Val Thr Ser Cys Asp Arg Pro
    50                  55                  60

Asp Ser Phe Asn Gly His Gly Tyr His Leu Phe Gln Ala Met Arg Phe
65                  70                  75                  80

Thr Val Glu Glu Ile Asn Asn Ser Ser Ala Leu Leu Pro Asn Ile Thr
                85                  90                  95

Leu Gly Tyr Glu Leu Tyr Asp Val Cys Ser Glu Ser Ala Asn Val Tyr
            100                 105                 110

Ala Thr Leu Arg Val Leu Ala Leu Gln Gly Pro Arg His Ile Glu Ile
        115                 120                 125

Gln Lys Asp Leu Arg Asn His Ser Ser Lys Val Val Ala Phe Ile Gly
    130                 135                 140

Pro Asp Asn Thr Asp His Ala Val Thr Thr Ala Ala Leu Leu Gly Pro
145                 150                 155                 160

Phe Leu Met Pro Leu Val Ser Tyr Glu Ala Ser Ser Val Val Leu Ser
                165                 170                 175
```

-continued

```
Ala Lys Arg Lys Phe Pro Ser Phe Leu Arg Thr Val Pro Ser Asp Arg
            180                 185                 190

His Gln Val Glu Val Met Val Gln Leu Leu Gln Ser Phe Gly Trp Val
        195                 200                 205

Trp Ile Ser Leu Ile Gly Ser Tyr Gly Asp Tyr Gly Gln Leu Gly Val
    210                 215                 220

Gln Ala Leu Glu Glu Leu Ala Val Pro Arg Gly Ile Cys Val Ala Phe
225                 230                 235                 240

Lys Asp Ile Val Pro Phe Ser Ala Arg Val Gly Asp Pro Arg Met Gln
                245                 250                 255

Ser Met Met Gln His Leu Ala Gln Ala Arg Thr Thr Val Val Val Val
            260                 265                 270

Phe Ser Asn Arg His Leu Ala Arg Val Phe Phe Arg Ser Val Val Leu
        275                 280                 285

Ala Asn Leu Thr Gly Lys Val Trp Val Ala Ser Glu Asp Trp Ala Ile
    290                 295                 300

Ser Thr Tyr Ile Thr Ser Val Thr Gly Ile Gln Gly Ile Gly Thr Val
305                 310                 315                 320

Leu Gly Val Ala Val Gln Gln Arg Gln Val Pro Gly Leu Lys Glu Phe
                325                 330                 335

Glu Glu Ser Tyr Val Arg Ala Val Thr Ala Ala Pro Ser Ala Cys Pro
            340                 345                 350

Glu Gly Ser Trp Cys Ser Thr Asn Gln Leu Cys Arg Glu Cys His Thr
        355                 360                 365

Phe Thr Thr Arg Asn Met Pro Thr Leu Gly Ala Phe Ser Met Ser Ala
    370                 375                 380

Ala Tyr Arg Val Tyr Glu Ala Val Tyr Ala Val Ala His Gly Leu His
385                 390                 395                 400

Gln Leu Leu Gly Cys Thr Ser Glu Ile Cys Ser Arg Gly Pro Val Tyr
                405                 410                 415

Pro Trp Gln Leu Leu Gln Gln Ile Tyr Lys Val Asn Phe Leu Leu His
            420                 425                 430

Glu Asn Thr Val Ala Phe Asp Asp Asn Gly Asp Thr Leu Gly Tyr Tyr
        435                 440                 445

Asp Ile Ile Ala Trp Asp Trp Asn Gly Pro Glu Trp Thr Phe Glu Ile
    450                 455                 460

Ile Gly Ser Ala Ser Leu Ser Pro Val His Leu Asp Ile Asn Lys Thr
465                 470                 475                 480

Lys Ile Gln Trp His Gly Lys Asn Asn Gln Val Pro Val Ser Val Cys
                485                 490                 495

Thr Thr Asp Cys Leu Ala Gly His His Arg Val Val Val Gly Ser His
            500                 505                 510

His Cys Cys Phe Glu Cys Val Pro Cys Glu Ala Gly Thr Phe Leu Asn
        515                 520                 525

Met Ser Glu Leu His Ile Cys Gln Pro Cys Gly Thr Glu Glu Trp Ala
    530                 535                 540

Pro Lys Glu Ser Thr Thr Cys Phe Pro Arg Thr Val Glu Phe Leu Ala
545                 550                 555                 560

Trp His Glu Pro Ile Ser Leu Val Leu Ile Ala Ala Asn Thr Leu Leu
                565                 570                 575

Leu Leu Leu Leu Val Gly Thr Ala Gly Leu Phe Ala Trp His Phe His
            580                 585                 590
```

-continued

```
Thr Pro Val Val Arg Ser Ala Gly Gly Arg Leu Cys Phe Leu Met Leu
        595                 600                 605

Gly Ser Leu Val Ala Gly Ser Cys Ser Phe Tyr Ser Phe Phe Gly Glu
    610                 615                 620

Pro Thr Val Pro Ala Cys Leu Leu Arg Gln Pro Leu Phe Ser Leu Gly
625                 630                 635                 640

Phe Ala Ile Phe Leu Ser Cys Leu Thr Ile Arg Ser Phe Gln Leu Val
                645                 650                 655

Ile Ile Phe Lys Phe Ser Thr Lys Val Pro Thr Phe Tyr Arg Thr Trp
            660                 665                 670

Ala Gln Asn His Gly Ala Gly Leu Phe Val Ile Val Ser Ser Thr Val
        675                 680                 685

His Leu Leu Ile Cys Leu Thr Trp Leu Val Met Trp Thr Pro Arg Pro
    690                 695                 700

Thr Arg Glu Tyr Gln Arg Phe Pro His Leu Val Ile Leu Glu Cys Thr
705                 710                 715                 720

Glu Val Asn Ser Val Gly Phe Leu Leu Ala Phe Thr His Asn Ile Leu
                725                 730                 735

Leu Ser Ile Ser Thr Phe Val Cys Ser Tyr Leu Gly Lys Glu Leu Pro
            740                 745                 750

Glu Asn Tyr Asn Glu Ala Lys Cys Val Thr Phe Ser Leu Leu Leu Asn
        755                 760                 765

Phe Val Ser Trp Ile Ala Phe Phe Thr Met Ala Ser Ile Tyr Gln Gly
    770                 775                 780

Ser Tyr Leu Pro Ala Val Asn Val Leu Ala Gly Leu Thr Thr Leu Ser
785                 790                 795                 800

Gly Gly Phe Ser Gly Tyr Phe Leu Pro Lys Cys Tyr Val Ile Leu Cys
                805                 810                 815

Arg Pro Glu Leu Asn Asn Thr Glu His Phe Gln Ala Ser Ile Gln Asp
            820                 825                 830

Tyr Thr Arg Arg Cys Gly Thr Thr
        835                 840


<210> SEQ ID NO 17
<211> LENGTH: 843
<212> TYPE: PRT
<213> ORGANISM: Rattus sp.

<400> SEQUENCE: 17

Met Gly Pro Gln Ala Arg Thr Leu Cys Leu Leu Ser Leu Leu Leu His
  1               5                  10                  15

Val Leu Pro Lys Pro Gly Lys Leu Val Glu Asn Ser Asp Phe His Leu
            20                  25                  30

Ala Gly Asp Tyr Leu Leu Gly Gly Leu Phe Thr Leu His Ala Asn Val
        35                  40                  45

Lys Ser Ile Ser His Leu Ser Tyr Leu Gln Val Pro Lys Cys Asn Glu
    50                  55                  60

Phe Thr Met Lys Val Leu Gly Tyr Asn Leu Met Gln Ala Met Arg Phe
65                  70                  75                  80

Ala Val Glu Glu Ile Asn Asn Cys Ser Ser Leu Leu Pro Gly Val Leu
                85                  90                  95

Leu Gly Tyr Glu Met Val Asp Val Cys Tyr Leu Ser Asn Asn Ile His
            100                 105                 110

Pro Gly Leu Tyr Phe Leu Ala Gln Asp Asp Asp Leu Leu Pro Ile Leu
        115                 120                 125
```

-continued

```
Lys Asp Tyr Ser Gln Tyr Met Pro His Val Val Ala Val Ile Gly Pro
    130                 135                 140

Asp Asn Ser Glu Ser Ala Ile Thr Val Ser Asn Ile Leu Ser His Phe
145                 150                 155                 160

Leu Ile Pro Gln Ile Thr Tyr Ser Ala Ile Ser Asp Lys Leu Arg Asp
                165                 170                 175

Lys Arg His Phe Pro Ser Met Leu Arg Thr Val Pro Ser Ala Thr His
            180                 185                 190

His Ile Glu Ala Met Val Gln Leu Met Val His Phe Gln Trp Asn Trp
        195                 200                 205

Ile Val Val Leu Val Ser Asp Asp Asp Tyr Gly Arg Glu Asn Ser His
    210                 215                 220

Leu Leu Ser Gln Arg Leu Thr Lys Thr Ser Asp Ile Cys Ile Ala Phe
225                 230                 235                 240

Gln Glu Val Leu Pro Ile Pro Glu Ser Ser Gln Val Met Arg Ser Glu
                245                 250                 255

Glu Gln Arg Gln Leu Asp Asn Ile Leu Asp Lys Leu Arg Arg Thr Ser
            260                 265                 270

Ala Arg Val Val Val Val Phe Ser Pro Glu Leu Ser Leu Tyr Ser Phe
        275                 280                 285

Phe His Glu Val Leu Arg Trp Asn Phe Thr Gly Phe Val Trp Ile Ala
    290                 295                 300

Ser Glu Ser Trp Ala Ile Asp Pro Val Leu His Asn Leu Thr Glu Leu
305                 310                 315                 320

Arg His Thr Gly Thr Phe Leu Gly Val Thr Ile Gln Arg Val Ser Ile
                325                 330                 335

Pro Gly Phe Ser Gln Phe Arg Val Arg Arg Asp Lys Pro Gly Tyr Pro
            340                 345                 350

Val Pro Asn Thr Thr Asn Leu Arg Thr Thr Cys Asn Gln Asp Cys Asp
        355                 360                 365

Ala Cys Leu Asn Thr Thr Lys Ser Phe Asn Asn Ile Leu Ile Leu Ser
    370                 375                 380

Gly Glu Arg Val Val Tyr Ser Val Tyr Ser Ala Val Tyr Ala Val Ala
385                 390                 395                 400

His Ala Leu His Arg Leu Leu Gly Cys Asn Arg Val Arg Cys Thr Lys
                405                 410                 415

Gln Lys Val Tyr Pro Trp Gln Leu Leu Arg Glu Ile Trp His Val Asn
            420                 425                 430

Phe Thr Leu Leu Gly Asn Arg Leu Phe Phe Asp Gln Gln Gly Asp Met
        435                 440                 445

Pro Met Leu Leu Asp Ile Ile Gln Trp Gln Trp Asp Leu Ser Gln Asn
    450                 455                 460

Pro Phe Gln Ser Ile Ala Ser Tyr Ser Pro Thr Ser Lys Arg Leu Thr
465                 470                 475                 480

Tyr Ile Asn Asn Val Ser Trp Tyr Thr Pro Asn Asn Thr Val Pro Val
                485                 490                 495

Ser Met Cys Ser Lys Ser Cys Gln Pro Gly Gln Met Lys Lys Ser Val
            500                 505                 510

Gly Leu His Pro Cys Cys Phe Glu Cys Leu Asp Cys Met Pro Gly Thr
        515                 520                 525

Tyr Leu Asn Arg Ser Ala Asp Glu Phe Asn Cys Leu Ser Cys Pro Gly
    530                 535                 540
```

-continued

```
Ser Met Trp Ser Tyr Lys Asn Asp Ile Thr Cys Phe Gln Arg Arg Pro
545                 550                 555                 560

Thr Phe Leu Glu Trp His Glu Val Pro Thr Ile Val Val Ala Ile Leu
                565                 570                 575

Ala Ala Leu Gly Phe Phe Ser Thr Leu Ala Ile Leu Phe Ile Phe Trp
            580                 585                 590

Arg His Phe Gln Thr Pro Met Val Arg Ser Ala Gly Gly Pro Met Cys
        595                 600                 605

Phe Leu Met Leu Val Pro Leu Leu Leu Ala Phe Gly Met Val Pro Val
    610                 615                 620

Tyr Val Gly Pro Pro Thr Val Phe Ser Cys Phe Cys Arg Gln Ala Phe
625                 630                 635                 640

Phe Thr Val Cys Phe Ser Ile Cys Leu Ser Cys Ile Thr Val Arg Ser
                645                 650                 655

Phe Gln Ile Val Cys Val Phe Lys Met Ala Arg Arg Leu Pro Ser Ala
            660                 665                 670

Tyr Ser Phe Trp Met Arg Tyr His Gly Pro Tyr Val Phe Val Ala Phe
        675                 680                 685

Ile Thr Ala Ile Lys Val Ala Leu Val Val Gly Asn Met Leu Ala Thr
    690                 695                 700

Thr Ile Asn Pro Ile Gly Arg Thr Asp Pro Asp Asp Pro Asn Ile Met
705                 710                 715                 720

Ile Leu Ser Cys His Pro Asn Tyr Arg Asn Gly Leu Leu Phe Asn Thr
                725                 730                 735

Ser Met Asp Leu Leu Leu Ser Val Leu Gly Phe Ser Phe Ala Tyr Met
            740                 745                 750

Gly Lys Glu Leu Pro Thr Asn Tyr Asn Glu Ala Lys Phe Ile Thr Leu
        755                 760                 765

Ser Met Thr Phe Ser Phe Thr Ser Ser Ile Ser Leu Cys Thr Phe Met
    770                 775                 780

Ser Val His Asp Gly Val Leu Val Thr Ile Met Asp Leu Leu Val Thr
785                 790                 795                 800

Val Leu Asn Phe Leu Ala Ile Gly Leu Gly Tyr Phe Gly Pro Lys Cys
                805                 810                 815

Tyr Met Ile Leu Phe Tyr Pro Glu Arg Asn Thr Ser Ala Tyr Phe Asn
            820                 825                 830

Ser Met Ile Gln Gly Tyr Thr Met Arg Lys Ser
        835                 840


<210> SEQ ID NO 18
<211> LENGTH: 845
<212> TYPE: PRT
<213> ORGANISM: Rattus sp.

<400> SEQUENCE: 18

Met Val Arg Leu Leu Leu Ile Phe Phe Pro Met Ile Phe Leu Glu Met
  1               5                  10                  15

Ser Ile Leu Pro Arg Met Pro Asp Arg Lys Val Leu Leu Ala Gly Ala
             20                  25                  30

Ser Ser Gln Arg Ser Val Ala Arg Met Asp Gly Asp Val Ile Ile Gly
         35                  40                  45

Ala Leu Phe Ser Val His His Gln Pro Pro Ala Glu Lys Val Pro Glu
     50                  55                  60

Arg Lys Cys Gly Glu Ile Arg Glu Gln Tyr Gly Ile Gln Arg Val Glu
 65                  70                  75                  80
```

-continued

```
Ala Met Phe His Thr Leu Asp Lys Ile Asn Ala Asp Pro Val Leu Leu
                85                  90                  95

Pro Asn Ile Thr Leu Gly Ser Glu Ile Arg Asp Ser Cys Trp His Ser
            100                 105                 110

Ser Val Ala Leu Glu Gln Ser Ile Glu Phe Ile Arg Asp Ser Leu Ile
        115                 120                 125

Ser Ile Arg Asp Glu Lys Asp Gly Leu Asn Arg Cys Leu Pro Asp Gly
    130                 135                 140

Gln Thr Leu Pro Pro Gly Arg Thr Lys Lys Pro Ile Ala Gly Val Ile
145                 150                 155                 160

Gly Pro Gly Ser Ser Ser Val Ala Ile Gln Val Gln Asn Leu Leu Gln
                165                 170                 175

Leu Phe Asp Ile Pro Gln Ile Ala Tyr Ser Ala Thr Ser Ile Asp Leu
            180                 185                 190

Ser Asp Lys Thr Leu Tyr Lys Tyr Phe Leu Arg Val Val Pro Ser Asp
        195                 200                 205

Thr Leu Gln Ala Arg Ala Met Leu Asp Ile Val Lys Arg Tyr Asn Trp
    210                 215                 220

Thr Tyr Val Ser Ala Val His Thr Glu Gly Asn Tyr Gly Glu Ser Gly
225                 230                 235                 240

Met Asp Ala Phe Lys Glu Leu Ala Ala Gln Glu Gly Leu Cys Ile Ala
                245                 250                 255

His Ser Asp Lys Ile Tyr Ser Asn Ala Gly Glu Lys Ser Phe Asp Arg
            260                 265                 270

Leu Leu Arg Lys Leu Arg Glu Arg Leu Pro Lys Ala Arg Val Val Val
        275                 280                 285

Cys Phe Cys Glu Gly Met Thr Val Arg Gly Leu Leu Ser Ala Met Arg
    290                 295                 300

Arg Leu Gly Val Val Gly Glu Phe Ser Leu Ile Gly Ser Asp Gly Trp
305                 310                 315                 320

Ala Asp Arg Asp Glu Val Ile Glu Gly Tyr Glu Val Glu Ala Asn Gly
                325                 330                 335

Gly Ile Thr Ile Lys Leu Gln Ser Pro Glu Val Arg Ser Phe Asp Asp
            340                 345                 350

Tyr Phe Leu Lys Leu Arg Leu Asp Thr Asn Thr Arg Asn Pro Trp Phe
        355                 360                 365

Pro Glu Phe Trp Gln His Arg Phe Gln Cys Arg Leu Pro Gly His Leu
    370                 375                 380

Leu Glu Asn Pro Asn Phe Lys Lys Val Cys Thr Gly Asn Glu Ser Leu
385                 390                 395                 400

Glu Glu Asn Tyr Val Gln Asp Ser Lys Met Gly Phe Val Ile Asn Ala
                405                 410                 415

Ile Tyr Ala Met Ala His Gly Leu Gln Asn Met His His Ala Leu Cys
            420                 425                 430

Pro Gly His Val Gly Leu Cys Asp Ala Met Lys Pro Ile Asp Gly Arg
        435                 440                 445

Lys Leu Leu Asp Phe Leu Ile Lys Ser Ser Phe Val Gly Val Ser Gly
    450                 455                 460

Glu Glu Val Trp Phe Asp Glu Lys Gly Asp Ala Pro Gly Arg Tyr Asp
465                 470                 475                 480

Ile Met Asn Leu Gln Tyr Thr Glu Ala Asn Arg Tyr Asp Tyr Val His
                485                 490                 495
```

-continued

```
Val Gly Thr Trp His Glu Gly Val Leu Asn Ile Asp Asp Tyr Lys Ile
            500                 505                 510

Gln Met Asn Lys Ser Gly Met Val Arg Ser Val Cys Ser Glu Pro Cys
        515                 520                 525

Leu Lys Gly Gln Ile Lys Val Ile Arg Lys Gly Glu Val Ser Cys Cys
    530                 535                 540

Trp Ile Cys Thr Ala Cys Lys Glu Asn Glu Phe Val Gln Asp Glu Phe
545                 550                 555                 560

Thr Cys Arg Ala Cys Asp Leu Gly Trp Trp Pro Asn Ala Glu Leu Thr
                565                 570                 575

Gly Cys Glu Pro Ile Pro Val Arg Tyr Leu Glu Trp Ser Asp Ile Glu
            580                 585                 590

Ser Ile Ile Ala Ile Ala Phe Ser Cys Leu Gly Ile Leu Val Thr Leu
        595                 600                 605

Phe Val Thr Leu Ile Phe Val Leu Tyr Arg Asp Thr Pro Val Val Lys
    610                 615                 620

Ser Ser Ser Arg Glu Leu Cys Tyr Ile Ile Leu Ala Gly Ile Phe Leu
625                 630                 635                 640

Gly Tyr Val Cys Pro Phe Thr Leu Ile Ala Lys Pro Thr Thr Thr Ser
                645                 650                 655

Cys Tyr Leu Gln Arg Leu Leu Val Gly Leu Ser Ser Ala Met Cys Tyr
            660                 665                 670

Ser Ala Leu Val Thr Lys Thr Asn Arg Ile Ala Arg Ile Leu Ala Gly
        675                 680                 685

Ser Lys Lys Lys Ile Cys Thr Arg Lys Pro Arg Phe Met Ser Ala Trp
    690                 695                 700

Ala Gln Val Ile Ile Ala Ser Ile Leu Ile Ser Val Gln Leu Thr Leu
705                 710                 715                 720

Val Val Thr Leu Ile Ile Met Glu Pro Pro Met Pro Ile Leu Ser Tyr
                725                 730                 735

Pro Ser Ile Lys Glu Val Tyr Leu Ile Cys Asn Thr Ser Asn Leu Gly
            740                 745                 750

Val Val Ala Pro Val Gly Tyr Asn Gly Leu Leu Ile Met Ser Cys Thr
        755                 760                 765

Tyr Tyr Ala Phe Lys Thr Arg Asn Val Pro Ala Asn Phe Asn Glu Ala
    770                 775                 780

Lys Tyr Ile Ala Phe Thr Met Tyr Thr Thr Cys Ile Ile Trp Leu Ala
785                 790                 795                 800

Phe Val Pro Ile Tyr Phe Gly Ser Asn Tyr Lys Ile Ile Thr Thr Cys
                805                 810                 815

Phe Ala Val Ser Leu Ser Val Thr Val Ala Leu Gly Cys Met Phe Thr
            820                 825                 830

Pro Lys Met Tyr Ile Ile Ile Ala Lys Pro Glu Arg Asn
        835                 840                 845


<210> SEQ ID NO 19
<211> LENGTH: 867
<212> TYPE: PRT
<213> ORGANISM: Homo sapiens

<400> SEQUENCE: 19

Met Ala Phe Tyr Ser Cys Cys Trp Val Leu Leu Ala Leu Thr Trp His
  1               5                  10                  15

Thr Ser Ala Tyr Gly Pro Asp Gln Arg Ala Gln Lys Lys Gly Asp Ile
            20                  25                  30
```

```
Ile Leu Gly Gly Leu Phe Pro Ile His Phe Gly Val Ala Ala Lys Asp
        35                  40                  45

Gln Asp Leu Lys Ser Arg Pro Glu Ser Val Glu Cys Ile Arg Tyr Asn
    50                  55                  60

Phe Arg Gly Phe Arg Trp Leu Gln Ala Met Ile Phe Ala Ile Glu Glu
65                  70                  75                  80

Ile Asn Ser Ser Pro Ala Leu Leu Pro Asn Leu Thr Leu Gly Tyr Arg
                85                  90                  95

Ile Phe Asp Thr Cys Asn Thr Val Ser Lys Ala Leu Glu Ala Thr Leu
            100                 105                 110

Ser Phe Val Ala Gln Asn Lys Ile Asp Ser Leu Asn Leu Asp Glu Phe
        115                 120                 125

Cys Asn Cys Ser Glu His Ile Pro Ser Thr Ile Ala Val Val Gly Ala
    130                 135                 140

Thr Gly Ser Gly Val Ser Thr Ala Val Ala Asn Leu Leu Gly Leu Phe
145                 150                 155                 160

Tyr Ile Pro Gln Val Ser Tyr Ala Ser Ser Ser Arg Leu Leu Ser Asn
                165                 170                 175

Lys Asn Gln Phe Lys Ser Phe Leu Arg Thr Ile Pro Asn Asp Glu His
            180                 185                 190

Gln Ala Thr Ala Met Ala Asp Ile Ile Glu Tyr Phe Arg Trp Asn Trp
        195                 200                 205

Val Gly Thr Ile Ala Ala Asp Asp Asp Tyr Gly Arg Pro Gly Ile Glu
    210                 215                 220

Lys Phe Arg Glu Glu Ala Glu Glu Arg Asp Ile Cys Ile Asp Phe Ser
225                 230                 235                 240

Glu Leu Ile Ser Gln Tyr Ser Asp Glu Glu Glu Ile Gln His Val Val
                245                 250                 255

Glu Val Ile Gln Asn Ser Thr Ala Lys Val Ile Val Val Phe Ser Ser
            260                 265                 270

Gly Pro Asp Leu Glu Pro Leu Ile Lys Glu Ile Val Arg Arg Asn Ile
        275                 280                 285

Thr Gly Lys Ile Trp Leu Ala Ser Glu Ala Trp Ala Ser Ser Ser Leu
    290                 295                 300

Ile Ala Met Pro Gln Tyr Phe His Val Val Gly Gly Thr Ile Gly Phe
305                 310                 315                 320

Ala Leu Lys Ala Gly Gln Ile Pro Gly Phe Arg Glu Phe Leu Lys Lys
                325                 330                 335

Val His Pro Arg Lys Ser Val His Asn Gly Phe Ala Lys Glu Phe Trp
            340                 345                 350

Glu Glu Thr Phe Asn Cys His Leu Gln Glu Gly Ala Lys Gly Pro Leu
        355                 360                 365

Pro Val Asp Thr Phe Leu Arg Gly His Glu Glu Ser Gly Asp Arg Phe
    370                 375                 380

Ser Asn Ser Ser Thr Ala Phe Arg Pro Leu Cys Thr Gly Asp Glu Asn
385                 390                 395                 400

Ile Ser Ser Val Glu Thr Pro Tyr Ile Asp Tyr Thr His Leu Arg Ile
                405                 410                 415

Ser Tyr Asn Val Tyr Leu Ala Val Tyr Ser Ile Ala His Ala Leu Gln
            420                 425                 430

Asp Ile Tyr Thr Cys Leu Pro Gly Arg Gly Leu Phe Thr Asn Gly Ser
        435                 440                 445
```

-continued

```
Cys Ala Asp Ile Lys Lys Val Glu Ala Trp Gln Val Leu Lys His Leu
    450                 455                 460

Arg His Leu Asn Phe Thr Asn Asn Met Gly Glu Gln Val Thr Phe Asp
465                 470                 475                 480

Glu Cys Gly Asp Leu Val Gly Asn Tyr Ser Ile Ile Asn Trp His Leu
                485                 490                 495

Ser Pro Glu Asp Gly Ser Ile Val Phe Lys Glu Val Gly Tyr Tyr Asn
            500                 505                 510

Val Tyr Ala Lys Lys Gly Glu Arg Leu Phe Ile Asn Glu Glu Lys Ile
        515                 520                 525

Leu Trp Ser Gly Phe Ser Arg Glu Val Pro Phe Ser Asn Cys Ser Arg
    530                 535                 540

Asp Cys Leu Ala Gly Thr Arg Lys Gly Ile Ile Glu Gly Glu Pro Thr
545                 550                 555                 560

Cys Cys Phe Glu Cys Val Glu Cys Pro Asp Gly Glu Tyr Ser Asp Glu
                565                 570                 575

Thr Asp Ala Ser Ala Cys Asn Lys Cys Pro Asp Asp Phe Trp Ser Asn
            580                 585                 590

Glu Asn His Thr Ser Cys Ile Ala Lys Glu Ile Glu Phe Leu Ser Trp
        595                 600                 605

Thr Glu Pro Phe Gly Ile Ala Leu Thr Leu Phe Ala Val Leu Gly Ile
    610                 615                 620

Phe Leu Thr Ala Phe Val Leu Gly Val Phe Ile Lys Phe Arg Asn Thr
625                 630                 635                 640

Pro Ile Val Lys Ala Thr Asn Arg Glu Leu Ser Tyr Leu Leu Leu Phe
                645                 650                 655

Ser Leu Leu Cys Cys Phe Ser Ser Ser Leu Phe Phe Ile Gly Glu Pro
            660                 665                 670

Gln Asp Trp Thr Cys Arg Leu Arg Gln Pro Ala Phe Gly Ile Ser Phe
        675                 680                 685

Val Leu Cys Ile Ser Cys Ile Leu Val Lys Thr Asn Arg Val Leu Leu
    690                 695                 700

Val Phe Glu Ala Lys Ile Pro Thr Ser Phe His Arg Lys Trp Trp Gly
705                 710                 715                 720

Leu Asn Leu Gln Phe Leu Leu Val Phe Leu Cys Thr Phe Met Gln Ile
                725                 730                 735

Val Ile Cys Val Ile Trp Leu Tyr Thr Ala Pro Pro Ser Ser Tyr Arg
            740                 745                 750

Asn Gln Glu Leu Glu Asp Glu Ile Ile Phe Ile Thr Cys His Glu Gly
        755                 760                 765

Ser Leu Met Ala Leu Gly Phe Leu Ile Gly Tyr Thr Cys Leu Leu Ala
    770                 775                 780

Ala Ile Cys Phe Phe Phe Ala Phe Lys Ser Arg Lys Leu Pro Glu Asn
785                 790                 795                 800

Phe Asn Glu Ala Lys Phe Ile Thr Phe Ser Met Leu Ile Phe Phe Ile
                805                 810                 815

Val Trp Ile Ser Phe Ile Pro Ala Tyr Ala Ser Thr Tyr Gly Lys Phe
            820                 825                 830

Val Ser Ala Val Glu Val Ile Ala Ile Leu Ala Ala Ser Phe Gly Leu
        835                 840                 845
```

-continued

```
Leu Ala Cys Ile Phe Phe Asn Lys Ile Tyr Ile Ile Leu Phe Lys Pro
    850                 855                 860

Ser Arg Asn
865
```

HETEROMERIC UMAMI T1R1/T1R3 TASTE RECEPTORS AND ISOLATED CELLS THAT EXPRESS SAME

CROSS REFERENCE TO RELATED APPLICATIONS

This application is a Continuation-in-part of U.S. Nonprovisional Application Ser. No. 09/897,427, filed on Jul. 3, 2001, now U.S. Pat. No. 6,955,887; U.S. Nonprovisional Application Ser. No. 09/799,629, filed on Jul. 3, 2001, now U.S. Pat. No. 7,244,835; and U.S. Nonprovisional Application Ser. No. 10/035,045 filed Jan. 3, 2002, now U.S. Pat. No. 7,241,880; and claims the benefit under 35 U.S.C. § 119(e) to U.S. Provisional Application Ser. No 60/300,434, filed on Jun. 26, 2001; U.S. Provisional Application Ser. No. 60/304,749, filed on Jul. 13, 2001; U.S. Provisional Application Ser. No. 60/310,493, filed Aug. 8, 2001; U.S. Provisional Application Ser. No. 60/331,771, filed on Nov. 21, 2001; U.S. Provisional Application Ser. No. 60/339,472, filed Dec. 14, 2001; U.S. Provisional Application Ser. No. 60/372,090, filed Apr. 15, 2002; and U.S. Provisional Application Ser. No. 60/374,143, filed on Apr. 22, 2002; all of which are incorporated by reference in their entirety.

BACKGROUND OF THE INVENTION

1. Field of the Invention

The present invention in part relates to the discovery that the T1R receptors assemble to form functional taste receptors. Particularly, it has been discovered that co-expression of T1R1 and T1R3 results in a taste receptor that responds to umami taste stimuli, including monosodium glutamate. Also, it has been discovered that co-expression of the T1R2 and T1R3 receptors results in a taste receptor that responds to sweet taste stimuli including naturally occurring and artificial sweeteners.

Also the present invention relates to the use of hetero-oligomeric taste receptors comprising T1R1/T1R3 and T1R2/T1 R3 in assays to identify compounds that respectively respond to umami taste stimuli and sweet taste stimuli.

Further, the invention relates to the construction of cell lines that stably or transiently co-express a combination of T1R1 and T1R3; or T1R2 and T1R3; under constitutive or inducible conditions.

The use of these cell lines in cell-based assays to identify umami and sweet taste modulatory compounds is also provided, particularly high throughput screening assays that detect receptor activity by the use of fluorometric imaging.

2. Description of the Related Art

The taste system provides sensory information about the chemical composition of the external world. Mammals are believed to have at least five taste modalities: sweet, bitter, sour, salty, and umami. See, e.g., Kawamura et al., *Introduction to Umami: A Basic Taste* (1987); Kinnamon et al., *Ann. Rev. Physiol.,* 54:715-731 (1992); Lindemann et al., Physiol. Rev., 76:718-766 (1996); Stewart et al., *Am. J. Physiol.,* 272:1-26 (1997). Each taste modality is thought to be mediated by a distinct protein receptor or receptors that are expressed in taste receptor cells found on the surface of the tongue (Lindemann Physiol. Rev. 76:718-766 (1996)). The taste receptors that recognize bitter, sweet and umami taste stimuli belong to the G-protein-coupled receptor (GPCR) superfamily (Hoon et al., *Cell* 96:541 (1999); Adler et al., *Cell* 100:693 (2000)). (Other taste modalities are believed to be mediated by ion channels.)

G protein-coupled receptors mediate many other physiological functions, such as endocrine function, exocrine function, heart rate, lipolysis, and carbohydrate metabolism. The biochemical analysis and molecular cloning of a number of such receptors has revealed many basic principles regarding the function of these receptors. For example, U.S. Pat. No. 5,691,188 describes how upon a ligand binding to a GPCR, the receptor undergoes a conformational change leading to activation of a heterotrimeric G protein by promoting the displacement of bound GDP by GTP on the surface of the Gα subunit and subsequent dissociation of the Gα subunit from the Gβ and Gγ subunits. The free Gα subunits and Gβγ complexes activate downstream elements of a variety of signal transduction pathways.

This invention relates to the three-member T1R class of taste-specific GPCRs. Previously, the T1R receptors were hypothesized to function as sweet taste receptors (Hoon et al., *Cell* 96:541-51(1999); Kitagawa et al., *Biochem Biophys Res. Commun.* 283:236-42 (2001); Max et al., *Nat. Genet.* 28:58-63 (2001); Montmayeur et al., *Nat. Neurosci.* 4:412-8 (2001); Sainz et al., *J. Neurochem.* 77: 896-903 (2001)), and Nelson et al. (2001) have recently demonstrated that rat T1R2 and T1R3 act in combination to recognize sweet taste stimuli. The present invention relates to two discoveries. First, as is the case for rat T1R2/T1R3, human T1R2 and T1R3 act in combination to recognize sweet taste stimuli. Second, human T1R1 and T1R3 act in combination to recognize umami taste stimuli. Therefore, T1R2/T1R3 is likely to function as a sweet taste receptor and T1R1/T1R3 is likely to function as an umami taste receptor in mammals. The likely explanation for the functional co-dependence of T1R1 and T1R3 and the function co-dependence of T1R2 and T1R3 is that, like the structurally related $GABA_B$ receptor (Jones et al., *Nature* 396: 5316-22 (1998); Kaupmann et al., *Nature* 396: 683-7 (1998); White et al., *Nature* 396:679-82 (1998); Kuner et al., *Science* 283: 74-77 (1999)), T1Rs function as heterodimeric complexes. However, it is alternatively possible that this functional co-dependence reflects a necessary but transient interaction that ultimately produces functionally independent monomeric or homomultimeric taste receptors.

The identification of characterization of taste receptors which function as sweet and umami receptors is significant as it will facilitate the use of these receptors in assays for identifying compounds that modulate (enhance or block) sweet and umami taste. These compounds would be useful for improving the taste and palatability of foods, beverages, medicinals for human or animal consumption. Particularly, an assay that utilizes a functional sweet receptor would allow the identification of novel sweeteners.

SUMMARY OF THE INVENTION

The present invention relates to the discovery that different combinations of T1 Rs, when co-expressed, produce functional taste receptors that respond to taste stimuli. Particularly, the present invention relates to the discovery that co-expression of T1R2 and T1R3 results in a hetero-oligomeric taste receptor that responds to sweet taste stimuli. Also, the present invention relates to the discovery that the co-expression of T1R1 and T1R3 results in a hetero-oligomeric taste receptor that responds to umami taste stimuli such as monosodium glutamate.

The present invention also relates to cell lines that co-express T1R1 and T1R3, preferably human, or T1R2 and TI R3, preferably human. In preferred embodiments these cell lines will express elevated amounts of the receptors, either constitutively or inducibly. These cell lines include cells that transiently or stably express T1R1 and T1R3 or T1R2 and T1R3.

Also, the present invention provides assays, preferably high throughput screening assays, that utilize the T1R2/T1R3 taste receptor, or the T1R2/T1R3 receptor, preferably high throughput cell-based assays, to identify compounds that modulate sweet or umami taste. The invention also provides assays that include taste tests to confirm that these compounds modulate sweet or umami taste.

OBJECTIONS OF THE INVENTION

Toward that end, it is an object of the invention to provide a family of mammalian G protein-coupled receptors, herein referred to as T1Rs, that mediate taste perception.

It is another object of the invention to provide fragments and variants of such T1Rs that retain activity, e.g., that are activated by and/or bind sweet or umami taste stimuli.

It is yet another object of the invention to provide nucleic acid sequences or molecules that encode such T1Rs, fragments, or variants thereof.

It is still another object of the invention to provide expression vectors that include nucleic acid sequences that encode such T1Rs, or fragments or variants thereof, which are operably linked to at least one regulatory sequence such as a promoter, enhancer, or other sequence involved in positive or negative gene transcription and/or translation, and/or protein export.

It is still another object of the invention to provide human or non-human cells, e.g., mammalian, yeast, worm, or insect cells, that functionally express at least one of such T1Rs, or fragments or variants thereof and preferably a combination of T1Rs or fragments or variants thereof.

It is still another object of the invention to provide T1R fusion proteins or polypeptides which include at least a fragment of at least one of such T1Rs.

It is another object of the invention to provide an isolated nucleic acid molecule encoding a T1R polypeptide comprising a nucleic acid sequence that is at least 50%, preferably 75%, 85%, 90%, 95%, 96%, 97%, 98%, or 99% identical to a nucleic acid sequence having one of the hT1R nucleic acid sequences identified infra, and conservatively modified variants thereof.

It is a further object of the invention to provide an isolated nucleic acid molecule comprising a nucleic acid sequence that encodes a polypeptide having an amino acid sequence at least 35 to 50%, and preferably 60%, 75%, 85%, 90%, 95%, 96%, 97%, 98%, or 99% identical to an amino acid sequence selected from the group of one of the TIR amino acid sequences identified infra and conservatively modified variants thereof, wherein the fragment is at least 20, preferably 40, 60, 80, 100, 150, 200, or 250 amino acids in length. Optionally, the fragment can be an antigenic fragment that binds to an anti-T1R antibody.

It is still a further object of the invention to provide an isolated polypeptide comprising a variant of said fragment, wherein there is a variation in at most 10, preferably 5, 4, 3, 2, or 1 amino acid residues.

It is another object of the invention to provide T1R1/T1R3 combinations wherein T1R1 and/or T1R3 is a variant or fragment, and T1R2/T1R3 combinations wherein T1R2 and/or T1R3 is a variant or fragment.

It is still another object of the invention to provide agonists or antagonists of such T1Rs, or fragments or variants thereof.

It is still another object of the invention to provide a PDZ domain-interacting peptide (herein referred to as PDZIP) which can facilitate surface expression of integral plasma membrane proteins, specifically GPCRs such as the T1Rs. It is also an object of the invention to provide vectors including PDZIP, host cells expressing such vectors, and methods of using PDZIP to facilitate surface expression.

It is a preferred object of the invention to provide assays, especially high-throughput assays, for identifying taste-modulating compounds, particularly sweet taste and umami taste modulating compounds. Preferably, such assays will utilize a combination of T1Rs, or fragments or variants thereof, or genes encoding such T1Rs, or fragments or variants thereof, which are disclosed herein. Most preferably such combinations will comprise hT1R1/hT1R3 and hT1R2/hT1R3.

It is an especially preferred embodiment of the invention to identify compounds that modulate the T1R1/T1R3 or T1R2/T1R3 taste receptors, e.g., which enhance the ability of these receptors to respond to taste stimuli. For example, as described infra, it has been discovered that 5'-IMP or 5'-GMP enhances the responsiveness of the umami (T1R1/T1R3) to L-glutamate. These modulatory compounds may enhance the activity of different sweet or umami taste stimuli, and provide for enhanced tastes and/or for the same taste to be elicited at reduced concentration of the particular sweet or umami taste eliciting compound the activity of which is enhanced by a taste modulator identified using the subject assays.

It is still a further object of the invention to provide preferred assays for evaluating one or more compounds for a taste comprising: a step of contacting said one or more compounds with at least one of the disclosed T1Rs, fragments or variants thereof, preferably combinations of human T1Rs.

It is a more specific object of the invention to provide a method of screening one or more compounds for their ability to enhance, mimic, block and/or modulate sweet taste perception, in a mammal, preferably human, comprising a step of contacting one or more compounds with a combination of hT1 R2 and hT1R3 or a complex comprising a fragment, chimera, or variant of hT1R2 and/or hT1 R3.

It is another specific object of the invention to provide a method of screening one or more compounds for their ability to enhance, mimic, block and/or modulate taste perception, especially umami taste perception in a mammal, preferably human, comprising a step of contacting said one or more compounds with a combination of hT1R1 and hT1R3, or a complex comprising a fragment, chimera, or variant of hT1R1 and hT1R3.

It is another specific object of the invention to produce cells that co-express hT1R2 and hT1R3, or a fragment, variant or chimera thereof, for use in identifying compounds that enhance, mimic, block and/or modulate taste perception, especially sweet taste perception.

It is another specific object of the invention to produce cells that co-express hT1R1 and hT1R3 or a fragment, variant or chimera thereof for use in assays for identifying compounds that enhance, mimic, block and/or modulate taste perception, especially umami taste perception.

It is another object of the invention to produce non-human animals that have been genetically modified to express or not express one or more T1Rs.

It is yet another object of the invention to utilize a compound identified using an assay that utilizes T1Rs, or a combination thereof, as flavor ingredients in food and beverage compositions. In particular, it is an object of the invention to utilize a compound that interacts with hT1R2 and/or hT1R3 as a sweet blocker, enhancer, modulator, or mimic, and a compound that interacts with hT1R1 and/or hT1R3 as a umami blocker, enhancer, modulator, or mimic in food and beverage compositions.

It is another object of the invention to use T1Rs, in particular non-human T1Rs, to identify compounds that modulate the taste of animal feed formulations for use in, e.g., fish aquaculture.

It is a preferred object of the invention to provide eukaryotic, preferably mammalian or insect cell lines that stably co-express hT1R1/hT1 R3 or hT1 R2/hT1 R3, preferably HEK-293 cell lines, which also express a G protein, e.g., Gα15 or another G protein that when expressed in association with T1R2/T1R3 or T1R1/T1R3 produces a functional taste receptor.

It is another preferred object of the invention to provide eukaryotic cell lines, preferably mammalian or insect cells, that stably express T1R1/T1R3 or T1R2/T1R3, preferably hT1 μl/hT1R3 or hT1R2/hT1R3. In a preferred embodiment such cells will comprise HEK-293 cells that stably express Gα15 or another G protein that associates with T1R1/T1R3 or T1R2/T1R3 to produce a functional umami or sweet taste receptor.

It is also an object of the invention to provide assays, preferably high throughput assays using HEK-293 or other cell lines that stably or transiently express T1R1/T1R3 or T1R2/T1R3, under constitutive or inducible conditions to identify compounds that modulate umami or sweet taste.

It is another specific object of the invention to identify compounds that enhance, mimic, block and/or modulate the T1R1/T1R3 umami taste receptor based on their ability to affect the binding of lactisole (a sweet taste inhibitor) or a structurally related compound to the T1R1/T1R3 (umami) taste receptor.

BRIEF DESCRIPTION OF THE FIGURES

FIGS. 1*a*-1*b* contain a sequence alignment of human (SEQ ID NOS. 5-7) and rat T1Rs (SEQ ID NOS. 16-17 & 4), human calcium-sensing receptor (SEQ ID NO: 19) and rat metabotropic glutamate receptor (SEQ ID NO: 18).

FIG. 3*c* contains the normalized response to different sweeteners.

FIG. 8*a* shows that intracellular calcium increases in response to increasing glutamate concentration; FIG. 8*b* shows intracellular calcium responds to IMP (2 mM), glutamate (0.5 mM) and 0.2 mM IMP; and FIG. 8*c* shows human T1R1/T1R3 responses for glutamate in the presence and absence of 0.2 mM IMP.

In FIG. 14 different C-amino acids at 10 mM were tested in the presence and absence of 1 mM IMP. In FIG. 15 dose-responses for active amino acids were determined in the presence of 0.2 mM IMP.

DETAILED DESCRIPTION OF THE INVENTION

Figure 2:
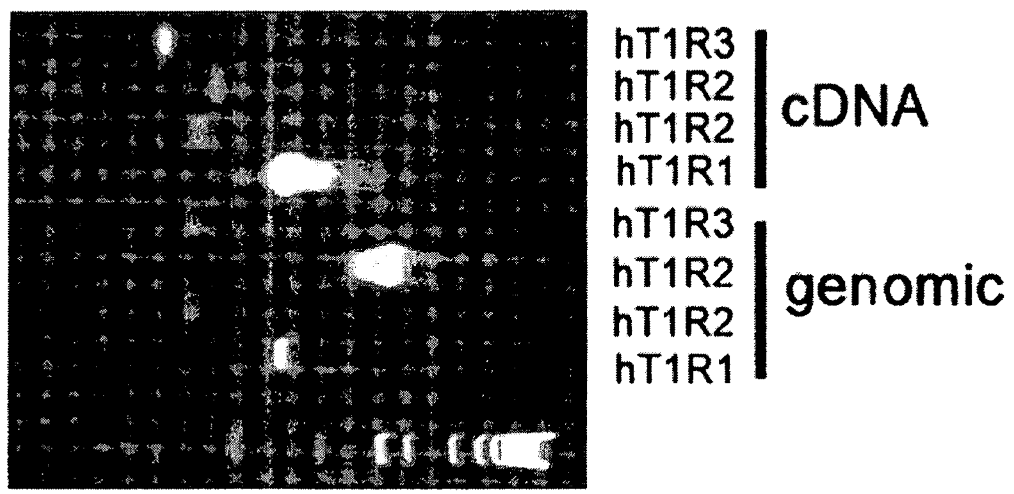
FIG. 2 contains RT-PCR amplification experimental results which show that hT1R2 and hT1R3 are expressed in taste tissue.

The invention thus provides functional taste receptors, preferably human taste receptors, that are produced by co-expression of a combination of different T1Rs, preferably T1R1/T1R3 or T1R2/T1 R3, and the corresponding isolated nucleic acid sequences or fragments, chimeras, or variants thereof that upon co-expression result in a functional taste receptor, i.e., a sweet taste receptor (T1R2/T1 R3) or umami taste receptor (T1R1/T1R3).

As has been reported in the literature, Members of the T1R family of taste-cell-specific GPCRs known and are identified in Hoon et al., *Cell,* 96:541-551 (1999), WO 00/06592, WO 00/06593, and U.S. Ser. No. 09/799,629, all of which are incorporated herein by reference in their entireties.

More particularly, the invention relates to the co-expression of different taste-cell specific GPCRs. These nucleic acids and the receptors that they encode are referred to as members of the "T1R" family of taste-cell-specific GPCRs. In particular embodiments of the invention, the T1R family members that are co-expressed will include rT1R1, rT1R2, rT1R3, mT1R1, mT1R2, mT1R3, hT1 R1, hT1 R2 and hT1 R3. While not wishing to be bound by theory, it is believed that these taste-cell-specific GPCRs are components of the taste transduction pathway, and are involved in the taste detection of sweet and umami taste stimuli and/or other taste stimuli representing other taste modalities.

It is established herein that T1R family members act in combination with other T1R family members to function as sweet and umami taste receptors. As disclosed in further detail infra in the experimental examples, it has been demonstrated that heterologous cells which co-express hT1 R2 and hT1R3 are selectively activated by sweet taste stimuli in a manner that mirrors human sweet taste. For example, HEK-293-Gα15 cells that co-express hT1 R2 and hT1 R3 specifically respond to cyclamate, sucrose, aspartame, and saccharin, and the dose responses for these compounds correlate with the psychophysical taste detection thresholds. Therefore, cells that co-express hT1R2 and hT1 R3 can be used in screens, preferably high throughput screens, to identify compounds that mimic, modulate, block, and/or enhance sweet taste sensation.

Also, as supported by data in the experimental examples, it has been shown that cells which co-express hT1R1 and hT1R3 are selectively activated by glutamate (monosodium glutamate) and 5'-ribonucleotides in a manner that mirrors human umami taste. For example, HEK-293-Gα15 cells that co-express hT1R1 and hT1R3 specifically respond to glutamate and the dose response for this umami-tasting compound correlates with its psychophysical taste detection threshold. Moreover, 5'-ribonucleotides such as IMP enhance the glutamate response of the T1R1/T1R3 receptor, a synergism characteristic of umami taste. Therefore, cells that co-express hT1R1 and hT1R3 can be used in screens, preferably high throughput screens to identify compounds that mimic, modulate, block, and/or enhance umami taste sensation.

Further, as shown by experimental data in the examples it has been shown that cells which stably and inducibly co-express T1R1/T1R3 selectively respond to the umami taste stimuli L-glutamate and L-aspartate and only weakly respond to other L-amino acids, and at much higher concentrations, providing further evidence that the T1R1/T1R3 receptor can be used in assays to identify compounds that modulate (enhance or block) umami taste stimuli.

Also, as supported by experimental data in the examples, it has been shown that cell lines which co-express T1R1/T1R3 or T1R2/T1 R3 respectively respond to umami or sweet taste stimuli and a quantitative dose-responsive manner which further supports a conclusion that the T1R1/T1R3 and T1R2/T1 R3 receptor can be used to identify receptor agonists and antagonists, e.g., MSG substitutes, umami blockers, novel artificial and natural sweeteners, and sweet blockers.

Also, as supported by data in experimental examples, it has been shown that the sweet taste blocker lactisole inhibits both the T1R2/T1 R3 sweet receptor and the T1R1/T1R3 umami taste receptor. This suggests that assays which screen for compounds which affect the binding of lactisole to T1R2/T1 R3 or T1R1/T1R3 may be used to identify compounds that enhance, mimic, modulate or block sweet or umami taste. The fact that lactisole inhibits both the T1R1/T1R3 and T1R2/T1R3 receptors suggests that these receptors may share a common subunit which is bound by lactisole and potentially other taste modulators. Therefore, this suggests that some compounds which enhance, mimic, modulate or block sweet taste may have a similar effect on umami taste or vice versa.

Further, as supported by data in experimental examples, it has been demonstrated that cell lines which stably co-express T1Rs, i.e. T1R1/T1R3 or T1R2/T1R3, when assayed by automated fluorescence imaging very effectively respond to various sweet and umami taste stimuli, i.e. at magnitudes substantially greater than transiently transfected cells. Thus, these cell lines are especially well suited for use in high throughput screening assays for identifying compounds that modulate, block, mimic or enhance sweet or umami taste. However, the invention also encompasses assays that utilize cells that transiently express a T1R or combination thereof.

Moreover, while the application contains data demonstrating that some T1Rs act in combination, particularly T1R1/T1R3 and T1R2/T1R3, and that such receptor combinations may be used in assays, preferably high throughput assays, it should be noted that the subject invention also encompasses assays that utilize T1R1, T1R2 and T1R3 alone or in combination with other proteins, e.g., other GPCRs.

With respect thereto, it is speculated that the sweet receptors may be comprised only of T1R2 and/or that the umami receptor may be comprised only of T1R1, with the T1R3 receptor perhaps functioning to facilitate the surface expression of T1R2 or T1R1.

Alternatively, it is hypothesized that the sweet receptor and the umami receptor may be composed only of T1R3, which may be differentially processed under the control of T1R1 and/or T1R2. This type of receptor expression would be akin to the RAMP-dependent processing of the calcitonin-related receptor.

Compounds identified with T1R assays can be used to modulate the taste of foods and beverages. Suitable assays described in further detail infra include by way of example whole-cell assays and biochemical assays, including direct-binding assays using one of a combination of different T1R receptors, chimeras or fragments thereof, especially fragments containing N-terminal ligand-binding domains. Examples of assays appropriate for use in the invention are described in greater detail infra and are known in the GPCR field.

Assays can be designed that quantitate the binding of different compounds or mixtures of compounds to T1R taste receptors or T1R taste receptor combinations or T1R receptors expressed in combination with other heterologous (non-T1R) proteins, e.g. other GPCRs, or that quantitate the activation of cells that express T1R taste receptors. This can be effected by stably or transiently expressing taste receptors in heterologous cells such as HEK-293, CHO and COS cells.

The assays will preferably use cells that also express (preferably stably) a G protein such as Gα15 or Gα16 or other promiscuous G proteins or G protein variants, or an endogenous G protein. In addition, $G_\beta$ and $G_\gamma$ proteins may also be expressed therein.

The effect of a compound on sweet or umami taste using cells or compositions that express or contain the above-identified receptors or receptor combinations may be determined by various means including the use of calcium-sensitive dyes, voltage-sensitive dyes, cAMP assays, direct binding assays using fluorescently labeled ligands or radioactive ligands such as $^3$H-glutamate, or transcriptional assays (using a suitable reporter such as luciferase or beta-lactamase).

Assays that may be utilized with one or more T1Rs according to the invention include by way of example, assays that utilize a genetic selection for living cells; assays that utilize whole cells or membrane fragments or purified T1R proteins; assays that utilize second messengers such as cAMP and IP3, assays that detect the translocation of arrestin to the cell surface, assays that detect the loss of receptor expression on the cell surface (internalization) by tested ligands, direct ligand-binding assays, competitive-binding assays with inhibitors, assays using in vitro translated protein, assays that detect conformational changes upon the binding of a ligand (e.g., as evidenced by proteolysis, fluorescence, or NMR), behavioral assays that utilize transgenic non-human animals that express a T1R or T1R combination, such as flies, worms, or mice, assays that utilize cells infected with recombinant viruses that contain T1R genes.

Also within the scope of the invention are structure-based analyses wherein the X-ray crystal structure of a T1R or T1R fragment (or combination of T1Rs, or a combination of a T1R with another protein) is determined and utilized to predict by molecular modeling techniques compounds that will bind to and/or enhance, mimic, block or modulate the particular T1R receptor or receptor combination. More particularly, the invention embraces the determination of the crystal structure of T1R1/T1R3 (preferably hT1R1/hT1R3) and/or T1R2/T1R3 (preferably hT1R2/hT1R3) and the use of such crystal structures in structure-based design methods to identify molecules that modulate T1R receptor activity.

The invention especially includes biochemical assays conducted using cells, e.g., mammalian, yeast, insect or other heterologous cells that express one or more full length TI R receptors or fragments, preferably N-terminal domains of T1R1, T1R2 and/or T1R3. The effect of a compound in such assays can be determined using competitive binding assays, e.g., using radioactive glutamate or IMP, fluorescence (e.g., fluorescence polarization, FRET), or $GTP_{\gamma}$ $^{35}S$ binding assays. As noted, in a preferred embodiment, such assays will utilize cell lines that stably co-express T1R1/T1R3 or T1R2/T1R3 and a suitable G protein, such as $G_{\alpha 15}$. Other appropriate G proteins include the chimeric and variant G proteins disclosed in U.S. application Ser. No. 09/984,292 and 60/243,770, incorporated by reference in their entirety herein.

Still further, altered receptors can be constructed and expressed having improved properties, e.g., enhanced surface expression or G-protein coupling. These T1R variants can be incorporated into cell-based and biochemical assays.

It is envisioned that the present discoveries relating to human T1Rs will extend to other species, e.g., rodents, pigs, monkeys, dogs and cats, and perhaps even non-mammals such as fish. In this regard, several fish T1R fragments are identified infra in Example 1. Therefore, the subject invention has application in screening for compounds for use in animal feed formulations.

The invention further includes that utilize different allelic variants of various T1Rs and combinations thereof, thereby enabling the identification of compounds that elicit specific taste sensation in individuals that express those allelic variants or compounds that elicit specific taste sensations in all individuals. Such compounds can be used to make foods more generally palatable.

T1R encoding nucleic acids also provide valuable probes for the identification of taste cells, as the nucleic acids are specifically expressed in taste cells. For example, probes for T1R polypeptides and proteins can be used to identify taste cells present in foliate, circumvallate, and fungiform papillae, as well as taste cells present in the geschmackstreifen, oral cavity, gastrointestinal epithelium, and epiglottis. In particular, methods of detecting T1Rs can be used to identify taste cells sensitive to sweet and/or umami taste stimuli or other taste stimuli representing other taste modalities. For example, cells stably or transiently expressing T1R2 and/or T1R3 would be predicted from the work herein to be responsive to sweet taste stimuli. Similarly, cells expressing T1R1 and/or T1R3 would be predicted to be responsive to umami taste stimuli. The nucleic acids encoding the T1R proteins and polypeptides of the invention can be isolated from a variety of sources, genetically engineered, amplified, synthesized, and/or expressed recombinantly according to the methods disclosed in WO 00/035374, which is herein incorporated by reference in its entirety. A listing of T1Rs that may be expressed according to the invention are provided in the Examples. However, it should be emphasized that the invention embraces the expression and use of other specific T1Rs or fragments, variants, or chimeras constructed based on such T1R sequences, and particularly T1Rs of other species.

As disclosed, an important aspect of the invention is the plurality of methods of screening for modulators, e.g., activators, inhibitors, stimulators, enhancers, agonists, and antagonists, of these taste-cell-specific GPCRs. Such modulators of taste transduction are useful for the modulation of taste signaling pathways. These methods of screening can be used to identify high affinity agonists and antagonists of taste cell activity. These modulatory compounds can then be used in the food industry to customize taste, e.g., to modulate the sweet and/or umami tastes of foods.

This invention rectifies the previous lack of understanding relating to sweet and umami taste as it identifies specific T1Rs and T1R receptor combinations that mediate sweet and umami taste sensation. Therefore, in general, this application relates to the inventors' discoveries relating to the T1R class of taste-specific G-protein-coupled receptors and their specific function in taste perception and the relationship of these discoveries to a better understanding of the molecular basis of taste.

The molecular basis of sweet taste and umami taste—the savor of monosodium glutamate—is enigmatic. Recently, a three-member class of taste-specific G-protein-coupled receptors, termed T1Rs, was identified. Overlapping T1R expression patterns and the demonstration that the structurally related $GABA_B$ receptor is heterodimeric suggest that the T1Rs function as heterodimeric taste receptors. In the examples infra, the present inventors describe the functional co-expression of human T1R1, T1R2, and T1R3 in heterologous cells; cells co-expressing T1R1 and T1R3 are activated by umami taste stimuli; cells co-expressing T1R2 and T1R3 are activated by sweet taste stimuli. T1R1/T1R3 and T1R2/T1 R3 activity correlated with psychophysical detection thresholds. In addition, the 5'-ribonucleotide IMP was found to enhance the T1R1/T1R3 response to glutamate, a synergism characteristic of umami taste. These findings demonstrate that specific T1Rs and particularly different combinations of the T1Rs function as sweet and umami taste receptors.

Human perception of bitter, sweet, and umami is thought to be mediated by G-protein-coupled receptors (Lindemann, B., *Physiol. Res.* 76:718-66 (1996)). Recently, evaluation of the human genome revealed the T2R class of bitter taste receptors (Adler et al., *Cell* 100:613-702 (2000); Chandrasgekar et al., *Cell* 100:703-11 (2000); Matsunami et al., *Nature* 404: 601-604 (2000)) but the receptors for sweet and umami taste have not been identified. Recently, another class of candidate taste receptors, the T1Rs, was identified. The T1Rs were first identified by large-scale sequencing of a subtracted cDNA library derived from rat taste tissue, which identified T1R1, and subsequently by T1R1-based degenerate PCR, which led to the identification of T1R2 (Hoon et al., *Cell* 96:541-551 (1999)). Recently, the present inventors and others identified a third and possibly final member of the T1R family, T1R3, in the human genome databank (Kitagawa et al., *Biochem Biophys. Res Commun.* 283(1): 236-42 (2001); Max et al., *Nat. Genet.* 28(1): 58-63 (2001); Sainz et al., *J. Neurochem.* 77(3): 896-903 (2001); Montmayeur et al., *Nat. Neurosci.* 4, 492-8. (2001)). Tellingly, mouse T1R3 maps to a genomic interval containing Sac, a locus that influences sweet taste in the mouse (Fuller et al., *J. Hered.* 65:33-6 (1974); Li et al., *Mamm. Genome* 12:13-16 (2001)). Therefore, T1R3 was predicted to function as a sweet taste receptor. Recent high-resolution genetic mapping studies have strengthened the connection between mouse T1R3 and Sac (Fuller T. C., *J. Hered.* 65(1): 33-36 (1974); Li et al., *Mammal. Genome* 12(1): 13-16 (2001)).

Interestingly, all C-family receptors that have been functionally expressed thus far—metabotropic glutamate receptors, the $GABA_B$ receptor, the calcium-sensing receptor (Conigrave, A. D., Quinn, S. J. & Brown, E. M., *Proc Natl Acad Sci USA* 97, 4814-9. (2000)), and a fish olfactory receptor (Speca, D. J. et al., *Neuron* 23, 487-98. (1999))—have been shown to be activated by amino acids. This common feature raises the possibility that the T1Rs recognize amino acids, and that the T1Rs may be involved in the detection of glutamate in addition to sweet-tasting amino acids. Alternatively, a transcriptional variant of the mGluR4 metabotropic glutamate receptor has been proposed to be the umami taste receptor because of its selective expression in rat taste tissue, and the similarity of the receptor-activation threshold to the glutamate psychophysical detection threshold (Chaudhari et al., *Nat. Neurosci.* 3:113-119 (2000)). This hypothesis is difficult to reconcile with the exceedingly low expression level of the mGluR4 variant in taste tissue, and the more or less unaltered glutamate taste of mGluR4 knockout mice (Chaudhari and Roper, *Ann. N.Y. Acad. Sci.* 855:398-406 (1998)). Furthermore, the taste variant is structurally implausible, lacking not only the majority of the residues that form the glutamate-binding pocket of the wild-type receptor, but also approximately half of the globular N-terminal glutamate-binding domain (Kunishima et al., *Nature* 407:971-7 (2000)).

Comparative analysis of T1R expression patterns in rodents has demonstrated that T1 R2 and possibly T1R1 are each coexpressed with T1R3 (Hoon et al., *Cell* 96:541-51 (1999); Kitagawa et al., *Biochem Biophy. Res. Commun.* 283:236-242 (2001); Max et al., *Nat. Genet.* 28:58-63 (2001); Montmayeur et al., *Nat. Neurosci* 4:492-8 (2001); Sainz et al., *J. Neurochem* 77:896-903 (2001)). Furthermore, dimerization is emerging as a common theme of C-family receptors: the metabotropic glutamate and calcium-sensing receptor are homodimers (Romomano et al., *J. Biol. Chem.* 271:28612-6 (1996); Okamoto et al., *J. Biol. Chem.* 273: 13089-96 (1998); Han et al., *J. Biol. Chem.* 274:100008-13 (1999); Bai et al., *J. Biol. Chem.* 273:23605-10 (1998)), and the structurally related $GABA_B$ receptor is heterodimeric (Jones et al., Nature 396:674-9 (1998); Kaupmann et al., *Nature* 396:683-687 (1998); White et al., *Nature* 396: 679-682 (1998); Kuner et al., *Science* 283:74-77 (1999)). The present inventors have demonstrated by functional coexpression of T1Rs in heterologous cells that human T1R2 functions in combination with human T1 R3 as a sweet taste receptor and that human T1R1 functions in combination with human T1R3 as an umami taste receptor.

The discoveries discussed herein are especially significant, as previously the development of improved artificial sweeteners has been hampered by the lack of assays for sweet taste. Indeed, the five commonly used commercial artificial sweeteners, all of which activate hT1R2/hT1R3, were discovered serendipitously. Similarly, other than sensory testing, a laborious process, there is no assay for identifying compounds that modulate umami taste. These problems are now alleviated because, as established by experimental results discussed infra, the human sweet and umami receptors have been identified, and assays for these receptors have been developed, particularly assays that use cells that stably express a functional T1R taste receptor, i.e. the sweet or umami taste receptor.

Based thereon the invention provides assays for detecting and characterizing taste-modulating compounds, wherein T1R family members act, as they do in the taste bud, as reporter molecules for the effect on sweet and umami taste of taste-modulating compounds. Particularly provided and within the scope of the invention are assays for identifying compounds that modulate, mimic, enhance and/or block individually, sweet and umami tastes. Methods for assaying the activity of GPCRs, and especially compounds that affect GPCR activity are well known and are applicable to the T1R family member of the present invention and functional combinations thereof. Suitable assays have been identified supra.

In particular, the subject GPCRs can be used in assays to, e.g., measure changes in ligand binding, ion concentration, membrane potential, current flow, ion flux, transcription, receptor-ligand interactions, second messenger concentrations, in vitro and in vivo. In another embodiment, T1R family members may be recombinantly expressed in cells, and the modulation of taste transduction via GPCR activity may be assayed by measuring changes in $Ca^{2+}$ levels and other intracellular messages such as cAMP, cGMP, or $IP_3$.

In certain assays, a domain of a T1R polypeptide, e.g., an extracellular, transmembrane, or intracellular domain, is fused to a heterologous polypeptide, thereby forming a chimeric polypeptide, e.g., a chimeric protein with GPCR activity. Particularly contemplated is the use of fragments of T1R1, T1R2 or T1R3 containing the N-terminal ligand-binding domain. Such proteins are useful, e.g., in assays to identify ligands, agonists, antagonists, or other modulators of T1R receptors. For example, a T1R polypeptide can be expressed in a eukaryotic cell as a chimeric receptor with a heterologous, chaperone sequence that facilitates plasma membrane trafficking, or maturation and targeting through the secretory pathway. The optional heterologous sequence may be a PDZ domain-interacting peptide, such as a C-terminal PDZIP fragment (SEQ ID NO 1). PDZIP is an ER export signal, which, according to the present invention, has been shown to facilitate surface expression of heterologous proteins such as the T1R receptors described herein. More particularly, in one aspect of the invention, PDZIP can be used to promote proper targeting of problematic membrane proteins such as olfactory receptors, T2R taste receptors, and the T1R taste receptors described herein.

Such chimeric T1R receptors can be expressed in any eukaryotic cell, such as HEK-293 cells. Preferably, the cells contain a G protein, preferably a promiscuous G protein such as $G_{\alpha15}$ or $G_{\alpha16}$ or another type of promiscuous G protein capable of linking a wide range of GPCRs to an intracellular signaling pathway or to a signaling protein such as phospholipase C. Activation of such chimeric receptors in such cells can be detected using any standard method, such as by detecting changes in intracellular calcium by detecting FURA-2 dependent fluorescence in the cell. If preferred host cells do not express an appropriate G protein, they may be transfected with a gene encoding a promiscuous G protein such as those described in U.S. Application Ser. No. 60/243,770, U.S. application Ser. No. 09/984,297, filed Oct. 29, 2001, and U.S. application Ser. No. 09/989,497 filed Nov. 21, 2001 which are herein incorporated by reference in its entirety.

Additional methods of assaying for modulators of taste transduction include in vitro ligand-binding assays using: T1R polypeptides, portions thereof, i.e., the extracellular domain, transmembrane region, or combinations thereof, or chimeric proteins comprising one or more domains of a T1R family member; oocyte or tissue culture cells expressing T1R polypeptides, fragments, or fusion proteins; phosphorylation and dephosphorylation of T1R family members; G protein binding to GPCRs; ligand-binding assays; voltage, membrane potential and conductance changes; ion flux assays; changes in intracellular second messengers such as cGMP, cAMP and inositol triphosphate (IP3); and changes in intracellular calcium levels.

Further, the invention provides methods of detecting T1 R nucleic acid and protein expression, allowing investigation of taste transduction regulation and specific identification of taste receptor cells. T1R family members also provide useful nucleic acid probes for paternity and forensic investigations. T1 R genes are also useful as nucleic acid probes for identifying taste receptor cells, such as foliate, fungiform, circumvallate, geschmackstreifen, and epiglottis taste receptor cells. T1 R receptors can also be used to generate monoclonal and polyclonal antibodies useful for identifying taste receptor cells.

Functionally, the T1R polypeptides comprise a family of related seven transmembrane G protein-coupled receptors, which are believed to be involved in taste transduction and may interact with a G protein to mediate taste signal transduction (see, e.g., Fong, *Cell Signal,* 8:217 (1996); Baldwin, *Curr. Opin. Cell Biol.,* 6:180 (1994)). Structurally, the nucleotide sequences of T1R family members encode related polypeptides comprising an extracellular domain, seven transmembrane domains, and a cytoplasmic domain. Related T1 R family genes from other species share at least about 50%, and optionally 60%, 70%, 80%, or 90%, nucleotide sequence identity over a region of at least about 50 nucleotides in length, optionally 100, 200, 500, or more nucleotides in length to the T1R nucleic acid sequences disclosed herein in the Examples, or conservatively modified variants thereof, or encode polypeptides sharing at least about 35 to 50%, and optionally 60%, 70%, 80%, or 90%, amino acid sequence identity over an amino acid region at least about 25 amino acids in length, optionally 50 to 100 amino acids in length to a T1 R polypeptide sequence disclosed infra in the Examples conservatively modified variants thereof.

Several consensus amino acid sequences or domains have also been identified that are characteristic of T1 R family members. For example, T1R family members typically comprise a sequence having at least about 50%, optionally 55%, 60%, 65%, 70%, 75%, 80%, 85%, 90%, 95-99%, or higher, identity to T1R consensus sequences 1 and 2 (SEQ ID NOs. 2 and 3, respectively). These conserved domains thus can be used to identify members of the T1R family, by identity, specific hybridization or amplification, or specific binding by antibodies raised against a domain. T1R consensus sequences include by way of example the following sequences:

T1R Family Consensus Sequence 1: (SEQ ID NO: 2)
(TR)C(FL)(RQP)R(RT)(SPV)(VERKT)FL(AE)(WL)(RHG)E T1R Family Consensus Sequence 2: (SEQ ID NO: 3)
(LQ)P(EGT)(NRC)YN(RE)A(RK)(CGF)(VLI)T(FL)(AS)(ML)

These consensus sequences are inclusive of those found in the T1R polypeptides described herein, but T1R family members from other organisms may be expected to comprise consensus sequences having about 75% identity or more to the inclusive consensus sequences described specifically herein.

Specific regions of the T1R nucleotide and amino acid sequences may be used to identify polymorphic variants, interspecies homologs, and alleles of T1R family members. This identification can be made in vitro, e.g., under stringent hybridization conditions or PCR (e.g., using primers encoding the T1R consensus sequences identified above), or by using the sequence information in a computer system for comparison with other nucleotide sequences. Different alleles of T1R genes within a single species population will also be useful in determining whether differences in allelic sequences control differences in taste perception between members of the population. Classical PCR-type amplification and cloning techniques are useful for isolating new T1Rs, for example, where degenerate primers are sufficient for detecting related genes across species.

Typically, identification of polymorphic variants and alleles of T1R family members can be made by comparing an amino acid sequence of about 25 amino acids or more, e.g., 50-100 amino acids. Amino acid identity of approximately at least 35 to 50%, and optionally 60%, 70%, 75%, 80%, 85%, 90%, 95-99%, or above typically demonstrates that a protein is a polymorphic variant, interspecies homolog, or allele of a T1 R family member. Sequence comparison can be performed using any of the sequence comparison algorithms discussed below. Antibodies that bind specifically to T1R polypeptides or a conserved region thereof can also be used to identify alleles, interspecies homologs, and polymorphic variants.

Polymorphic variants, interspecies homologs, and alleles of T1R genes can be confirmed by examining taste-cell-specific expression of the putative T1R gene or protein. Typically, T1R polypeptides having an amino acid sequence disclosed herein can be used as a positive control in comparison to the putative T1R polypeptide to demonstrate the identification of a polymorphic variant or allele of the T1R family member. The polymorphic variants, alleles, and interspecies homologs are expected to retain the seven transmembrane structure of a G protein-coupled receptor. For further detail, see WO 00/06592, which discloses related T1R family members, GPCR-B3s, the contents of which are herein incorporated by reference in a manner consistent with this disclosure. GPCR-B3 receptors are referred to herein as rT1R1 and mT1R1. Additionally, see WO 00/06593, which also discloses related T1R family members, GPCR-B4s, the contents of which are herein incorporated by reference in a manner consistent with this disclosure. GPCR-B4 receptors are referred to herein as rT1R2 and mT1R2. As discussed previously, the invention also includes structure-based assays that utilize the x-ray crystalline structure of a T1R or T1R combination, e.g., hT1 R2/hT1 R3 or hT1 R1/hT1 R3, to identify molecules that modulate T1R receptor activity, and thereby modulate sweet and/or umami taste.

The present invention also provides assays, preferably high throughput assays, to identify molecules that enhance, mimic, block and/or modulate T1R receptors. In some assays, a particular domain of a T1R family member is used in combination with a particular domain of another T1R family member, e.g., an extracellular, transmembrane, or intracellular domain or region. In other embodiments, an extracellular domain, transmembrane region or combination thereof may be bound to a solid substrate, and used, e.g., to isolate ligands, agonists, antagonists, or any other molecules that can bind to and/or modulate the activity of a T1R polypeptide.

Various conservative mutations and substitutions are envisioned to be within the scope of the invention. For instance, it is within the level of skill in the art to perform amino acid substitutions using known protocols of recombinant gene technology including PCR, gene cloning, site-directed mutagenesis of cDNA, transfection of host cells, and in-vitro transcription. The variants could then be screened for activity.

DEFINITIONS

As used herein, the following terms have the meanings ascribed to them unless specified otherwise.

"Taste cells" include neuroepithelial cells that are organized into groups to form taste buds of the tongue, e.g., foliate, fungiform, and circumvallate cells (see, e.g., Roper et al., Ann. Rev. Neurosci. 12:329-353 (1989)). Taste cells are also found in the palate and other tissues, such as the esophagus and the stomach.

"T1R" refers to one or more members of a family of G protein-coupled receptors that are expressed in taste cells such as foliate, fungiform, and circumvallate cells, as well as cells of the palate, and esophagus (see, e.g., Hoon et al., *Cell,* 96:541-551 (1999), herein incorporated by reference in its entirety). Members of this family are also referred to as GPCR-B3 and TR1 in WO 00/06592 as well as GPCR-B4 and TR2 in WO 00/06593. GPCR-B3 is also herein referred to as rT1R1, and GPCR-B4 is referred to as rT1R2. Taste receptor cells can also be identified on the basis of morphology (see, e.g., Roper, supra), or by the expression of proteins specifically expressed in taste cells. T1R family members may have the ability to act as receptors for sweet taste transduction, or to distinguish between various other taste modalities. Representative T1R sequences, including hT1R1, hT1R2 and hT1R3 are identified infra in the examples.

"T1R" nucleic acids encode a family of GPCRs with seven transmembrane regions that have "G protein-coupled receptor activity," e.g., they may bind to G proteins in response to extracellular stimuli and promote production of second messengers such as IP3, cAMP, cGMP, and $Ca^{2+}$ via stimulation of enzymes such as phospholipase C and adenylate cyclase (for a description of the structure and function of GPCRs, see, e.g., Fong, supra, and Baldwin, supra). A single taste cell may contain many distinct T1R polypeptides.

The term "T1R" family therefore refers to polymorphic variants, alleles, mutants, and interspecies homologs that: (1) have at least about 35 to 50% amino acid sequence identity, optionally about 60, 75, 80, 85, 90, 95, 96, 97, 98, or 99% amino acid sequence identity to a T1R polypeptide, preferably those identified in Example 1, over a window of about 25 amino acids, optionally 50-100 amino acids; (2) specifically bind to antibodies raised against an immunogen comprising an amino acid sequence preferably selected from the group consisting of the T1R polypeptide sequence disclosed in Example 1 and conservatively modified variants thereof; (3) are encoded by a nucleic acid molecule which specifically hybridize (with a size of at least about 100, optionally at least about 500-1000 nucleotides) under stringent hybridization conditions to a sequence selected from the group consisting of the T1R nucleic acid sequences contained in Example 1, and conservatively modified variants thereof; or (4) comprise a sequence at least about 35 to 50% identical to an amino acid sequence selected from the group consisting of the T1R amino acid sequence identified in Example 1.

Topologically, certain chemosensory GPCRs have an "N-terminal domain;" "extracellular domains;" "transmembrane domains" comprising seven transmembrane regions, and corresponding cytoplasmic, and extracellular loops; "cytoplasmic domains," and a "C-terminal domain" (see, e.g., Hoon et al., *Cell,* 96:541-551 (1999); Buck & Axel, *Cell,* 65:175-187 (1991)). These domains can be structurally identified using methods known to those of skill in the art, such as sequence analysis programs that identify hydrophobic and hydrophilic domains (see, e.g., Stryer, *Biochemistry,* (3rd ed. 1988); see also any of a number of Internet based sequence analysis programs, such as those found at dot.imgen.bcm.tmc.edu). Such domains are useful for making chimeric proteins and for in vitro assays of the invention, e.g., ligand binding assays.

"Extracellular domains" therefore refers to the domains of T1R polypeptides that protrude from the cellular membrane and are exposed to the extracellular face of the cell. Such domains generally include the "N terminal domain" that is exposed to the extracellular face of the cell, and optionally can include portions of the extracellular loops of the transmembrane domain that are exposed to the extracellular face of the cell, i.e., the loops between transmembrane regions 2 and 3, between transmembrane regions 4 and 5, and between transmembrane regions 6 and 7.

The "N-terminal domain" region starts at the N-terminus and extends to a region close to the start of the first transmembrane domain. More particularly, in one embodiment of the invention, this domain starts at the N-terminus and ends approximately at the conserved glutamic acid at amino acid position 563 plus or minus approximately 20 amino acids. These extracellular domains are useful for in vitro ligand-binding assays, both soluble and solid phase. In addition, transmembrane regions, described below, can also bind ligand either in combination with the extracellular domain, and are therefore also useful for in vitro ligand-binding assays.

"Transmembrane domain," which comprises the seven "transmembrane regions," refers to the domain of T1R polypeptides that lies within the plasma membrane, and may also include the corresponding cytoplasmic (intracellular) and extracellular loops. In one embodiment, this region corresponds to the domain of T1R family members which starts approximately at the conserved glutamic acid residue at amino acid position 563 plus or minus 20 amino acids and ends approximately at the conserved tyrosine amino acid residue at position 812 plus or minus approximately 10 amino acids. The seven transmembrane regions and extracellular and cytoplasmic loops can be identified using standard methods, as described in Kyte & Doolittle, *J. Mol. Biol.,* 157:105-32 (1982)), or in Stryer, supra.

"Cytoplasmic domains" refers to the domains of T1R polypeptides that face the inside of the cell, e.g., the "C-terminal domain" and the intracellular loops of the transmembrane domain, e.g., the intracellular loop between transmembrane regions 1 and 2, the intracellular loop between transmembrane regions 3 and 4, and the intracellular loop between transmembrane regions 5 and 6. "C-terminal domain" refers to the region that spans the end of the last transmembrane domain and the C-terminus of the protein, and which is normally located within the cytoplasm. In one embodiment, this region starts at the conserved tyrosine amino acid residue at position 812 plus or minus approximately 10 amino acids and continues to the C-terminus of the polypeptide.

The term "ligand-binding region" or "ligand-binding domain" refers to sequences derived from a taste receptor, particularly a taste receptor that substantially incorporates at least the extracellular domain of the receptor. In one embodiment, the extracellular domain of the ligand-binding region may include the N-terminal domain and, optionally, portions of the transmembrane domain, such as the extracellular loops of the transmembrane domain. The ligand-binding region may be capable of binding a ligand, and more particularly, a compound that enhances, mimics, blocks, and/or modulates taste, e.g., sweet or umami taste.

The phrase "heteromultimer" or "heteromultimeric complex" in the context of the T1R receptors or polypeptides of the invention refers to a functional association of at least one T1R receptor and another receptor, typically another T1R receptor polypeptide (or, alternatively another non-T1R receptor polypeptide). For clarity, the functional co-dependence of the T1Rs is described in this application as reflecting their possible function as heterodimeric taste receptor complexes. However, as discussed previously, functional co-dependence may alternatively reflect an indirect interaction. For example, T1R3 may function solely to facilitate surface expression of T1 R1 and T1R2, which may act independently as taste receptors. Alternatively, a functional taste receptor may be comprised solely of T1R3, which is differentially processed under the control of T1R1 or T1R2, analogous to RAMP-dependent processing of the calcium-related receptor.

The phrase "functional effects" in the context of assays for testing compounds that modulate T1R family member mediated taste transduction includes the determination of any parameter that is indirectly or directly under the influence of the receptor, e.g., functional, physical and chemical effects. It includes ligand binding, changes in ion flux, membrane potential, current flow, transcription, G protein binding, GPCR phosphorylation or dephosphorylation, conformation change-based assays, signal transduction, receptor-ligand interactions, second messenger concentrations (e.g., cAMP, cGMP, IP3, or intracellular $Ca^{2+}$), in vitro, in vivo, and ex vivo and also includes other physiologic effects such increases or decreases of neurotransmitter or hormone release.

By "determining the functional effect" in the context of assays is meant assays for a compound that increases or decreases a parameter that is indirectly or directly under the influence of a T1R family member, e.g., functional, physical and chemical effects. Such functional effects can be measured by any means known to those skilled in the art, e.g., changes in spectroscopic characteristics (e.g., fluorescence, absorbency, refractive index), hydrodynamic (e.g., shape), chromatographic, or solubility properties, patch clamping, voltage-sensitive dyes, whole cell currents, radioisotope efflux, inducible markers, oocyte T1R gene expression; tissue culture cell T1R expression; transcriptional activation of T1R genes; ligand-binding assays; voltage, membrane potential and conductance changes; ion flux assays; changes in intracellular second messengers such as cAMP, cGMP, and inositol triphosphate (IP3); changes in intracellular calcium levels; neurotransmitter release, conformational assays and the like.

"Inhibitors," "activators," and "modulators" of T1R genes or proteins are used to refer to inhibitory, activating, or modulating molecules identified using in vitro and in vivo assays for taste transduction, e.g., ligands, agonists, antagonists, and their homologs and mimetics.

Inhibitors are compounds that, e.g., bind to, partially or totally block stimulation, decrease, prevent, delay activation, inactivate, desensitize, or down regulate taste transduction, e.g., antagonists. Activators are compounds that, e.g., bind to, stimulate, increase, open, activate, facilitate, enhance activation, sensitize, or up regulate taste transduction, e.g., agonists. Modulators include compounds that, e.g., alter the interaction of a receptor with: extracellular proteins that bind activators or inhibitor (e.g., ebnerin and other members of the hydrophobic carrier family); G proteins; kinases (e.g., homologs of rhodopsin kinase and beta adrenergic receptor kinases that are involved in deactivation and desensitization of a receptor); and arresting, which also deactivate and desensitize receptors. Modulators can include genetically modified versions of T1R family members, e.g., with altered activity, as well as naturally occurring and synthetic ligands, antagonists, agonists, small chemical molecules and the like. Such assays for inhibitors and activators include, e.g., expressing T1R family members in cells or cell membranes, applying putative modulator compounds, in the presence or absence of tastants, e.g., sweet tastants, and then determining the functional effects on taste transduction, as described above. Samples or assays comprising T1R family members that are treated with a potential activator, inhibitor, or modulator are compared to control samples without the inhibitor, activator, or modulator to examine the extent of modulation. Positive control samples (e.g. a sweet tastant without added modulators) are assigned a relative T1R activity value of 100%.

Negative control samples (e.g. buffer without an added taste stimulus) are assigned a relative T1R activity value of 0%. Inhibition of a T1R is achieved when a mixture of the positive control sample and a modulator result in the T1R activity value relative to the positive control is about 80%, optionally 50% or 25-0%. Activation of a T1R by a modulator alone is achieved when the T1R activity value relative to the positive control sample is 10%, 25%, 50%, 75%, optionally 100%, optionally 150%, optionally 200-500%, or 1000-3000% higher.

The terms "purified," "substantially purified," and "isolated" as used herein refer to the state of being free of other, dissimilar compounds with which the compound of the invention is normally associated in its natural state, so that the "purified," "substantially purified," and "isolated" subject comprises at least 0.5%, 1%, 5%, 10%, or 20%, and most preferably at least 50% or 75% of the mass, by weight, of a given sample. In one preferred embodiment, these terms refer to the compound of the invention comprising at least 95% of the mass, by weight, of a given sample. As used herein, the terms "purified," "substantially purified," and "isolated," when referring to a nucleic acid or protein, also refers to a state of purification or concentration different than that which occurs naturally in the mammalian, especially human body. Any degree of purification or concentration greater than that which occurs naturally in the mammalian, especially human, body, including (1) the purification from other associated structures or compounds or (2) the association with structures or compounds to which it is not normally associated in the mammalian, especially human, body, are within the meaning of "isolated." The nucleic acid or protein or classes of nucleic acids or proteins, described herein, may be isolated, or otherwise associated with structures or compounds to which they are not normally associated in nature, according to a variety of methods and processes known to those of skill in the art.

The term "nucleic acid" or "nucleic acid sequence" refers to a deoxyribonucleotide or ribonucleotide oligonucleotide in either single- or double-stranded form. The term encompasses nucleic acids, i.e., oligonucleotides, containing known analogs of natural nucleotides. The term also encompasses nucleic-acid-like structures with synthetic backbones (see e.g., *Oligonucleotides and Analogues, a Practical Approach*, ed. F. Eckstein, Oxford Univ. Press (1991); *Antisense Strategies, Annals of the N.Y. Academy of Sciences*, Vol. 600, Eds. Baserga et al. (NYAS 1992); Milligan *J. Med. Chem.* 36:1923-1937 (1993); *Antisense Research and Applications* (1993, CRC Press), WO 97/03211; WO 96/39154; Mata, *Toxicol. Appl. Pharmacol.* 144:189-197 (1997); Strauss-Soukup, *Biochemistry* 36:8692-8698 (1997); Samstag, *Antisense Nucleic Acid Drug Dev,* 6:153-156 (1996)).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating, e.g., sequences in which the third position of one or more selected codons is substituted with mixed-base and/or deoxyinosine residues (Batzer et al., *Nucleic Acid Res.,* 19:5081 (1991); Ohtsuka et al., *J. Biol. Chem.,* 260:2605-2608 (1985); Rossolini et al., Mol. Cell. Probes, 8:91-98 (1994)). The term nucleic acid is used interchangeably with gene, cDNA, mRNA, oligonucleotide, and polynucleotide.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "plasma membrane translocation domain" or simply "translocation domain" means a polypeptide domain that, when incorporated into a polypeptide coding sequence, can with greater efficiency "chaperone" or "translocate" the hybrid ("fusion") protein to the cell plasma membrane than without the domain. For instance, a "translocation domain" may be derived from the amino terminus of the bovine rhodopsin receptor polypeptide, a 7-transmembrane receptor. However, rhodopsin from any mammal may be used, as can other translocation facilitating sequences. Thus, the translocation domain is particularly efficient in translocating 7-transmembrane fusion proteins to the plasma membrane, and a protein (e.g., a taste receptor polypeptide) comprising an amino terminal translocating domain will be transported to the plasma membrane more efficiently than without the domain. However, if the N-terminal domain of the polypeptide is active in binding, as with the T1R receptors of the present invention, the use of other translocation domains may be preferred. For instance, a PDZ domain-interacting peptide, as described herein, may be used.

The "translocation domain," "ligand-binding domain", and chimeric receptors compositions described herein also include "analogs," or "conservative variants" and "mimetics" ("peptidomimetics") with structures and activity that substantially correspond to the exemplary sequences. Thus, the terms "conservative variant" or "analog" or "mimetic" refer to a polypeptide which has a modified amino acid sequence, such that the change(s) do not substantially alter the polypeptide's (the conservative variant's) structure and/or activity, as defined herein. These include conservatively modified variations of an amino acid sequence, i.e., amino acid substitutions, additions or deletions of those residues that are not critical for protein activity, or substitution of amino acids with residues having similar properties (e.g., acidic, basic, positively or negatively charged, polar or non-polar, etc.) such that the substitutions of even critical amino acids does not substantially alter structure and/or activity.

More particularly, "conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein.

For instance, the codons GCA, GCC, GCG and GCU all encode the amino acid alanine. Thus, at every position where an alanine is specified by a codon, the codon can be altered to any of the corresponding codons described without altering the encoded polypeptide.

Such nucleic acid variations are "silent variations," which are one species of conservatively modified variations. Every nucleic acid sequence herein, which encodes a polypeptide, also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid, which encodes a polypeptide, is implicit in each described sequence.

Conservative substitution tables providing functionally similar amino acids are well known in the art. For example, one exemplary guideline to select conservative substitutions includes (original residue followed by exemplary substitution): ala/gly or ser; arg/lys; asn/gin or his; asp/glu; cys/ser; gln/asn; gly/asp; gly/ala or pro; his/asn or gin; ile/leu or val; leu/ile or val; lys/arg or gin or glu; met/leu or tyr or ile; phe/met or leu or tyr; ser/thr; thr/ser; trp/tyr; tyr/trp or phe; val/ile or leu. An alternative exemplary guideline uses the following six groups, each containing amino acids that are conservative substitutions for one another: 1) Alanine (A), Serine (S), Threonine (T); 2) Aspartic acid (D), Glutamic acid (E); 3) Asparagine (N), Glutamine (O); 4) Arginine (R), Lysine (I); 5) Isoleucine (I), Leucine (L), Methionine (M), Valine (V); and 6) Phenylalanine (F), Tyrosine (Y), Tryptophan (W); (see also, e.g., Creighton, *Proteins*, W. H. Freeman and Company (1984); Schultz and Schimer, *Principles of Protein Structure*, Springer-Vrlag (1979)). One of skill in the art will appreciate that the above-identified substitutions are not the only possible conservative substitutions. For example, for some purposes, one may regard all charged amino acids as conservative substitutions for each other whether they are positive or negative. In addition, individual substitutions, deletions or additions that alter, add or delete a single amino acid or a small percentage of amino acids in an encoded sequence can also be considered "conservatively modified variations."

The terms "mimetic" and "peptidomimetic" refer to a synthetic chemical compound that has substantially the same structural and/or functional characteristics of the polypeptides, e.g., translocation domains, ligand-binding domains, or chimeric receptors of the invention. The mimetic can be either entirely composed of synthetic, non-natural analogs of amino acids, or may be a chimeric molecule of partly natural peptide amino acids and partly non-natural analogs of amino acids. The mimetic can also incorporate any amount of natural amino acid conservative substitutions as long as such substitutions also do not substantially alter the mimetic's structure and/or activity.

As with polypeptides of the invention which are conservative variants, routine experimentation will determine whether a mimetic is within the scope of the invention, i.e., that its structure and/or function is not substantially altered. Polypeptide mimetic compositions can contain any combination of non-natural structural components, which are typically from three structural groups: a) residue linkage groups other than the natural amide bond ("peptide bond") linkages; b) non-natural residues in place of naturally occurring amino acid residues; or c) residues which induce secondary structural mimicry, i.e., to induce or stabilize a secondary structure, e.g., a beta turn, gamma turn, beta sheet, alpha helix conformation, and the like. A polypeptide can be characterized as a mimetic when all or some of its residues are joined by chemical means other than natural peptide bonds. Individual peptidomimetic residues can be joined by peptide bonds, other chemical bonds or coupling means, such as, e.g., glutaraldehyde, N-hydroxysuccinimide esters, bifunctional maleimides, N,N'-dicyclohexylcarbodiimide (DCC) or N,N'-diisopropylcarbodiimide (DIC). Linking groups that can be an alternative to the traditional amide bond ("peptide bond") linkages include, e.g., ketomethylene (e.g., —C(═O)—$CH_2$— for —C(═O)—NH—), aminomethylene ($CH_2$—NH), ethylene, olefin (CH═CH), ether ($CH_2$—O), thioether ($CH_2$—S), tetrazole ($CN_4$), thiazole, retroamide, thioamide, or ester (see, e.g., Spatola, *Chemistry and Biochemistry of Amino Acids, Peptides and Proteins*, Vol. 7, pp 267-357, "Peptide Backbone Modifications," Marcell Dekker, NY (1983)). A polypeptide can also be characterized as a mimetic by containing all or some non-natural residues in place of naturally occurring amino acid residues; non-natural residues are well described in the scientific and patent literature.

A "label" or a "detectable moiety" is a composition detectable by spectroscopic, photochemical, biochemical, immunochemical, or chemical means. For example, useful labels include $^{32}P$, fluorescent dyes, electron-dense reagents, enzymes (e.g., as commonly used in an ELISA), biotin, digoxigenin, or haptens and proteins which can be made detectable, e.g., by incorporating a radiolabel into the peptide or used to detect antibodies specifically reactive with the peptide.

A "labeled nucleic acid probe or oligonucleotide" is one that is bound, either covalently, through a linker or a chemical bond, or noncovalently, through ionic, van der Waals, electrostatic, or hydrogen bonds to a label such that the presence of the probe may be detected by detecting the presence of the label bound to the probe.

As used herein a "nucleic acid probe or oligonucleotide" is defined as a nucleic acid capable of binding to a target nucleic acid of complementary sequence through one or more types of chemical bonds, usually through complementary base pairing, usually through hydrogen bond formation. As used herein, a probe may include natural (i.e., A, G, C, or T) or modified bases (7-deazaguanosine, inosine, etc.). In addition, the bases in a probe may be joined by a linkage other than a phosphodiester bond, so long as it does not interfere with hybridization. Thus, for example, probes may be peptide nucleic acids in which the constituent bases are joined by peptide bonds rather than phosphodiester linkages. It will be understood by one of skill in the art that probes may bind target sequences lacking complete complementarity with the probe sequence depending upon the stringency of the hybridization conditions. The probes are optionally directly labeled as with isotopes, chromophores, lumiphores, chromogens, or indirectly labeled such as with biotin to which a streptavidin complex may later bind. By assaying for the presence or absence of the probe, one can detect the presence or absence of the select sequence or subsequence.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

A "promoter" is defined as an array of nucleic acid sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription. A "constitutive" promoter is a promoter that is active under most environmental and developmental conditions.

An "inducible" promoter is a promoter that is active under environmental or developmental regulation. The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

As used herein, "recombinant" refers to a polynucleotide synthesized or otherwise manipulated in vitro (e.g., "recombinant polynucleotide"), to methods of using recombinant polynucleotides to produce gene products in cells or other biological systems, or to a polypeptide ("recombinant protein") encoded by a recombinant polynucleotide. "Recombinant means" also encompass the ligation of nucleic acids having various coding regions or domains or promoter sequences from different sources into an expression cassette or vector for expression of, e.g., inducible or constitutive expression of a fusion protein comprising a translocation domain of the invention and a nucleic acid sequence amplified using a primer of the invention.

As used herein, a "stable cell line" refers to a cell line, which stably, i.e. over a prolonged period, expresses a heterologous nucleic sequence, i.e. a T1 R or G protein. In preferred embodiments, such stable cell lines will be produced by transfecting appropriate cells, typically mammalian cells, e.g. HEK-293 cells, with a linearized vector that contains a T1 R expression construct, i.e. T1 R1, T1R2 and/or T1 R3. Most preferably, such stable cell lines will be produced by co-transfecting two linearized plasmids that express hT1R1 and hT1R3 or hT1R2 and hT1R3 and an appropriate selection procedure to generate cell lines having these genes stably integrated therein. Most preferably, the cell line will also stably express a G protein such as $G_{\alpha 15}$.

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA).

The phrase "stringent hybridization conditions" refers to conditions under which a probe will hybridize to its target subsequence, typically in a complex mixture of nucleic acid, but to no other sequences. Stringent conditions are sequence dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point (Tm) for the specific sequence at a defined ionic strength pH. The Tm is the temperature (under defined ionic strength, pH, and nucleic concentration) at which 50% of the probes complementary to the target hybridize to the target sequence at equilibrium (as the target sequences are present in excess, at Tm, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 300 C for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, optionally 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C. Such hybridizations and wash steps can be carried out for, e.g., 1, 2, 5, 10, 15, 30, 60; or more minutes.

Nucleic acids that do not hybridize to each other under stringent conditions are still substantially related if the polypeptides that they encode are substantially related. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. Such hybridizations and wash steps can be carried out for, e.g., 1, 2, 5, 10, 15, 30, 60, or more minutes. A positive hybridization is at least twice background. Those of ordinary skill will readily recognize that alternative hybridization and wash conditions can be utilized to provide conditions of similar stringency.

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An exemplary immunoglobulin (antibody) structural unit comprises a tetramer. Each tetramer is composed of two identical pairs of polypeptide chains, each pair having one "light" (about 25 kDa) and one "heavy" chain (about 50-70 kDa). The N-terminus of each chain defines a variable region of about 100 to 110 or more amino acids primarily responsible for antigen recognition. The terms "variable light chain" (VL) and "variable heavy chain" (VH) refer to these light and heavy chains respectively.

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

An "anti-T1R" antibody is an antibody or antibody fragment that specifically binds a polypeptide encoded by a T1R gene, cDNA, or a subsequence thereof.

The term "immunoassay" is an assay that uses an antibody to specifically bind an antigen. The immunoassay is characterized by the use of specific binding properties of a particular antibody to isolate, target, and/or quantify the antigen.

The phrase "specifically (or selectively) binds" to an antibody or, "specifically (or selectively) immunoreactive with," when referring to a protein or peptide, refers to a binding reaction that is determinative of the presence of the protein in a heterogeneous population of proteins and other biologics. Thus, under designated immunoassay conditions, the specified antibodies bind to a particular protein at least two times the background and do not substantially bind in a significant amount to other proteins present in the sample. Specific binding to an antibody under such conditions may require an antibody that is selected for its specificity for a particular protein. For example, polyclonal antibodies raised to a T1R family member from specific species such as rat, mouse, or human can be selected to obtain only those polyclonal antibodies that are specifically immunoreactive with the T1R polypeptide or an immunogenic portion thereof and not with other proteins, except for orthologs or polymorphic variants and alleles of the T1R polypeptide. This selection may be achieved by subtracting out antibodies that cross-react with T1R molecules from other species or other T1R molecules. Antibodies can also be selected that recognize only T1R GPCR family members but not GPCRs from other families.

A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, *Antibodies, A Laboratory Manual*, (1988), for a description of immunoassay formats and conditions that can be used to determine specific immunoreactivity). Typically a specific or selective reaction will be at least twice background signal or noise and more typically more than 10 to 100 times background.

The phrase "selectively associates with" refers to the ability of a nucleic acid to "selectively hybridize" with another as defined above, or the ability of an antibody to "selectively (or specifically) bind to a protein, as defined above.

The term "expression vector" refers to any recombinant expression system for the purpose of expressing a nucleic acid sequence of the invention in vitro or in vivo, constitutively or inducibly, in any cell, including prokaryotic, yeast, fungal, plant, insect or mammalian cell. The term includes linear or circular expression systems. The term includes expression systems that remain episomal or integrate into the host cell genome. The expression systems can have the ability to self-replicate or not, i.e., drive only transient expression in a cell. The term includes recombinant expression "cassettes which contain only the minimum elements needed for transcription of the recombinant nucleic acid.

By "host cell" is meant a cell that contains an expression vector and supports the replication or expression of the expression vector. Host cells may be prokaryotic cells such as *E. coli*, or eukaryotic cells such as yeast, insect, amphibian, worm or mammalian cells such as CHO, Hela, HEK-293, and the like, e.g., cultured cells, explants, and cells in vivo.

Isolation and Expression of T1R Polypeptides

Isolation and expression of the T1Rs, or fragments or variants thereof, of the invention can be performed as described below. PCR primers can be used for the amplification of nucleic acids encoding taste receptor ligand-binding regions, and libraries of these nucleic acids can optionally be generated. Individual expression vectors or libraries of expression vectors can then be used to infect or transfect host cells for the functional expression of these nucleic acids or libraries. These genes and vectors can be made and expressed in vitro or in vivo. One of skill will recognize that desired phenotypes for altering and controlling nucleic acid expression can be obtained by modulating the expression or activity of the genes and nucleic acids (e.g., promoters, enhancers and the like) within the vectors of the invention. Any of the known methods described for increasing or decreasing expression or activity can be used. The invention can be practiced in conjunction with any method or protocol known in the art, which are well described in the scientific and patent literature.

The nucleic acid sequences of the invention and other nucleic acids used to practice this invention, whether RNA, cDNA, genomic DNA, vectors, viruses or hybrids thereof, may be isolated from a variety of sources, genetically engineered, amplified, and/or expressed recombinantly. Any recombinant expression system can be used, including, in addition to mammalian cells, e.g., bacterial, yeast, insect, or plant systems.

Alternatively, these nucleic acids can be synthesized in vitro by well-known chemical synthesis techniques, as described in, e.g., Carruthers, *Cold Spring Harbor Symp. Quant. Biol.* 47:411-418 (1982); Adams, *Am. Chem. Soc.* 105:661 (1983); Belousov, *Nucleic Acids Res.* 25:3440-3444 (1997); Frenkel, *Free Radic. Biol. Med.* 19:373-380 (1995); Blommers, *Biochemistry* 33:7886-7896 (1994); Narang, *Meth. Enzymol.* 68:90 (1979); Brown, *Meth. Enzymol.* 68:109 (1979); Beaucage, *Tetra. Lett.* 22:1859 (1981); U.S. Pat. No. 4,458,066. Double-stranded DNA fragments may then be obtained either by synthesizing the complementary strand and annealing the strands together under appropriate conditions, or by adding the complementary strand using DNA polymerase with an appropriate primer sequence.

Techniques for the manipulation of nucleic acids, such as, for example, for generating mutations in sequences, subcloning, labeling probes, sequencing, hybridization and the like are well described in the scientific and patent literature. See, e.g., Sambrook, ed., Molecular Cloning: a Laboratory manual (2nd ed.), Vols. 1-3, Cold Spring Harbor Laboratory (1989); Current Protocols in Molecular Biology, Ausubel, ed. John Wiley & Sons, Inc., New York (1997); Laboratory Techniques in Biochemistry and Molecular Biology: Hybridization With Nucleic Acid Probes, Part I, Theory and Nucleic Acid Preparation, Tijssen, ed. Elsevier, N.Y. (1993).

Nucleic acids, vectors, capsids, polypeptides, and the like can be analyzed and quantified by any of a number of general means well known to those of skill in the art. These include, e.g., analytical biochemical methods such as NMR, spectrophotometry, radiography, electrophoresis, capillary electrophoresis, high performance liquid chromatography (HPLC), thin layer chromatography (TLC), and hyperdiffusion chromatography, various immunological methods, e.g., fluid or gel precipitin reactions, immunodiffusion, immuno-electrophoresis, radioimmunoassays (RIAs), enzyme-linked immunosorbent assays (ELISAs), immuno-fluorescent assays, Southern analysis, Northern analysis, dot-blot analysis, gel electrophoresis (e.g., SDS-PAGE), RT-PCR, quantitative PCR, other nucleic acid or target or signal amplification methods, radiolabeling, scintillation counting, and affinity chromatography.

Oligonucleotide primers may be used to amplify nucleic acid fragments encoding taste receptor ligand-binding regions. The nucleic acids described herein can also be cloned or measured quantitatively using amplification techniques. Amplification methods are also well known in the art, and include, e.g., polymerase chain reaction, PCR (*PCR Protocols, a Guide to Methods and Applications*, ed. Innis. Academic Press, N.Y. (1990) and *PCR Strategies*, ed. Innis, Academic Press, Inc., N.Y. (1995), ligase chain reaction (LCR) (see, e.g., Wu, *Genomics*4:560 (1989); Landegren, *Science* 241:1077, (1988); Barringer, *Gene* 89:117 (1990)); transcription amplification (see, e.g., Kwoh, *Proc. Natl. Acad. Sci. USA* 86:1173 (1989)); and, self-sustained sequence replication (see, e.g., Guatelli, *Proc. Natl. Acad. Sci. USA* 87:1874 (1990)); Q Beta replicase amplification (see, e.g., Smith, *J. Clin. Microbiol.* 35:1477-1491 (1997)); automated Q-beta replicase amplification assay (see, e.g., Burg, *Mol. Cell. Probes* 10:257-271 (1996)) and other RNA polymerase mediated techniques (e.g., NASBA, Cangene, Mississauga, Ontario); see also Berger, *Methods Enzymol.* 152:307-316 (1987); Sambrook; Ausubel; U.S. Pat. Nos. 4,683,195 and 4,683,202; Sooknanan, *Biotechnology* 13:563-564 (1995). The primers can be designed to retain the original sequence of the "donor" 7-membrane receptor. Alternatively, the primers can encode amino acid residues that are conservative substitutions (e.g., hydrophobic for hydrophobic residue, see above discussion) or functionally benign substitutions (e.g., do not prevent plasma membrane insertion, cause cleavage by peptidase, cause abnormal folding of receptor, and the like). Once amplified, the nucleic acids, either individually or as libraries, may be cloned according to methods known in the art, if desired, into any of a variety of vectors using routine molecular biological methods; methods for cloning in vitro amplified nucleic acids are described, e.g., U.S. Pat. No. 5,426,039.

The primer pairs may be designed to selectively amplify ligand-binding regions of the T1R family members. These regions may vary for different ligands or tastants. Thus, what may be a minimal binding region for one tastant, may be too limiting for a second tastant. Accordingly, ligand-binding regions of different sizes comprising different extracellular domain structures may be amplified.

Paradigms to design degenerate primer pairs are well known in the art. For example, a COnsensus-DEgenerate Hybrid Oligonucleotide Primer (CODEHOP) strategy computer program is accessible as http://blocks.fhcrc.org/codehop.html, and is directly linked from the BlockMaker multiple sequence alignment site for hybrid primer prediction beginning with a set of related protein sequences, as known taste receptor ligand-binding regions (see, e.g., Rose, *Nucleic Acids Res.* 26:1628-1635 (1998); Singh, *Biotechniques* 24:318-319 (1998)).

Means to synthesize oligonucleotide primer pairs are well known in the art. "Natural" base pairs or synthetic base pairs can be used. For example, use of artificial nucleobases offers a versatile approach to manipulate primer sequence and generate a more complex mixture of amplification products. Various families of artificial nucleobases are capable of assuming multiple hydrogen bonding orientations through internal bond rotations to provide a means for degenerate molecular recognition. Incorporation of these analogs into a single position of a PCR primer allows for generation of a complex library of amplification products. See, e.g., Hoops, *Nucleic Acids Res.* 25:4866-4871 (1997). Nonpolar molecules can also be used to mimic the shape of natural DNA bases. A non-hydrogen-bonding shape mimic for adenine can replicate efficiently and selectively against a nonpolar shape mimic for thymine (see, e.g., Morales, *Nat. Struct. Biol.* 5:950-954 (1998)). For example, two degenerate bases can be the pyrimidine base 6H, 8H-3,4-dihydropyrimido[4,5-c][1,2]oxazin-7-one or the purine base N6-methoxy-2,6-diaminopurine (see, e.g., Hill, *Proc. Natl. Acad. Sci. USA* 95:4258-4263 (1998)). Exemplary degenerate primers of the invention incorporate the nucleobase analog 5'-Dimethoxytrityl-N-benzoyl-2'-deoxy-Cytidine,3'-[(2-cyanoethyl)-(N,N-diisopropyl)]-phosphoramidite (the term "P" in the sequences, see above). This pyrimidine analog hydrogen bonds with purines, including A and G residues.

Polymorphic variants, alleles, and interspecies homologs that are substantially identical to a taste receptor disclosed herein can be isolated using the nucleic acid probes described above. Alternatively, expression libraries can be used to clone T1 R polypeptides and polymorphic variants, alleles, and interspecies homologs thereof, by detecting expressed homologs immunologically with antisera or purified antibodies made against a T1R polypeptide, which also recognize and selectively bind to the T1R homolog.

Nucleic acids that encode ligand-binding regions of taste receptors may be generated by amplification (e.g., PCR) of appropriate nucleic acid sequences using degenerate primer pairs. The amplified nucleic acid can be genomic DNA from any cell or tissue or mRNA or cDNA derived from taste receptor-expressing cells.

In one embodiment, hybrid protein-coding sequences comprising nucleic acids encoding T1Rs fused to translocation sequences may be constructed. Also provided are hybrid T1 Rs comprising the translocation motifs and tastant-binding domains of other families of chemosensory receptors, particularly taste receptors. These nucleic acid sequences can be operably linked to transcriptional or translational control elements, e.g., transcription and translation initiation sequences, promoters and enhancers, transcription and translation terminators, polyadenylation sequences, and other sequences useful for transcribing DNA into RNA. In constitutive of recombinant expression cassettes, vectors, and transgenics, a promoter fragment can be employed to direct expression of the desired nucleic acid in all desired cells or tissues.

In another embodiment, fusion proteins may include C-terminal or N-terminal translocation sequences. Further, fusion proteins can comprise additional elements, e.g., for protein detection, purification, or other applications. Detection and purification facilitating domains include, e.g., metal chelating peptides such as polyhistidine tracts, histidine-tryptophan modules, or other domains that allow purification on immobilized metals; maltose binding protein; protein A domains that allow purification on immobilized immunoglobulin; or the domain utilized in the FLAGS extension/affinity purification system (Immunex Corp., Seattle, Wash.).

The inclusion of a cleavable linker sequences such as Factor Xa (see, e.g., Ottavi, *Biochimie* 80:289-293 (1998)), subtilisin protease recognition motif (see, e.g., Polyak, *Protein Eng.* 10:615-619 (1997)); enterokinase (Invitrogen, San Diego, Calif.), and the like, between the translocation domain (for efficient plasma membrane expression) and the rest of the newly translated polypeptide may be useful to facilitate purification. For example, one construct can include a polypeptide encoding a nucleic acid sequence linked to six histidine residues followed by a thioredoxin, an enterokinase cleavage site (see, e.g., Williams, *Biochemistry* 34:1787-1797 (1995)), and an C-terminal translocation domain. The histidine residues facilitate detection and purification while the enterokinase cleavage site provides a means for purifying the desired protein(s) from the remainder of the fusion protein. Technology pertaining to vectors encoding fusion proteins and application of fusion proteins are well described in the scientific and patent literature, see, e.g., Kroll, *DNA Cell. Biol.* 12:441-53 (1993).

Expression vectors, either as individual expression vectors or as libraries of expression vectors, comprising the ligand-binding domain encoding sequences may be introduced into a genome or into the cytoplasm or a nucleus of a cell and expressed by a variety of conventional techniques, well described in the scientific and patent literature. See, e.g., Roberts, *Nature* 328:731 (1987); Berger supra; Schneider, *Protein Expr. Purif.* 6435:10 (1995); Sambrook; Tijssen; Ausubel. Product information from manufacturers of biological reagents and experimental equipment also provide information regarding known biological methods. The vectors can be isolated from natural sources, obtained from such sources as ATCC or GenBank libraries, or prepared by synthetic or recombinant methods.

The nucleic acids can be expressed using expression cassettes, vectors or viruses which are stably or transiently expressed in cells (e.g., episomal expression systems). Selection markers can be incorporated into expression cassettes and vectors to confer a selectable phenotype on transformed cells and sequences. For example, selection markers can code for episomal maintenance and replication such that integration into the host genome is not required. For example, the marker may encode antibiotic resistance (e.g., chloramphenicol, kanamycin, G418, blasticidin, hygromycin) or herbicide resistance (e.g., chlorosulfuron or Basta) to permit selection of those cells transformed with the desired DNA sequences (see, e.g., Blondelet-Rouault, *Gene* 190:315-317 (1997); Aubrecht, *J. Pharmacol. Exp. Ther.* 281:992-997 (1997)). Because selectable marker genes conferring resistance to substrates like neomycin or hygromycin can only be utilized in tissue culture, chemoresistance genes are also used as selectable markers in vitro and in vivo.

A chimeric nucleic acid sequence may encode a T1R ligand-binding domain within any 7-transmembrane polypeptide. Because 7-transmembrane receptor polypeptides have similar primary sequences and secondary and tertiary structures, structural domains (e.g., extracellular domain, TM domains, cytoplasmic domain, etc.) can be readily identified by sequence analysis. For example, homology modeling, Fourier analysis and helical periodicity detection can identify and characterize the seven domains with a 7-transmembrane receptor sequence. Fast Fourier Transform (FFT) algorithms can be used to assess the dominant periods that characterize profiles of the hydrophobicity and variability of analyzed sequences. Periodicity detection enhancement and alpha helical periodicity index can be done as by, e.g., Donnelly, *Protein Sci.* 2:55-70 (1993). Other alignment and modeling algorithms are well known in the art, see, e.g., Peitsch, *Receptors Channels* 4:161-164 (1996); Kyte & Doolittle, *J. Med. Bio.,* 157:105-132 (1982); Cronet, *Protein Eng.* 6:59-64 (1993).

The present invention also includes not only the DNA and proteins having the specified nucleic and amino acid sequences, but also DNA fragments, particularly fragments of, e.g., 40, 60, 80, 100, 150, 200, or 250 nucleotides, or more, as well as protein fragments of, e.g., 10, 20, 30, 50, 70,100, or 150 amino acids, or more. Optionally, the nucleic acid fragments can encode an antigenic polypeptide, which is capable of binding to an antibody raised against a T1R family member. Further, a protein fragment of the invention can optionally be an antigenic fragment, which is capable of binding to an antibody raised against a T1R family member.

Also contemplated are chimeric proteins, comprising at least 10, 20, 30, 50, 70,100, or 150 amino acids, or more, of one of at least one of the T1 R polypeptides described herein, coupled to additional amino acids representing all or part of another GPCR, preferably a member of the 7 transmembrane superfamily. These chimeras can be made from the instant receptors and another GPCR, or they can be made by combining two or more of the present T1R receptors. In one embodiment, one portion of the chimera corresponds to or is derived from the extracellular domain of a T1R polypeptide of the invention. In another embodiment, one portion of the chimera corresponds to, or is derived from the extracellular domain and one or more of the transmembrane domains of a T1R polypeptide described herein, and the remaining portion or portions can come from another GPCR. Chimeric receptors are well known in the art, and the techniques for creating them and the selection and boundaries of domains or fragments of G protein-coupled receptors for incorporation therein are also well known. Thus, this knowledge of those skilled in the art can readily be used to create such chimeric receptors. The use of such chimeric receptors can provide, for example, a taste selectivity characteristic of one of the receptors specifically disclosed herein, coupled with the signal transduction characteristics of another receptor, such as a well known receptor used in prior art assay systems.

As noted above, such chimeras, analogous to the native T1R receptor, or native T1R receptor combination or association will bind to and/or be activated by molecules that normally affect sweet taste or umami taste. Functional chimeric T1R receptors or receptor combinations are molecules which when expressed alone or in combination with other T1Rs or other GPCRs (which may themselves be chimeric) bind to or which are activated by taste stimuli, particularly sweet (T1R2/3) or umami taste stimuli (T1R1/3). Molecules that elicit sweet taste include natural and artificial sweeteners such as sucrose, aspartame, xylitol, cyclamate, et al., Molecules that elicit umami taste include glutamate and glutamate analogs and other compounds that bind to native T1R1 and/or T1R3, such as 5'-nucleotides.

For example, a domain such as a ligand-binding domain, an extracellular domain, a transmembrane domain, a transmembrane domain, a cytoplasmic domain, an N-terminal domain, a C-terminal domain, or any combination thereof, can be covalently linked to a heterologous protein. For instance, an T1R extracellular domain can be linked to a heterologous GPCR transmembrane domain, or a heterologous GPCR extracellular domain can be linked to a T1R transmembrane domain. Other heterologous proteins of choice can be used; e.g., green fluorescent protein.

Also within the scope of the invention are host cells for expressing the T1Rs, fragments, chimeras or variants of the invention. To obtain high levels of expression of a cloned gene or nucleic acid, such as cDNAs encoding the T1Rs, fragments, or variants of the invention, one of skill typically subclones the nucleic acid sequence of interest into an expression vector that contains a strong promoter to direct transcription, a transcription/translation terminator, and if for a nucleic acid encoding a protein, a ribosome binding site for translational initiation. Suitable bacterial promoters are well known in the art and described, e.g., in Sambrook et al. However, bacterial or eukaryotic expression systems can be used.

Any of the well-known procedures for introducing foreign nucleotide sequences into host cells may be used. These include the use of calcium phosphate transfection, polybrene, protoplast fusion, electroporation, liposomes, microinjection, plasma vectors, viral vectors and any of the other well known methods for introducing cloned genomic DNA, cDNA, synthetic DNA or other foreign genetic material into a host cell (see, e.g., Sambrook et al.) It is only necessary that the particular genetic engineering procedure used be capable of successfully introducing at lest one nucleic acid molecule into the host cell capable of expressing the T1R, fragment, or variant of interest.

After the expression vector is introduced into the cells, the transfected cells are cultured under conditions favoring expression of the receptor, fragment, or variant of interest, which is then recovered from the culture using standard techniques. Examples of such techniques are well known in the art. See, e.g., WO 00/06593, which is incorporated by reference in a manner consistent with this disclosure.

Detection of T1R polypeptides

In addition to the detection of T1R genes and gene expression using nucleic acid hybridization technology, one can also use immunoassays to detect T1Rs, e.g., to identify taste receptor cells, and variants of T1R family members. Immunoassays can be used to qualitatively or quantitatively analyze the T1Rs. A general overview of the applicable technology can be found in Harlow & Lane, *Antibodies: A Laboratory Manual* (1988).

1. Antibodies to T1R Family Members

Methods of producing polyclonal and monoclonal antibodies that react specifically with a T1R family member are known to those of skill in the art (see, e.g., Coligan, *Current Protocols in Immunology (*1991); Harlow & Lane, supra; Goding, *Monoclonal Antibodies: Principles and Practice (*2d ed. 1986); and Kohler & Milstein, *Nature,* 256:495-497 (1975)). Such techniques include antibody preparation by selection of antibodies from libraries of recombinant antibodies in phage or similar vectors, as well as preparation of polyclonal and monoclonal antibodies by immunizing rabbits or mice (see, e.g., Huse et al., *Science,* 246:1275-1281 (1989); Ward et al., *Nature,* 341:544-546 (1989)).

A number of T1 R-comprising immunogens may be used to produce antibodies specifically reactive with a T1R family member. For example, a recombinant T1R polypeptide, or an antigenic fragment thereof, can be isolated as described herein. Suitable antigenic regions include, e.g., the consensus sequences that are used to identify members of the T1R family. Recombinant proteins can be expressed in eukaryotic or prokaryotic cells as described above, and purified as generally described above. Recombinant protein is the preferred immunogen for the production of monoclonal or polyclonal antibodies. Alternatively, a synthetic peptide derived from the sequences disclosed herein and conjugated to a carrier protein can be used an immunogen. Naturally occurring protein may also be used either in pure or impure form. The product is then injected into an animal capable of producing antibodies. Either monoclonal or polyclonal antibodies may be generated, for subsequent use in immunoassays to measure the protein.

Methods of production of polyclonal antibodies are known to those of skill in the art. For example, an inbred strain of mice (e.g., BALB/C mice) or rabbits is immunized with the protein using a standard adjuvant, such as Freund's adjuvant, and a standard immunization protocol. The animal's immune response to the immunogen preparation is monitored by taking test bleeds and determining the titer of reactivity to the T1R. When appropriately high titers of antibody to the immunogen are obtained, blood is collected from the animal and antisera are prepared. Further fractionation of the antisera to enrich for antibodies reactive to the protein can be done if desired (see Harlow & Lane, supra).

Monoclonal antibodies may be obtained by various techniques familiar to those skilled in the art. Briefly, spleen cells from an animal immunized with a desired antigen may be immortalized, commonly by fusion with a myeloma cell (see Kohler & Milstein, *Eur. J. Immunol.,* 6:511-519 (1976)). Alternative methods of immortalization include transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody or a binding fragment thereof by screening a DNA library from human B cells according to the general protocol outlined by Huse et al., *Science,* 246:1275-1281 (1989).

Monoclonal antibodies and polyclonal sera are collected and titered against the immunogen protein in an immunoassay, for example, a solid phase immunoassay with the immunogen immobilized on a solid support. Typically, polyclonal antisera with a titer of 104 or greater are selected and tested for their cross reactivity against non-T1R polypeptides, or even other T1R family members or other related proteins from other organisms, using a competitive binding immunoassay. Specific polyclonal antisera and monoclonal antibodies will usually bind with a Kd of at least about 0.1 mM, more usually at least about 1 pM, optionally at least about 0.1 pM or better, and optionally 0.01 pM or better.

Once T1R family member specific antibodies are available, individual T1R proteins and protein fragments can be detected by a variety of immunoassay methods. For a review of immunological and immunoassay procedures, see *Basic and Clinical Immunology* (Stites & Terr eds., 7th ed. 1991). Moreover, the immunoassays of the present invention can be performed in any of several configurations, which are reviewed extensively in Enzyme Immunoassay (Maggio, ed., 1980); and Harlow & Lane, supra.

2. Immunological Binding Assays

T1R proteins, fragments, and variants can be detected and/or quantified using any of a number of well-recognized immunological binding assays (see, e.g., U.S. Pat. Nos. 4,366,241; 4,376,110; 4,517,288; and 4,837,168). For a review of the general immunoassays, see also *Methods in Cell Biology: Antibodies in Cell Biology*, volume 37 (Asai, ed. 1993); *Basic and Clinical Immunology* (Stites & Terr, eds., 7th ed. 1991). Immunological binding assays (or immunoassays) typically use an antibody that specifically binds to a protein or antigen of choice (in this case a T1R family member or an antigenic subsequence thereof). The antibody (e.g., anti-T1R) may be produced by any of a number of means well known to those of skill in the art and as described above.

Immunoassays also often use a labeling agent to specifically bind to and label the complex formed by the antibody and antigen. The labeling agent may itself be one of the moieties comprising the antibody/antigen complex. Thus, the labeling agent may be a labeled T1R polypeptide or a labeled anti-T1R antibody. Alternatively, the labeling agent may be a third moiety, such a secondary antibody, that specifically binds to the antibody/T1R complex (a secondary antibody is typically specific to antibodies of the species from which the first antibody is derived). Other proteins capable of specifically binding immunoglobulin constant regions, such as protein A or protein G may also be used as the label agent. These proteins exhibit a strong non-immunogenic reactivity with immunoglobulin constant regions from a variety of species (see, e.g., Kronval et al., *J. Immunol.,* 111:1401-1406 (1973); Akerstrom et al., *J. Immunol.,* 135:2589-2542 (1985)). The labeling agent can be modified with a detectable moiety, such as biotin, to which another molecule can specifically bind, such as streptavidin. A variety of detectable moieties are well known to those skilled in the art.

Throughout the assays, incubation and/or washing steps may be required after each combination of reagents. Incubation steps can vary from about 5 seconds to several hours, optionally from about 5 minutes to about 24 hours. However, the incubation time will depend upon the assay format, antigen, volume of solution, concentrations, and the like. Usually, the assays will be carried out at ambient temperature, although they can be conducted over a range of temperatures, such as 10° C. to 40° C.

A. Non-Competitive Assay Formats

Immunoassays for detecting a T1R polypeptide in a sample may be either competitive or noncompetitive. Noncompetitive immunoassays are assays in which the amount of antigen is directly measured. In one preferred "sandwich" assay, for example, the anti-T1R antibodies can be bound directly to a solid substrate on which they are immobilized. These immobilized antibodies then capture the T1R polypeptide present in the test sample. The T1R polypeptide is thus immobilized is then bound by a labeling agent, such as a second T1R antibody bearing a label. Alternatively, the second antibody may lack a label, but it may, in turn, be bound by a labeled third antibody specific to antibodies of the species from which the second antibody is derived. The second or third antibody is typically modified with a detectable moiety, such as biotin, to which another molecule specifically binds, e.g., streptavidin, to provide a detectable moiety.

B. Competitive Assay Formats

In competitive assays, the amount of T1R polypeptide present in the sample is measured indirectly by measuring the amount of a known, added (exogenous) T1R polypeptide displaced (competed away) from an anti-T1R antibody by the unknown T1R polypeptide present in a sample. In one competitive assay, a known amount of T1R polypeptide is added to a sample and the sample is then contacted with an antibody that specifically binds to the T1R. The amount of exogenous T1R polypeptide bound to the antibody is inversely proportional to the concentration of T1R polypeptide present in the sample. In a particularly preferred embodiment, the antibody is immobilized on a solid substrate. The amount of T1R polypeptide bound to the antibody may be determined either by measuring the amount of T1R polypeptide present in a T1R/antibody complex, or alternatively by measuring the amount of remaining uncomplexed protein. The amount of T1R polypeptide may be detected by providing a labeled T1R molecule.

A hapten inhibition assay is another preferred competitive assay. In this assay the known T1R polypeptide is immobilized on a solid substrate. A known amount of anti-T1R antibody is added to the sample, and the sample is then contacted with the immobilized T1R. The amount of anti-T1R antibody bound to the known immobilized T1R polypeptide is inversely proportional to the amount of T1R polypeptide present in the sample. Again, the amount of immobilized antibody may be detected by detecting either the immobilized fraction of antibody or the fraction of the antibody that remains in solution. Detection may be direct where the antibody is labeled or indirect by the subsequent addition of a labeled moiety that specifically binds to the antibody as described above.

C. Cross-reactivity Determinations

Immunoassays in the competitive binding format can also be used for cross-reactivity determinations. For example, a protein at least partially encoded by the nucleic acid sequences disclosed herein can be immobilized to a solid support. Proteins (e.g., T1 R polypeptides and homologs) are added to the assay that compete for binding of the antisera to the immobilized antigen. The ability of the added proteins to compete for binding of the antisera to the immobilized protein is compared to the ability of the T1R polypeptide encoded by the nucleic acid sequences disclosed herein to compete with itself. The percent cross-reactivity for the above proteins is calculated, using standard calculations. Those antisera with less than 10% cross-reactivity with each of the added proteins listed above are selected and pooled. The cross-reacting antibodies are optionally removed from the pooled antisera by immunoabsorption with the added considered proteins, e.g., distantly related homologs. In addition, peptides comprising amino acid sequences representing conserved motifs that are used to identify members of the T1R family can be used in cross-reactivity determinations.

The immunoabsorbed and pooled antisera are then used in a competitive binding immunoassay as described above to compare a second protein, thought to be perhaps an allele or polymorphic variant of a T1R family member, to the immunogen protein (i.e., T1R polypeptide encoded by the nucleic acid sequences disclosed herein). In order to make this comparison, the two proteins are each assayed at a wide range of concentrations and the amount of each protein required to inhibit 50% of the binding of the antisera to the immobilized protein is determined. If the amount of the second protein required to inhibit 50% of binding is less than 10 times the amount of the protein encoded by nucleic acid sequences disclosed herein required to inhibit 50% of binding, then the second protein is said to specifically bind to the polyclonal antibodies generated to a T1R immunogen.

Antibodies raised against T1R conserved motifs can also be used to prepare antibodies that specifically bind only to GPCRs of the T1R family, but not to GPCRs from other families.

Polyclonal antibodies that specifically bind to a particular member of the T1R family can be made by subtracting out cross-reactive antibodies using other T1R family members. Species-specific polyclonal antibodies can be made in a similar way. For example, antibodies specific to human T1R1 can be made by, subtracting out antibodies that are cross-reactive with orthologous sequences, e.g., rat T1R1 or mouse T1R1.

D. Other Assay Formats

Western blot (immunoblot) analysis is used to detect and quantify the presence of T1R polypeptide in the sample. The technique generally comprises separating sample proteins by gel electrophoresis on the basis of molecular weight, transferring the separated proteins to a suitable solid support, (such as a nitrocellulose filter, a nylon filter, or derivatized nylon filter), and incubating the sample with the antibodies that specifically bind the T1R polypeptide. The anti-T1R polypeptide antibodies specifically bind to the T1R polypeptide on the solid support. These antibodies may be directly labeled or alternatively may be subsequently detected using labeled antibodies (e.g., labeled sheep anti-mouse antibodies) that specifically bind to the anti-T1R antibodies.

Other, assay formats include liposome immunoassays (LIA), which use liposomes designed to bind specific molecules (e.g., antibodies) and release encapsulated reagents or markers. The released chemicals are then detected according to standard techniques (see Monroe et al., *Amer. Clin. Prod. Rev.,* 5:34-41 (1986)).

E. Reduction of Non-specific Binding

One of skill in the art will appreciate that it is often desirable to minimize non-specific binding in immunoassays. Particularly, where the assay involves an antigen or antibody immobilized on a solid substrate it is desirable to minimize the amount of non-specific binding to the substrate. Means of reducing such non-specific binding are well known to those of skill in the art. Typically, this technique involves coating the substrate with a proteinaceous composition. In particular, protein compositions such as bovine serum albumin (BSA), nonfat powdered milk, and gelatin are widely used with powdered milk being most preferred.

F. Labels

The particular label or detectable group used in the assay is not a critical aspect of the invention, as long as it does not significantly interfere with the specific binding of the antibody used in the assay. The detectable group can be any material having a detectable physical or chemical property. Such detectable labels have been well developed in the field of immunoassays and, in general, most any label useful in such methods can be applied to the present invention. Thus, a label is any composition detectable by spectroscopic, photochemical, biochemical, immunochemical, electrical, optical, or chemical means. Useful labels in the present invention include magnetic beads (e.g., DYNABEADSTM), fluorescent dyes (e.g., fluorescein isothiocyanate, Texas red, rhodamine, and the like), radiolabels (e.g., $^{3}H$, $^{125}I$, $^{14}C$, $^{35}S$), enzymes (e.g., horseradish peroxidase, alkaline phosphates and others commonly used in an ELISA), and colorimetric labels such as colloidal gold or colored glass or plastic beads (e.g., polystyrene, polypropylene, latex, etc.).

The label may be coupled directly or indirectly to the desired component of the assay according to methods well known in the art. As indicated above, a wide variety of labels may be used, with the choice of label depending on sensitivity required, ease of conjugation with the compound, stability requirements, available instrumentation, and disposal provisions.

Non-radioactive labels are often attached by indirect means. Generally, a ligand molecule (e.g., biotin) is covalently bound to the molecule. The ligand then binds to another molecules (e.g., streptavidin) molecule, which is either inherently detectable or covalently bound to a signal system, such as a detectable enzyme, a fluorescent compound, or a chemiluminescent compound. The ligands and their targets can be used in any suitable combination with antibodies that recognize a T1R polypeptide, or secondary antibodies that recognize anti-T1R.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidotases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. For a review of various labeling or signal producing systems that may be used, see U.S. Pat. No. 4,391,904.

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence. The fluorescence may be detected visually, by means of photographic film, by the use of electronic detectors such as charge-coupled devices (CCDs) or photomultipliers and the like. Similarly, enzymatic labels may be detected by providing the appropriate substrates for the enzyme and detecting the resulting reaction product. Finally simple colorimetric labels may be detected simply by observing the color associated with the label. Thus, in various dipstick assays, conjugated gold often appears pink, while various conjugated beads appear the color of the bead.

Some assay formats do not require the use of labeled components. For instance, agglutination assays can be used to detect the presence of the target antibodies. In this case, antigen-coated particles are agglutinated by samples comprising the target antibodies. In this format, none of the components need be labeled and the presence of the target antibody is detected by simple visual inspection.

Detection of Modulators

Compositions and methods for determining whether a test compound specifically binds to a T1R receptor of the invention, both in vitro and in vivo, are described below. Many aspects of cell physiology can be monitored to assess the effect of ligand binding to a T1R polypeptide of the invention. These assays may be performed on intact cells expressing a chemosensory receptor, on permeabilized cells, or on membrane fractions produced by standard methods or in vitro de novo synthesized proteins.

In vivo, taste receptors bind tastants and initiate the transduction of chemical stimuli into electrical signals. An activated or inhibited G protein will in turn alter the properties of target enzymes, channels, and other effector proteins. Some examples are the activation of cGMP phosphodiesterase by transducin in the visual system, adenylate cyclase by the stimulatory G protein, phospholipase C by Gq and other cognate G proteins, and modulation of diverse channels by Gi and other G proteins. Downstream consequences can also be examined such as generation of diacyl glycerol and IP3 by phospholipase C, and in turn, for calcium mobilization by IP3.

The T1R proteins or polypeptides of the assay will preferably be selected from a polypeptide having the T1R polypeptide sequence selected from those disclosed in Example 1, or fragments or conservatively modified variants thereof. Optionally, the fragments and variants can be antigenic fragments and variants which bind to an anti-T1R antibody. Optionally, the fragments and variants can bind to or are activated by sweeteners or umami tastants.

Alternatively, the T1R proteins or polypeptides of the assay can be derived from a eukaryotic host cell and can include an amino acid subsequence having amino acid sequence identity to the T1R polypeptides disclosed in Example 1, or fragments or conservatively modified variants thereof. Generally, the amino acid sequence identity will be at least 35 to 50%, or optionally 75%, 85%, 90%, 95%, 96%, 97%, 98%, or 99%. Optionally, the T1R proteins or polypeptides of the assays can comprise a domain of a T1R protein, such as an extracellular domain, transmembrane region, transmembrane domain, cytoplasmic domain, ligand-binding domain, and the like. Further, as described above, the T1R protein or a domain thereof can be covalently linked to a heterologous protein to create a chimeric protein used in the assays described herein.

Modulators of T1R receptor activity are tested using T1R proteins or polypeptides as described above, either recombinant or naturally occurring. The T1R proteins or polypeptides can be isolated, co-expressed in a cell, co-expressed in a membrane derived from a cell, co-expressed in tissue or in an animal, either recombinant or naturally occurring. For example, tongue slices, dissociated cells from a tongue, transformed cells, or membranes can be used. Modulation can be tested using one of the in vitro or in vivo assays described herein.

For example, as disclosed in the experiment examples infra, it has been discovered that certain $5^1$ nucleotides, e.g., $5^1$ IMP or $5^1$ GMP, enhance the activity of L-glutamate to activate the umami taste receptor, or block the activation of the umami taste receptor by umami taste stimuli such as L-glutamate and L-aspartate.

1. In Vitro Binding Assays

Taste transduction can also be examined in vitro with soluble or solid state reactions, using the T1R polypeptides of the invention. In a particular embodiment, T1R ligand-binding domains can be used in vitro in soluble or solid state reactions to assay for ligand binding.

For instance, the T1R N-terminal domain is predicted to be involved in ligand binding. More particularly, the T1Rs belong to a GPCR sub-family that is characterized by large, approximately 600 amino acid, extracellular N-terminal segments. These N-terminal segments are thought to form the ligand-binding domains, and are therefore useful in biochemical assays to identify T1R agonists and antagonists. It is possible that the ligand-binding domain may be formed by additional portions of the extracellular domain, such as the extracellular loops of the transmembrane domain.

In vitro binding assays have been used with other GPCRs that are related to the T1Rs, such as the metabotropic glutamate receptors (see, e.g., Han and Hampson, *J. Biol. Chem.* 274:10008-10013 (1999)). These assays might involve displacing a radioactively or fluorescently labeled ligand, measuring changes in intrinsic fluorescence or changes in proteolytic susceptibility, etc.

Ligand binding to a hetero-multimeric complex of T1R polypeptides of the invention can be tested in solution, in a bilayer membrane, optionally attached to a solid phase, in a lipid monolayer, or in vesicles. Binding of a modulator can be tested using, e.g., changes in spectroscopic characteristics (e.g., fluorescence, absorbence, refractive index) hydrodynamic (e.g., shape), chromatographic, or solubility properties.

In another embodiment of the invention, a GTPγ$^{35}$S assay may be used. As described above, upon activation of a GPCR, the Gα subunit of the G protein complex is stimulated to exchange bound GDP for GTP. Ligand-mediated stimulation of G protein exchange activity can be measured in a biochemical assay measuring the binding of added radioactively labeled GTPγ$^{35}$S to the G protein in the presence of a putative ligand. Typically, membranes containing the chemosensory receptor of interest are mixed with a complex of G proteins. Potential inhibitors and/or activators and GTPγ$^{35}$S are added to the assay, and binding of GTPγ$^{35}$S to the G protein is measured. Binding can be measured by liquid scintillation counting or by any other means known in the art, including scintillation proximity assays (SPA). In other assays formats, fluorescently labeled GTPγ$^{35}$ S can be utilized.

2. Fluorescence Polarization Assays

In another embodiment, Fluorescence Polarization ("FP") based assays may be used to detect and monitor ligand binding. Fluorescence polarization is a versatile laboratory technique for measuring equilibrium binding, nucleic acid hybridization, and enzymatic activity. Fluorescence polarization assays are homogeneous in that they do not require a separation step such as centrifugation, filtration, chromatography, precipitation, or electrophoresis. These assays are done in real time, directly in solution and do not require an immobilized phase. Polarization values can be measured repeatedly and after the addition of reagents since measuring the polarization is rapid and does not destroy the sample. Generally, this technique can be used to measure polarization values of fluorophores from low picomolar to micromolar levels. This section describes how fluorescence polarization can be used in a simple and quantitative way to measure the binding of ligands to the T1R polypeptides of the invention.

When a fluorescently labeled molecule is excited with plane-polarized light, it emits light that has a degree of polarization that is inversely proportional to its molecular rotation. Large fluorescently labeled molecules remain relatively stationary during the excited state (4 nanoseconds in the case of fluorescein) and the polarization of the light remains relatively constant between excitation and emission. Small fluorescently labeled molecules rotate rapidly during the excited state and the polarization changes significantly between excitation and emission. Therefore, small molecules have low polarization values and large molecules have high polarization values. For example, a single-stranded fluorescein-labeled oligonucleotide has a relatively low polarization value but when it is hybridized to a complementary strand, it has a higher polarization value. When using FP to detect and monitor tastant-binding which may activate or inhibit the chemosensory receptors of the invention, fluorescence-labeled tastants or auto-fluorescent tastants may be used.

Fluorescence polarization (P) is defined as:

$$P = \frac{Int_{\Pi} - Int_{\perp}}{Int_{\Pi} + Int_{\perp}}$$

Where Π is the intensity of the emission light parallel to the excitation light plane and Int ⊥ is the intensity of the emission light perpendicular to the excitation light plane. P, being a ratio of light intensities, is a dimensionless number. For example, the Beacon ® and Beacon 2000™ System may be used in connection with these assays. Such systems typically express polarization in millipolarization units (1 Polarization Unit=1000 mP Units).

The relationship between molecular rotation and size is described by the Perrin equation and the reader is referred to Jolley, M. E. (1991) in Journal of Analytical Toxicology, pp. 236-240, which gives a thorough explanation of this equation. Summarily, the Perrin equation states that polarization is directly proportional to the rotational relaxation time, the time that it takes a molecule to rotate through an angle of approximately 68.5° Rotational relaxation time is related to viscosity (η), absolute temperature (T), molecular volume (V), and the gas constant (R) by the following equation:

$$\text{Rotational Relaxation Time} = \frac{3\eta V}{RT}$$

The rotational relaxation time is small (≈1 nanosecond) for small molecules (e.g. fluorescein) and large (≈100 nanoseconds) for large molecules (e.g. immunoglobulins). If viscosity and temperature are held constant, rotational relaxation time, and therefore polarization, is directly related to the molecular volume. Changes in molecular volume may be due to interactions with other molecules, dissociation, polymerization, degradation, hybridization, or conformational changes of the fluorescently labeled molecule. For example, fluorescence polarization has been used to measure enzymatic cleavage of large fluorescein labeled polymers by proteases, DNases, and RNases. It also has been used to measure equilibrium binding for protein/protein interactions, antibody/antigen binding, and protein/DNA binding.

A. Solid State and Soluble High Throughput Assays

In yet another embodiment, the invention provides soluble assays using a hetero-oligomeric T1R polypeptide complex; or a cell or tissue co-expressing T1R polypeptides. Preferably, the cell will comprise a cell line that stably co-expresses a functional T1R1/T1R3 (umami) taste receptor or T1R2/T1R3 (sweet) taste receptor. In another embodiment, the invention provides solid phase based in vitro assays in a high throughput format, where the T1R polypeptides, or cell or tissue expressing the T1R polypeptides is attached to a solid phase substrate or a taste stimulating compound and contacted with a T1R receptor, and binding detected using an appropriate tag or antibody raised against the T1R receptor.

In the high throughput assays of the invention, it is possible to screen up to several thousand different modulators or ligands in a single day. In particular, each well of a microtiter plate can be used to run a separate assay against a selected potential modulator, or, if concentration or incubation time effects are to be observed, every 5-10 wells can test a single modulator. Thus, a single standard microtiter plate can assay about 100 (e.g., 96) modulators. If 1536 well plates are used, then a single plate can easily assay from about 1000 to about 1500 different compounds. It is also possible to assay multiple compounds in each plate well. It is possible to assay several different plates per day; assay screens for up to about 6,000-20,000 different compounds is possible using the integrated systems of the invention. More recently, microfluidic approaches to reagent manipulation have been developed.

The molecule of interest can be bound to the solid state component, directly or indirectly, via covalent or non-covalent linkage, e.g., via a tag. The tag can be any of a variety of components. In general, a molecule which binds the tag (a tag binder) is fixed to a solid support, and the tagged molecule of interest (e.g., the taste transduction molecule of interest) is attached to the solid support by interaction of the tag and the tag binder.

A number of tags and tag binders can be used, based upon known molecular interactions well described in the literature. For example, where a tag has a natural binder, for example, biotin, protein A, or protein G, it can be used in conjunction with appropriate tag binders (avidin, streptavidin, neutravidin, the Fc region of an immunoglobulin, etc.). Antibodies to molecules with natural binders such as biotin are also widely available and appropriate tag binders (see, SIGMA Immunochemicals 1998 catalogue SIGMA, St. Louis Mo.).

Similarly, any haptenic or antigenic compound can be used in combination with an appropriate antibody to form a tag/tag binder pair. Thousands of specific antibodies are commercially available and many additional antibodies are described in the literature. For example, in one common configuration, the tag is a first antibody and the tag binder is a second antibody which recognizes the first antibody. In addition to antibody-antigen interactions, receptor-ligand interactions are also appropriate as tag and tag-binder pairs. For example, agonists and antagonists of cell membrane receptors (e.g., cell receptor-ligand interactions such as transferrin, c-kit, viral receptor ligands, cytokine receptors, chemokine receptors, interleukin receptors, immunoglobulin receptors and antibodies, the cadherein family, the integrin family, the selectin family, and the like; see, e.g., Pigott & Power, The Adhesion Molecule Facts Book I (1993)). Similarly, toxins and venoms, viral epitopes, hormones (e.g., opiates, steroids, etc.), intracellular receptors (e.g., which mediate the effects of various small ligands, including steroids, thyroid hormone, retinoids and vitamin D; peptides), drugs, lectins, sugars, nucleic acids (both linear and cyclic polymer configurations), oligosaccharides, proteins, phospholipids and antibodies can all interact with various cell receptors.

Synthetic polymers, such as polyurethanes, polyesters, polycarbonates, polyureas, polyamides, polyethyleneimines, polyarylene sulfides, polysiloxanes, polyimides, and polyacetates can also form an appropriate tag or tag binder. Many other tag/tag binder pairs are also useful in assay systems described herein, as would be apparent to one of skill upon review of this disclosure.

Common linkers such as peptides, polyethers, and the like can also serve as tags, and include polypeptide sequences, such as poly gly sequences of between about 5 and 200 amino acids. Such flexible linkers are known to persons of skill in the art. For example, poly(ethelyne glycol) linkers are available from Shearwater Polymers, Inc. Huntsville, Ala. These linkers optionally have amide linkages, sulfhydryl linkages, or heterofunctional linkages.

Tag binders are fixed to solid substrates using any of a variety of methods currently available. Solid substrates are commonly derivatized or functionalized by exposing all or a portion of the substrate to a chemical reagent which fixes a chemical group to the surface which is reactive with a portion of the tag binder. For example, groups which are suitable for attachment to a longer chain portion would include amihes, hydroxyl, thiol, and carboxyl groups. Aminoalkylsilanes and hydroxyalkylsilanes can be used to functionalize a variety of surfaces, such as glass surfaces. The constitutive of such solid phase biopolymer arrays is well described in the literature. See, e.g., Merrifield, *J. Am. Chem. Soc.,* 85:2149-2154 (1963) (describing solid phase synthesis of, e.g., peptides); Geysen et al., *J. Immun. Meth.,* 102:259-274 (1987) (describing synthesis of solid phase components on pins); Frank & Doring, *Tetrahedron,* 44:60316040 (1988) (describing synthesis of various peptide sequences on cellulose disks); Fodor et al., *Science,* 251:767-777 (1991); Sheldon et al., *Clinical Chemistry,* 39(4):718-719 (1993); and Kozal et al., *Nature Medicine,* 2(7):753759 (1996) (all describing arrays of biopolymers fixed to solid substrates). Non-chemical approaches for fixing tag binders to substrates include other common methods, such as heat, cross-linking by UV radiation, and the like.

3. Cell-Based Assays

In a preferred embodiment of treatment, a combination of T1 R proteins or polypeptides are transiently or stably co-expressed in a eukaryotic cell either in unmodified forms or as chimeric, variant or truncated receptors with or preferably without a heterologous, chaperone sequence that facilitates its maturation and targeting through the secretory pathway. Such T1R polypeptides can be expressed in any eukaryotic cell, such as HEK-293 cells. Preferably, the cells comprise a functional G protein, e.g., Gα15 or the chimeric G protein previously identified, or another G protein that is capable of coupling the chimeric receptor to an intracellular signaling pathway or to a signaling protein such as phospholipase C. Also, preferably a cell will be produced that stably co-expresses T1R1/T1R3 or T1 R2/T1 R3 as such cells have been found (as shown in the experimental examples) to exhibit enhanced responses to taste stimuli (relation to cells that transiently express the same T1 R combination). Activation of T1 R receptors in such cells can be detected using any standard method, such as by detecting changes in intracellular calcium by detecting Fluo-4 dependent fluorescence in the cell. Such an assay is the basis of the experimental findings presented in this application.

Activated GPCR receptors often are substrates for kinases that phosphorylate the C-terminal tail of the receptor (and possibly other sites as well). Thus, activators will promote the transfer of $^{32}P$ from radiolabeled ATP to the receptor, which can be assayed with a scintillation counter. The phosphorylation of the C-terminal tail will promote the binding of arrestin-like proteins and will interfere with the binding of G proteins. For a general review of GPCR signal transduction and methods of assaying signal transduction, see, e.g., *Methods in Enzymology*, vols. 237 and 238 (1994) and volume 96 (1983); Bourne et al., *Nature,* 10:349:117-27 (1991); Bourne et al., *Nature,* 348:125-32 (1990); Pitcher et al., *Annu. Rev. Biochem.,* 67:653-92 (1998).

T1R modulation may be assayed by comparing the response of T1R polypeptides treated with a putative T1R modulator to the response of an untreated control sample or a sample containing a known "positive" control. Such putative T1R modulators can include molecules that either inhibit or activate T1R polypeptide activity. In one embodiment, control samples (untreated with activators or inhibitors) are assigned a relative T1R activity value of 100. Inhibition of a T1R polypeptide is achieved when the T1R activity value relative to the control is about 90%, optionally 50%, optionally 25-0%. Activation of a T1R polypeptide is achieved when the T1R activity value relative to the control is 110%, optionally 150%, 200-500%, or 1000-2000%.

Changes in ion flux may be assessed by determining changes in ionic polarization (i.e., electrical potential) of the cell or membrane expressing a T1R polypeptide. One means to determine changes in cellular polarization is by measuring changes in current (thereby measuring changes in polarization) with voltage-clamp and patch-clamp techniques (see, e.g., the "cell-attached" mode, the "inside-out" mode, and the "whole cell" mode, e.g., Ackerman et al., *New Engl. J*

*Med.,* 336:1575-1595 (1997)). Whole cell currents are conveniently determined using the standard. Other known assays include: radiolabeled ion flux assays and fluorescence assays using voltage-sensitive dyes (see, e.g., Vestergarrd-Bogind et al., *J. Membrane Biol.,* 88:67-75 (1988); Gonzales & Tsien, *Chem. Biol.,* 4:269-277 (1997); Daniel et al., *J. Pharmacol. Meth.,* 25:185-193 (1991); Holevinsky et al., *J. Membrane Biology,* 137:59-70 (1994)).

The effects of the test compounds upon the function of the polypeptides can be measured by examining any of the parameters described above. Any suitable physiological change that affects GPCR activity can be used to assess the influence of a test compound on the polypeptides of this invention. When the functional consequences are determined using intact cells or animals, one can also measure a variety of effects such as transmitter release, hormone release, transcriptional changes to both known and uncharacterized genetic markers (e.g., northern blots), changes in cell metabolism such as cell growth or pH changes, and changes in intracellular second messengers such as $Ca^{2+}$, IP3, cGMP, or cAMP.

Preferred assays for GPCRs include cells that are loaded with ion or voltage sensitive dyes to report receptor activity. Assays for determining activity of such receptors can also use known agonists and antagonists for other G protein-coupled receptors as controls to assess activity of tested compounds. In assays for identifying modulatory compounds (e.g., agonists, antagonists), changes in the level of ions in the cytoplasm or membrane voltage will be monitored using an ion sensitive or membrane voltage fluorescent indicator, respectively. Among the ion-sensitive indicators and voltage probes that may be employed are those disclosed in the Molecular Probes 1997 Catalog. For G protein-coupled receptors, promiscuous G proteins such as Gα15 and Gα16 can be used in the assay of choice (Wilkie et al., *Proc. Nat'l Acad. Sci.,* 88:10049-10053 (1991)).

Receptor activation initiates subsequent intracellular events, e.g., increases in second messengers. Activation of some G protein-coupled receptors stimulates the formation of inositol triphosphate (IP3) through phospholipase C-mediated hydrolysis of phosphatidylinositol (Berridge & Irvine, *Nature,* 312:315-21 (1984)). IP3 in turn stimulates the release of intracellular calcium ion stores. Thus, a change in cytoplasmic calcium ion levels, or a change in second messenger levels such as IP3 can be used to assess G protein-coupled receptor function. Cells expressing such G protein-coupled receptors may exhibit increased cytoplasmic calcium levels as a result of contribution from both calcium release from intracellular stores and extracellular calcium entry via plasma membrane ion channels.

In a preferred embodiment, T1R polypeptide activity is measured by stably or transiently co-expressing T1R genes, preferably stably, in a heterologous cell with a promiscuous G protein that links the receptor to a phospholipase C signal transduction pathway (see Offermanns & Simon, *J. Biol. Chem.,* 270:15175-15180 (1995)). In a preferred embodiment, the cell line is HEK-293 (which does not normally express T1R genes) and the promiscuous G protein is Gα15 (Offermanns & Simon, supra). Modulation of taste transduction is assayed by measuring changes in intracellular $Ca^{2+}$ levels, which change in response to modulation of the T1R signal transduction pathway via administration of a molecule that associates with T1R polypeptides. Changes in $Ca^{2+}$ levels are optionally measured using fluorescent $Ca^{2+}$ indicator dyes and fluorometric imaging.

In another embodiment, phosphatidyl inositol (PI) hydrolysis can be analyzed according to U.S. Pat. No. 5,436,128, herein incorporated by reference. Briefly, the assay involves labeling of cells with 3H-myoinositol for 48 or more hrs. The labeled cells are treated with a test compound for one hour. The treated cells are lysed and extracted in chloroform-methanol-water after which the inositol phosphates were separated by ion exchange chromatography and quantified by scintillation counting. Fold stimulation is determined by calculating the ratio of cpm in the presence of agonist, to cpm in the presence of buffer control. Likewise, fold inhibition is determined by calculating the ratio of cpm in the presence of antagonist, to cpm in the presence of buffer control (which may or may not contain an agonist).

Other receptor assays can involve determining the level of intracellular cyclic nucleotides, e.g., cAMP or cGMP. In cases where activation of the receptor results in a decrease in cyclic nucleotide levels, it may be preferable to expose the cells to agents that increase intracellular cyclic nucleotide levels, e.g., forskolin, prior to adding a receptor-activating compound to the cells in the assay. In one embodiment, the changes in intracellular cAMP or cGMP can be measured using immunoassays. The method described in Offermanns & Simon, *J. Bio. Chem.,* 270:15175-15180 (1995), may be used to determine the level of cAMP. Also, the method described in Felley-Bosco et al., *Am. J. Resp. Cell and Mol. Biol.,* 11:159-164 (1994), may be used to determine the level of cGMP. Further, an assay kit for measuring cAMP and/or cGMP is described in U.S. Pat. No. 4,115,538, herein incorporated by reference.

In another embodiment, transcription levels can be measured to assess the effects of a test compound on signal transduction. A host cell containing T1 R polypeptides of interest is contacted with a test compound for a sufficient time to effect any interactions, and then the level of gene expression is measured. The amount of time to effect such interactions may be empirically determined, such as by running a time course and measuring the level of transcription as a function of time. The amount of transcription may be measured by using any method known to those of skill in the art to be suitable. For example, mRNA expression of the protein of interest may be detected using northern blots or their polypeptide products may be identified using immunoassays. Alternatively, transcription based assays using reporter gene may be used as described in U.S. Pat. No. 5,436,128, herein incorporated by reference. The reporter genes can be, e.g., chloramphenicol acetyltransferase, luciferase, beta-galactosidase beta-lactamase and alkaline phosphatase. Furthermore, the protein of interest can be used as an indirect reporter via attachment to a second reporter such as green fluorescent protein (see, e.g., Mistili & Spector, *Nature Biotechnology,* 15:961-964 (1997)).

The amount of transcription is then compared to the amount of transcription in either the same cell in the absence of the test compound, or it may be compared with the amount of transcription in a substantially identical cell that lacks the T1R polypeptide(s) of interest. A substantially identical cell may be derived from the same cells from which the recombinant cell was prepared but which had not been modified by introduction of heterologous DNA. Any difference in the amount of transcription indicates that the test compound has in some manner altered the activity of the T1R polypeptides of interest.

4. Transgenic Non-human Animals Expressing Chemosensory Receptors

Non-human animals expressing a combination of T1R taste receptor sequences of the invention can also be used for receptor assays. Such expression can be used to determine whether a test compound specifically binds to a mammalian taste transmembrane receptor complex in vivo by contacting a non-human animal stably or transiently transfected with nucleic acids encoding chemosensory receptors or ligand-binding regions thereof with a test compound and determining whether the animal reacts to the test compound by specifically binding to the receptor polypeptide complex.

Animals transfected or infected with the vectors of the invention are particularly useful for assays to identify and characterize taste stimuli that can bind to a specific or sets of receptors. Such vector-infected animals expressing human taste receptor sequences can be used for in vivo screening of taste stimuli and their effect on, e.g., cell physiology (e.g., on taste neurons), on the CNS, or behavior. Alternatively, stable cell lines that express a T1R or combination thereof, can be used as nucleic transfer donors to produced cloned transgenic animals that stably express a particular T1R or combination. Methods of using nucleic transfer to produce cloned animals that express a desired heterologous DNA are the subject of several issued U.S. patents granted to the University of Massachusetts (licensed to Advanced Cell Technology, Inc.) and Roslin Institute (licensed to Geron Corp.).

Means to infect/express the nucleic acids and vectors, either individually or as libraries, are well known in the art. A variety of individual cell, organ, or whole animal parameters can be measured by a variety of means. The T1 R sequences of the invention can be for example co-expressed in animal taste tissues by delivery with an infecting agent, e.g., adenovirus expression vector.

The endogenous taste receptor genes can remain functional and wild-type (native) activity can still be present. In other situations, where it is desirable that all taste receptor activity is by the introduced exogenous hybrid receptor, use of a knockout line is preferred. Methods for the constitutive of non-human transgenic animals, particularly transgenic mice, and the selection and preparation of recombinant constructs for generating transformed cells are well known in the art.

Constitutive of a "knockout" cell and animal is based on the premise that the level of expression of a particular gene in a mammalian cell can be decreased or completely abrogated by introducing into the genome a new DNA sequence that serves to interrupt some portion of the DNA sequence of the gene to be suppressed. Also, "gene trap insertion" can be used to disrupt a host gene, and mouse embryonic stem (ES) cells can be used to produce knockout transgenic animals (see, e.g., Holzschu, *Transgenic Res* 6:97-106 (1997)). The insertion of the exogenous is typically by homologous recombination between complementary nucleic acid sequences. The exogenous sequence is some portion of the target gene to be modified, such as exonic, intronic or transcriptional regulatory sequences, or any genomic sequence which is able to affect the level of the target gene's expression; or a combination thereof. Gene targeting via homologous recombination in pluripotential embryonic stem cells allows one to modify precisely the genomic sequence of interest. Any technique can be used to create, screen for, propagate, a knockout animal, e.g., see Bijvoet, *Hum. Mol. Genet.* 7:53-62 (1998); Moreadith, *J. Mol. Med.* 75:208-216 (1997); Tojo, *Cytotechnology* 19:161-165 (1995); Mudgett, *Methods Mol. Biol.* 48:167-184 (1995); Longo, *Transgenic Res.* 6:321-328 (1997); U.S. Pat. Nos. 5,616,491; 5,464,764; 5,631,153; 5,487,992; 5,627,059; 5,272,071; WO 91/09955; WO93/09222; WO 96/29411; WO 95/31560; WO 91/12650.

The nucleic acids of the invention can also be used as reagents to produce "knockout" human cells and their progeny. Likewise, the nucleic acids of the invention can also be used as reagents to produce "knock-ins" in mice. The human or rat T1R gene sequences can replace the orthologous T1R in the mouse genome. In this way, a mouse expressing a human or rat T1R is produced. This mouse can then be used to analyze the function of human or rat T1Rs, and to identify ligands for such T1Rs.

a. Modulators

The compounds tested as modulators of a T1R family member can be any small chemical compound, or a biological entity, such as a protein, nucleic acid or lipid. Examples thereof include $5^1$ IMP and $5^1$ GMP. Essentially any chemical compound can be used as a potential modulator or ligand in the assays of the invention, although most often compounds that are soluble in aqueous solutions are tested. Assays can be designed to screen large chemical libraries by automating the assay steps and providing compounds from any convenient source; these assays are typically run in parallel (e.g., in microtiter formats on microtiter plates in robotic assays). It will be appreciated that chemical libraries can be synthesized by one of many chemical reactions (e.g. Senomyx proprietary chemistries). Additionally, there are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs, Switzerland) and the like.

In one preferred embodiment, high throughput screening methods involve providing a combinatorial chemical or peptide library containing a large number of potential taste affecting compounds (potential modulator or ligand compounds). Such "combinatorial chemical libraries" or "ligand libraries" are then screened in one or more assays, as described herein, to identify those library members (particular chemical species or subclasses) that display a desired characteristic activity. The compounds thus identified can serve as conventional "lead compounds" or can themselves be used as potential or actual taste modulators.

Preferably, such libraries will be screened against cells or cell lines that stably express a T1R or combination of T1Rs, i.e. T1R1/T1R3 or T1R2/T1R3 and preferably a suitable G protein, e.g. $G_{\alpha 15}$. As shown in the examples infra, such stable cell lines exhibit very pronounced responses to taste stimuli, e.g. umami or sweet taste stimuli. However, cells and cell lines that transiently express one or more T1Rs may also be used in such assays.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Thousands to millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka, *Int. J. Pept. Prot. Res.,* 37:487-493 (1991) and Houghton et al., *Nature,* 354:84-88 (1991)). Other chemistries for generating chemical diversity libraries can also be used. Such chemistries include, but are not limited to: peptoids (e.g., PCT Publication No. WO 91/19735), encoded peptides (e.g., PCT Publication WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., *Proc. Nat. Acad. Sci.,* 90:6909-6913 (1993)), vinylogous polypeptides (Hagihara et a., *J. Amer. Chem. Soc.,* 114:6568 (1992)), nonpeptidal peptidomimetics with glucose scaffolding (Hirschmann et al., *J. Amer. Chem. Soc.,* 114:9217-9218 (1992)), analogous organic syntheses of small compound libraries (Chen et al., *J. Amer. Chem. Soc.,* 116:2661 (1994)), oligocarbamates (Cho et al., *Science,* 261:1303 (1993)), peptidyl phosphonates (Campbell et al., *J. Org. Chem.,* 59:658 (1994)), nucleic acid libraries (Ausubel, Berger and Sambrook, all supra), peptide nucleic acid libraries (U.S. Pat. No. 5,539,083), antibody libraries (Vaughn et al., *Nature Biotechnology,* 14(3):309-314 (1996) and PCT/US96/10287), carbohydrate libraries (Liang et al., *Science,* 274:1520-1522 (1996) and U.S. Pat. No. 5,593,853), small organic molecule libraries (benzodiazepines, Baum, C&EN, January 18, page 33 (1993); thiazolidinones and metathiazanones, U.S. Pat. No. 5,549,974; pynrolidines, U.S. Pat. Nos. 5,525,735 and 5,519,134; morpholino compounds, U.S. Pat. No. 5,506,337; benzodiazepines, U.S. Pat. No. 5,288,514, and the like).

Devices for the preparation of combinatorial libraries are commercially available (see, e.g., 357 MPS, 390 MPS (Advanced Chem Tech, Louisville Ky.), Symphony (Rainin, Woburn, Mass.), 433A (Applied Biosystems, Foster City, Calif.), 9050 Plus (Millipore, Bedford, Mass.)). In addition, numerous combinatorial libraries are themselves commercially available (see, e.g., ComGenex, Princeton, N.J.; Tripos, Inc., St. Louis, Mo.; 3D Pharmaceuticals, Exton, Pa.; Martek Biosciences; Columbia, Md.; etc.).

In one aspect of the invention, the T1R modulators can be used in any food product, confectionery, pharmaceutical composition, or ingredient thereof to thereby modulate the taste of the product, composition, or ingredient in a desired manner. For instance, T1R modulators that enhance sweet taste sensation can be added to sweeten a product or composition; T1R modulators that enhance umami taste sensation can be added to foods to increase savory tastes. Alternatively, T1R antagonists can be used to block sweet and/or umami taste.

b. Kits

T1R genes and their homologs are useful tools for identifying chemosensory receptor cells, for forensics and paternity determinations, and for examining taste transduction. T1R family member-specific reagents that specifically hybridize to T1R nucleic acids, such as T1R probes and primers, and T1R specific reagents that specifically bind to a T1R polypeptide, e.g., T1R antibodies are used to examine taste cell expression and taste transduction regulation.

Nucleic acid assays for the presence of DNA and RNA for a T1R family member in a sample include numerous techniques are known to those skilled in the art, such as southern analysis, northern analysis, dot blots, RNase protection, S1 analysis, amplification techniques such as PCR, and in situ hybridization. In in situ hybridization, for example, the target nucleic acid is liberated from its cellular surroundings in such as to be available for hybridization within the cell while preserving the cellular morphology for subsequent interpretation and analysis. The following articles provide an overview of the art of in situ hybridization: Singer et al., *Biotechniques,* 4:230250 (1986); Haase et al., *Methods in Virology*, vol. VII, pp. 189-226 (1984); and *Nucleic Acid Hybridization: A Practical Approach* (Names et al., eds. 1987). In addition, a T1R polypeptide can be detected with the various immunoassay techniques described above. The test sample is typically compared to both a positive control (e.g., a sample expressing a recombinant T1R polypeptide) and a negative control.

The present invention also provides for kits for screening for modulators of T1R family members. Such kits can be prepared from readily available materials and reagents. For example, such kits can comprise any one or more of the following materials: T1R nucleic acids or proteins, reaction tubes, and instructions for testing T1R activity. Optionally, the kit contains a biologically active T1R receptor or cell line that stably or transiently expresses a biologically active T1R containing taste receptor. A wide variety of kits and components can be prepared according to the present invention, depending upon the intended user of the kit and the particular needs of the user.

EXAMPLES

While the invention has been described in detail supra, the following examples are provided to illustrate preferred embodiments. These examples are intended to be illustrative and not limitative of the scope of the invention.

In the protein sequences presented herein, the one-letter code X or Xaa refers to any of the twenty common amino acid residues. In the DNA sequences presented herein, the one letter codes N or n refers to any of the of the four common nucleotide bases, A, T, C, or G.

Example 1

Production of Intronless hT1R Expression Constructs

Intronless hT1R expression constructs were cloned by a combination of cDNA-based and genomic DNA-based methods. To generate the full-length hT1R1 expression construct, two 5' coding exons identified in a cloned hT1R1 interval (accession # AL159177) were combined by PCR-overlap, and then joined to a 5'-truncated testis cDNA clone. The hT1R2 expression construct was generated from a partially sequenced hT1R2 genomic interval. Two missing hT1R2 5' exons were identified by screening shotgun libraries of the cloned genomic interval using probes derived from the corresponding rat coding sequence. Coding exons were then combined by PCR-overlap to produce the full-length expression construct. The hT1R3 expression construct was generated by PCR-overlap from a sequenced hT1R3 genomic interval (accession # AL139287). Rat TI R3 was isolated from a rat taste tissue-derived cDNA library using an rT1R3 exon fragment generated by hT1R3-based degenerate PCR. The partial hT1R1 cDNA, rT1R2 cDNA, and partial hT1 R2 genomic sequences were obtained from Dr. Charles Zuker (University of California, San Diego).

The nucleic acid and amino acid sequences for the above-identified T1R cloned sequences as well as other full-length and partial T1 R sequences are set forth below:

Amino Acid Sequence rT1R3
MPGLAILGLSLAAFLELGMGSSLCLSQQFKAQGDYILGGLFPLGTTEEATLNQRTQPNGI SEQ ID NO: 4

LCTRFSPLGLFLAMAMKMAVEEINNGSALLPGLRLGYDLFDTCSEPVVTMKPSLMFMAKV

GSQSIAAYCNYTQYQPRVLAVIGPHSSELALITGKFFSFFLMPQVSYSASMDRLSDRETF

PSFFRTVPSDRVQLQAVVTLLQNFSWNWVAALGSDDDYGREGLSIFSGLANSRGICIAHE

GLVPQHDTSGQQLGKVVDVLRQVNQSKVQVVVLFASARAVYSLFSYSILHDLSPKVWVAS

ESWLTSDLVMTLPNIARVGTVLGFLQRGALLPEFSHYVETRLALAADPTFCASLKAELDL

EERVMGPRCSQCDYIMLQNLSSGLMQNLSAGQLHHQIFATYAAVYSVAQALHNTLQCNVS

HCHTSEPVQPWQLLENMYNMSFRARDLTLQFDAKGSVDMEYDLKMWVWQSPTPVLHTVGT

FNGTLQLQHSKMYWPGNQVPVSQCSRQCKDGQVRRVKGFHSCCYDCVDCKAGSYRKHPDD

FTCTPCGKDQWSPEKSTTCLPRRPKFLAWGEPAVLSLLLLLCLVLGLTLAALGLFVHYWD

SPLVQASGGSLFCFGLICLGLFCLSVLLFPGRPRSASCLAQQPMAHLPLTGCLSTLFLQA

AEIFVESELPLSWANWLCSYLRGPWAWLVVLLATLVEAALCAWYLMAFPPEVVTDWQVLP

TEVLEHCRMRSWVSLGLVHITNAVLAFLCFLGTFLVQSQPGRYNRARGLTFAMLAYFIIW

VSFVPLLANVQVAYQPAVQMGAILFCALGILATFHLPKCYVLLWLPELNTQEFFLGRSPK

EASDGNSGSSEATRGHSE

Amino Acid Sequence hT1R1
MLLCTARLVGLQLLISCCWAFACHSTESSPDFTLPGDYLLAGLFPLHSGCLQVRHRPEVT SEQ ID NO: 5

LCDRSCSFNEHGYHLFQAMRLGVEEINNSTALLPNITLGYQLYDVCSDSANVYATLRVLS

LPGQHHIELQGDLLHYSPTVLAVIGPDSTNRAATTAALLSPFLVPMISYAASSETLSVKR

QYPSFLRTIPNDKYQVETMVLLLQKFGWTWISLVGSSDDYGQLGVQALENQATGQGICIA

FKDIMPFSAQVGDERMQCLMRHLAQAGATVVVVFSSRQLARVFFESVVLTNLTGKVWVAS

EAWALSRHITGVPGIQRIGMVLGVAIQKRAVPGLKAFEEAYARADKKAPRPCHKGSWCSS

NQLCRECQAFMAHTMPKLKAFSMSSAYNAYRAVYAVAHGLHQLLGCASGACSRGRVYPWQ

LLEQIHKVHFLLHKDTVAFNDNRDPLSSYNIIAWDWNGPKWTFTVLGSSTWSPVQLNINE

TKIQWHGKDNQVPKSVCSSDCLEGHQRVVTGFHHCCFECVPCGAGTFLNKSDLYRCQPCG

KEEWAPEGSQTCFPRTVVFLALREHTSWVLLAANTLLLLLLLGTAGLFAWHLDTPVVRSA

GGRLCFLMLGSLAAGSGSLYGFFGEPTRPACLLRQALFALGFTIFLSCLTVRSFQLIIIF

KFSTKVPTFYHAWVQNHGAGLFVMISSAAQLLICLTWLVVWTPLPAREYQRFPHLVMLEC

TETNSLGFILAFLYNGLLSISAFACSYLGKDLPENYNEAKCVTFSLLFNFVSWIAFFTTA

SVYDGKYLPAANMMAGLSSLSSGFGGYFLPKCYVILCRPDLNSTEHFQASIQDYTRRCGST

Amino Acid Sequence hT1R2
MGPRAKTICSLFFLLWVLAEPAENSDFYLPGDYLLGGLFSLHANMKGIVHLNFLQVPMCK SEQ ID NO: 6

EYEVKVIGYNLMQAMRFAVEEINNDSSLLPGVLLGYEIVDVCYISNNVQPVLYFLAHEDN

LLPIQEDYSNYISRVVAVIGPDNSESVMTVANFLSLFLLPQITYSAISDELRDKVRFPAL

LRTTPSADHHVEAMVQLMLHFRWNWIIVLVSSDTYGRDNGQLLGERVARRDICIAFQETL

PTLQPNQNMTSEERQRLVTIVDKLQQSTARVVVVFSPDLTLYHFFNEVLRQNFTGAVWIA

SESWAIDPVLHNLTELGHLGTFLGITIQSVPIPGFSEFREWGPQAGPPPLSRTSQSYTCN

QECDNCLNATLSFNTILRLSGERVVYSVYSAVYAVAHALHSLLGCDKSTCTKRVVYPWQL

LEEIWKVNFTLLDHQIFFDPQGDVALHLEIVQWQWDRSQNPFQSVASYYPLQRQLKNIQD

ISWHTVNNTIPMSMCSKRCQSGQKKKPVGIHVCCFECIDCLPGTFLNHTEDEYECQACPN

NEWSYQSETSCFKRQLVFLEWHEAPTIAVALLAALGFLSTLAILVIFWRHFQTPIVRSAG

-continued

GPMCFLMLTLLLVAYMVVPVYVGPPKVSTCLCRQALFPLCFTICISCIAVRSFQIVCAFK

MASRFPRAYSYWVRYQGPYVSMAFITVLKMVIVVIGMLATGLSPTTRTDPDDPKITIVSC

NPNYRNSLLFNTSLDLLLSVVGFSFAYMGKELPTNYNEAKFITLSMTFYFTSSVSLCTFM

SAYSGVLVTIVDLLVTVLNLLAISLGYFGPKCYMILFYPERNTPAYFNSMIQGYTMRRD

Amino Acid Sequence hT1R3

MLGPAVLGLSLWALLHPGTGAPLCLSQQLRMKGDYVLGGLFPLGEAEEAGLRSRTRPSSP SEQ ID NO: 7

VCTRFSSNGLLWALAMKMAVEEINNKSDLLPGLRLGYDLFDTCSEPVVAMKPSLMFLAKA

GSRDIAAYCNYTQYQPRVLAVIGPHSSELAMVTGKFFSFFLMPQVSYGASMELLSARETF

PSFFRTVPSDRVQLTAAAELLQEFGWNWVAALGSDDEYGRQGLSIFSALAAARGICIAHE

GLVPLPRADDSRLGKVQDVLHQVNQSSVQVVLLFASVHAAHALFNYSISSRLSPKVWVAS

EAWLTSDLVMGLPGMAQMGTVLGFLQRGAQLHEFPQYVKTHLALATDPAFCSALGEREQG

LEEDVVGQRCPQCDCITLQNVSAGLNHHQTFSVYAAVYSVAQALHNTLQCNASGCPAQDP

VKPWQLLENMYNLTFHVGGLPLRFDSSGNVDMEYDLKLWVWQGSVPRLHDVGRFNGSLRT

ERLKIRWHTSDNQKPVSRCSRQCQEGQVRRVKGFHSCCYDCVDCEAGSYRQNPDDIACTF

CGQDEWSPERSTRCFRRRSRFLAWGEPAVLLLLLLLSLALGLVLAALGLFVHHRDSPLVQ

ASGGPLACFGLVCLGLVCLSVLLFPGQPSPARCLAQQPLSHLPLTGCLSTLFLQAAEIFV

ESELPLSWADRLSGCLRGPWAWLVVLLAMLVEVALCTWYLVAFPPEVVTDWHMLPTEALV

HCRTRSWVSFGLAHATNATLAFLCFLGTFLVRSQPGRYNRARGLTFAMLAYFITWVSFVP

LLANVQVVLRPAVQMGALLLCVLGILAAFHLPRCYLLMRQPGLNTPEFFLGGGPGDAQGQ

NDGNTGNQGKHE

Nucleic Acid Sequence hT1R1

ATGCTGCTCTGCACGGCTCGCCTGGTCGGCCTGCAGCTTCTCATTTCCTGCTGCTGGGCC SEQ ID NO: 8

TTTGCCTGCCATAGCACGGAGTCTTCTCCTGACTTCACCCTCCCCGGAGATTACCTCCTG

GCAGGCCTGTTCCCTCTCCATTCTGGCTGTCTGCAGGTGAGGCACAGACCCGAGGTGACC

CTGTGTGACAGGTCTTGTAGCTTCAATGAGCATGGCTACCACCTCTTCCAGGCTATGCGG

CTTGGGGTTGAGGAGATAAACAACTCCACGGCCCTGCTGCCCAACATCACCCTGGGGTAC

CAGCTGTATGATGTGTGTTCTGACTCTGCCAATGTGTATGCCACGCTGAGAGTGCTCTCC

CTGCCAGGGCAACACCACATAGAGCTCCAAGGAGACCTTCTCCACTATTCCCCTACGGTG

CTGGCAGTGATTGGGCCTGACAGCACCAACCGTGCTGCCACCACAGCCGCCCTGCTGAGC

CCTTTCCTGGTGCCCATGATTAGCTATGCGGCCAGCAGCGAGACGCTCAGCGTGAAGCGG

CAGTATCCCTCTTTCCTGCGCACCATCCCCAATGACAAGTACCAGGTGGAGACCATGGTG

CTGCTGCTGCAGAAGTTCGGGTGGACCTGGATCTCTCTGGTTGGCAGCAGTGACGACTAT

GGGCAGCTAGGGGTGCAGGCACTGGAGAACCAGGCCACTGGTCAGGGGATCTGCATTGCT

TTCAAGGACATCATGCCCTTCTCTGCCCAGGTGGGCGATGAGAGGATGCAGTGCCTCATG

CGCCACCTGGCCCAGGCCGGGGCCACCGTCGTGGTTGTTTTTTCCAGCCGGCAGTTGGCC

AGGGTGTTTTTCGAGTCCGTGGTGCTGACCAACCTGACTGGCAAGGTGTGGGTCGCCTCA

GAAGCCTGGGCCCTCTCCAGGCACATCACTGGGGTGCCCGGGATCCAGCGCATTGGGATG

GTGCTGGGCGTGGCCATCCAGAAGAGGGCTGTCCCTGGCCTGAAGGCGTTTGAAGAAGCC

TATGCCCGGGCAGACAAGAAGGCCCCTAGGCCTTGCCACAAGGGCTCCTGGTGCAGCAGC

AATCAGCTCTGCAGAGAATGCCAAGCTTTCATGGCACACACGATGCCCAAGCTCAAAGCC

TTCTCCATGAGTTCTGCCTACAACGCATACCGGGCTGTGTATGCGGTGGCCCATGGCCTC

-continued

CACCAGCTCCTGGGCTGTGCCTCTGGAGCTTGTTCCAGGGGCCGAGTCTACCCCTGGCAG

CTTTTGGAGCAGATCCACAAGGTGCATTTCCTTCTACACAAGGACACTGTGGCGTTTAAT

GACAACAGAGATCCCCTCAGTAGCTATAACATAATTGCCTGGGACTGGAATGGACCCAAG

TGGACCTTCACGGTCCTCGGTTCCTCCACATGGTCTCCAGTTCAGCTAAACATAAATGAG

ACCAAAATCCAGTGGCACGGAAAGGACAACCAGGTGCCTAAGTCTGTGTGTTCCAGCGAC

TGTCTTGAAGGGCACCAGCGAGTGGTTACGGGTTTCCATCACTGCTGCTTTGAGTGTGTG

CCCTGTGGGGCTGGGACCTTCCTCAACAAGAGTGACCTCTACAGATGCCAGCCTTGTGGG

AAAGAAGAGTGGGCACCTGAGGGAAGCCAGACCTGCTTCCCGCGCACTGTGGTGTTTTTG

GCTTTGCGTGAGCACACCTCTTGGGTGCTGCTGGCAGCTAACACGCTGCTGCTGCTGCTG

CTGCTTGGGACTGCTGGCCTGTTTGCCTGGCACCTAGACACCCCTGTGGTGAGGTCAGCA

GGGGGCCGCCTGTGCTTTCTTATGCTGGGCTCCCTGGCAGCAGGTAGTGGCAGCCTCTAT

GGCTTCTTTGGGGAACCCACAAGGCCTGCGTGCTTGCTACGCCAGGCCCTCTTTGCCCTT

GGTTTCACCATCTTCCTGTCCTGCCTGACAGTTCGCTCATTCCAACTAATCATCATCTTC

AAGTTTTCCACCAAGGTACCTACATTCTACCACGCCTGGGTCCAAAACCACGGTGCTGGC

CTGTTTGTGATGATCAGCTCAGCGGCCCAGCTGCTTATCTGTCTAACTTGGCTGGTGGTG

TGGACCCCACTGCCTGCTAGGGAATACCAGCGCTTCCCCCATCTGGTGATGCTTGAGTGC

ACAGAGACCAACTCCCTGGGCTTCATACTGGCCTTCCTCTACAATGGCCTCCTCTCCATC

AGTGCCTTTGCCTGCAGCTACCTGGGTAAGGACTTGCCAGAGAACTACAACGAGGCCAAA

TGTGTCACCTTCAGCCTGCTCTTCAACTTCGTGTCCTGGATCGCCTTCTTCACCACGGCC

AGCGTCTACGACGGCAAGTACCTGCCTGCGGCCAACATGATGGCTGGGCTGAGCAGCCTG

AGCAGCGGCTTCGGTGGGTATTTTCTGCCTAAGTGCTACGTGATCCTCTGCCGCCCAGAC

CTCAACAGCACAGAGCACTTCCAGGCCTCCATTCAGGACTACACGAGGCGCTGCGGCTCC

ACCTGA

Nucleic Acid Sequence hT1R3

ATGCTGGGCCCTGCTGTCCTGGGCCTCAGCCTCTGGGCTCTCCTGCACCCTGGGACGGGG SEQ ID NO 9

GCCCCATTGTGCCTGTCACAGCAACTTAGGATGAAGGGGGACTACGTGCTGGGGGGGCTG

TTCCCCCTGGGCGAGGCCGAGGAGGCTGGCCTCCGCAGCCGGACACGGCCCAGCAGCCCT

GTGTGCACCAGGTTCTCCTCAAACGGCCTGCTCTGGGCACTGGCCATGAAAATGGCCGTG

GAGGAGATCAACAACAAGTCGGATCTGCTGCCCGGGCTGCGCCTGGGCTACGACCTCTTT

GATACGTGCTCGGAGCCTGTGGTGGCCATGAAGCCCAGCCTCATGTTCCTGGCCAAGGCA

GGCAGCCGCGACATCGCCGCCTACTGCAACTACACGCAGTACCAGCCCCGTGTGCTGGCT

GTCATCGGGCCCCACTCGTCAGAGCTCGCCATGGTCACCGGCAAGTTCTTCAGCTTCTTC

CTCATGCCCCAggtcagCTACGGTGCTAGCATGGAGCTGCTGAGCGCCCGGGAGACCTTC

CCCTCCTTCTTCCGCACCGTGCCCAGCGACCGTGTGCAGCTGACGGCCGCCGCGGAGCTG

CTGCAGGAGTTCGGCTGGAACTGGGTGGCCGCCCTGGGCAGCGACGACGAGTACGGCCGG

CAGGGCCTGAGCATCTTCTCGGCCCTGGCCGCGGCACGCGGCATCTGCATCGCGCACGAG

GGCCTGGTGCCGCTGCCCCGTGCCGATGACTCGCGGCTGGGGAAGGTGCAGGACGTCCTG

CACCAGGTGAACCAGAGCAGCGTGCAGGTGGTGCTGCTGTTCGCCTCCGTGCACGCCGCC

CACGCCCTCTTCAACTACAGCATCAGCAGCAGGCTCTCGCCCAAGGTGTGGGTGGCCAGC

GAGGCCTGGCTGACCTCTGACCTGGTCATGGGGCTGCCCGGCATGGCCCAGATGGGCACG

GTGCTTGGCTTCCTCCAGAGGGGTGCCCAGCTGCACGAGTTCCCCCAGTACGTGAAGACG

-continued

CACCTGGCCCTGGCCACCGACCCGGCCTTCTGCTCTGCCCTGGGCGAGAGGGAGCAGGGT

CTGGAGGAGGACGTGGTGGGCCAGCGCTGCCCGCAGTGTGACTGCATCACGCTGCAGAAC

GTGAGCGCAGGGCTAAATCACCACCAGACGTTCTCTGTCTACGCAGCTGTGTATAGCGTG

GCCCAGGCCCTGCACAACACTCTTCAGTGCAACGCCTCAGGCTGCCCCGCGCAGGACCCC

GTGAAGCCCTGGCAGCTCCTGGAGAACATGTACAACCTGACCTTCCACGTGGGCGGGCTG

CCGCTGCGGTTCGACAGCAGCGGAAACGTGGACATGGAGTACGACCTGAAGCTGTGGGTG

TGGCAGGGCTCAGTGCCCAGGCTCCACGACGTGGGCAGGTTCAACGGCAGCCTCAGGACA

GAGCGCCTGAAGATCCGCTGGCACACGTCTGACAACCAGAAGCCCGTGTCCCGGTGCTCG

CGGCAGTGCCAGGAGGGCCAGGTGCGCCGGGTCAAGGGGTTCCACTCCTGCTGCTACGAC

TGTGTGGACTGCGAGGCGGGCAGCTACCGGCAAAACCCAGACGACATCGCCTGCACCTTT

TGTGGCCAGGATGAGTGGTCCCCGGAGCGAAGCACACGCTGCTTCCGCCGCAGGTCTCGG

TTCCTGGCATGGGGCGAGCCGGCTGTGCTGCTGCTGCTCCTGCTGCTGAGCCTGGCGCTG

GGCCTTGTGCTGGCTGCTTTGGGGCTGTTCGTTCACCATCGGGACAGCCCACTGGTTCAG

GCCTCGGGGGGGCCCCTGGCCTGCTTTGGCCTGGTGTGCCTGGGCCTGGTCTGCCTCAGC

GTCCTCCTGTTCCCTGGCCAGCCCAGCCCTGCCCGATGCCTGGCCCAGCAGCCCTTGTCC

CACCTCCCGCTCACGGGCTGCCTGAGCACACTCTTCCTGCAGGCGGCCGAGATCTTCGTG

GAGTCAGAACTGCCTCTGAGCTGGGCAGACCGGCTGAGTGGCTGCCTGCGGGGGCCCTGG

GCCTGGCTGGTGGTGCTGCTGGCCATGCTGGTGGAGGTCGCACTGTGCACCTGGTACCTG

GTGGCCTTCCCGCCGGAGGTGGTGACGGACTGGCACATGCTGCCCACGGAGGCGCTGGTG

CACTGCCGCACACGCTCCTGGGTCAGCTTCGGCCTAGCGCACGCCACCAATGCCACGCTG

GCCTTTCTCTGCTTCCTGGGCACTTTCCTGGTGCGGAGCCAGCCGGGCTGCTACAACCGT

GCCCGTGGCCTCACCTTTGCCATGCTGGCCTACTTCATCACCTGGGTCTCCTTTGTGCCC

CTCCTGGCCAATGTGCAGGTGGTCCTCAGGCCCGCCGTGCAGATGGGCGCCCTCCTGCTC

TGTGTCCTGGGCATCCTGGCTGCCTTCCACCTGCCCAGGTGTTACCTGCTCATGCGGCAG

CCAGGGCTCAACACCCCCGAGTTCTTCCTGGGAGGGGGCCCTGGGGATGCCCAAGGCCAG

AATGACGGGAACACAGGAAATCAGGGGAAACATGAGTGA

Nucleic Acid Sequence hT1R2

ATGGGGCCCAGGGCAAAGACCATCTGCTCCCTGTTCTTCCTCCTATGGGTCCTGGCTGAG SEQ ID NO: 10

CCGGCTGAGAACTCGGACTTCTACCTGCCTGGGGATTACCTCCTGGGTGGCCTCTTCTCC

CTCCATGCCAACATGAAGGGCATTGTTCACCTTAACTTCCTGCAGGTGCCCATGTGCAAG

GAGTATGAAGTGAAGGTGATAGGCTACAACCTCATGCAGGCCATGCGCTTCGCGGTGGAG

GAGATCAACAATGACAGCAGCCTGCTGCCTGGTGTGCTGCTGGGCTATGAGATCGTGGAT

GTGTGCTACATCTCCAACAATGTCCAGCCGGTGCTCTACTTCCTGGCACACGAGGACAAC

CTCCTTCCCATCCAAGAGGACTACAGTAACTACATTTCCCGTGTGGTGGCTGTCATTGGC

CCTGACAACTCCGAGTCTGTCATGACTGTGGCCAACTTCCTCTCCCTATTTCTCCTTCCA

CAGATCACCTACAGCGCCATCAGCGATGAGCTGCGAGACAAGGTGCGCTTCCCGGCTTTG

CTGCGTACCACACCCAGCGCCGACCACCACGTCGAGGCCATGGTGCAGCTGATGCTGCAC

TTCCGCTGGAACTGGATCATTGTGCTGGTGAGCAGCGACACCTATGGCCGCGACAATGGC

AGCTGCTTGGCGAGCGCGTGGCCCGGCGCGACATCTGCATCGCCTTCCAGGAGACGCTGC

CCACACTGCAGCCCAACCAGAACATGACGTCAGAGGAGCGCCAGCGCCTGGTGACCATTG

TGGACAAGCTGCAGCAGAGCACAGCGCGCGTCGTGGTCGTGTTCTCGCCCGACCTGACCC

-continued

```
TGTACCACTTCTTCAATGAGGTGCTGCGCCAGAACTTCACGGGCGCCGTGTGGATCGCCT

CCGAGTCCTGGGCCATCGACCCGGTCCTGCACAACCTCACGGAGCTGGGCCACTTGGGCA

CCTTCCTGGGCATCACCATCCAGAGCGTGCCCATCCCGGGCTTCAGTGAGTTCCGCGAGT

GGGGCCCACAGGCTGGGCCGCCACCCCTCAGCAGGACCAGCCAGAGCTATACCTGCAACC

AGGAGTGCGACAACTGCCTGAACGCCACCTTGTCCTTCAACACCATTCTCAGGCTCTCTG

GGGAGCGTGTCGTCTACAGCGTGTACTCTGCGGTCTATGCTGTGGCCCATGCCCTGCACA

GCCTCCTCGGCTGTGACAAAAGCACCTGCACCAAGAGGGTGGTCTACCCCTGGCAGCTGC

TTGAGGAGATCTGGAAGGTCAACTTCACTCTCCTGGACCACCAAATCTTCTTCGACCCGC

AAGGGGACGTGGCTCTGCACTTGGAGATTGTCCAGTGGCAATGGGACCGGAGCCAGAATC

CCTTCCAGAGCGTCGCCTCCTACTACCCCCTGCAGCGACAGCTGAAGAACATCCAAGACA

TCTCCTGGCACACCGTCAACAACACGATCCCTATGTCCATGTGTTCCAAGAGGTGCCAGT

CAGGGCAAAAGAAGAAGCCTGTGGGCATCCACGTCTGCTGCTTCGAGTGCATCGACTGCC

TTCCCGGCACCTTCCTCAACCACACTGAAGATGAATATGAATGCCAGGCCTGCCCGAATA

ACGAGTGGTCCTACCAGAGTGAGACCTCCTGCTTCAAGCGGCAGCTGGTCTTCCTGGAAT

GGCATGAGGCACCCACCATCGCTGTGGCCCTGCTGGCCGCCCTGGGCTTCCTCAGCACCC

TGGCCATCCTGGTGATATTCTGGAGGCACTTCCAGACACCCATAGTTCGCTCGGCTGGGG

GCCCCATGTGCTTCCTGATGCTGACACTGCTGCTGGTGGCATACATGGTGGTCCCGGTGT

ACGTGGGGCCGCCCAAGGTCTCCACCTGCCTCTGCCGCCAGGCCCTCTTTCCCCTCTGCT

TCACAATTTGCATCTCCTGTATCGCCGTGCGTTCTTTCCAGATCGTCTGCGCCTTCAAGA

TGGCCAGCCGCTTCCCACGCGCCTACAGCTACTGGGTCCGCTACCAGGGGCCCTACGTCT

CTATGGCATTTATCACGGTACTCAAAATGGTCATTGTGGTAATTCGCATGCTGGCCACGG

GCCTCAGTCCCACCACCCGTACTGACCCCGATGACCCCAAGATCACAATTGTCTCCTGTA

ACCCCAACTACCGCAACAGCCTGCTGTTCAACACCAGCCTGGACCTGCTGCTCTCAGTGG

TGGGTTTCAGCTTCGCCTACATGGGCAAAGAGCTGCCCACCAACTACAACGAGGCCAAGT

TCATCACCCTCAGCATGACCTTCTATTTCACCTCATCCGTCTCCCTCTGCACCTTCATGT

CTGCCTACAGCGGGGTGCTGGTCACCATCGTGGACCTCTTGGTCACTGTGCTCAACCTCC

TGGCCATCAGCCTGGGCTACTTCGGCCCCAAGTGCTACATGATCCTCTTCTACCCGGAGC

GCAACACGCCCGCCTACTTCAACAGCATGATCCAGGGCTACACCATGAGGAGGGACTAG
```

Nucleic Acid Sequence rT1R3

```
ATGCCGGGTTTGGCTATCTTGGGCCTCAGTCTGGCTGCTTTCCTGGAGCTTGGGATGGGG    SEQ ID NO 11

TCCTCTTTGTGTCTGTCACAGCAATTCAAGGCACAAGGGGACTATATATTGGGTGGACTA

TTTCCCCTGGGCACAACTGAGGAGGCCACTCTCAACCAGAGAACACAGCCCAACGGCATC

CTATGTACCAGGTTCTCGCCCCTTGGTTTGTTCCTGGCCATGGCTATGAAGATGGCTGTA

GAGGAGATCAACAATGGATCTGCCTTGCTCCCTGGGCTGCGACTGGGCTATGACCTGTTT

GACACATGCTCAGAGCCAGTGGTCACCATGAAGCCCAGCCTCATGTTCATGGCCAAGGTG

GGAAGTCAAAGCATTGCTGCCTACTGCAACTACACACAGTACCAACCCCGTGTGCTGGCT

GTCATTGGTCCCCACTCATCAGAGCTTGCCCTCATTACAGGCAAGTTCTTCAGCTTCTTC

CTCATGCCACAGGTCAGCTATAGTGCCAGCATGGATCGGCTAAGTGACCGGGAAACATTT

CCATCCTTCTTCCGCACAGTGCCCAGTGACCGGGTGCAGCTGCAGGCCGTTGTGACACTG

TTGCAGAATTTCAGCTGGAACTGGGTGGCTGCCTTAGGTAGTGATGATGACTATGGCCGG

GAAGGTCTGAGCATCTTTTCTGGTCTGGCCAACTCACGAGGTATCTGCATTGCACACGAG
```

-continued

```
GGCCTGGTGCCACAACATGACACTAGTGGCCAACAATTGGGCAAGGTGGTGGATGTGCTA

CGCCAAGTGAACCAAAGCAAAGTACAGGTGGTGGTGCTGTTTGCATCTGCCCGTGCTGTC

TACTCCCTTTTTAGCTACAGCATCCTTCATGACCTCTCACCCAAGGTATGGGTGGCCAGT

GAGTCCTGGCTGACCTCTGACCTGGTCATGACACTTCCCAATATTGCCCGTGTGGGCACT

GTTCTTGGGTTTCTGCAGCGCGGTGCCCTACTGCCTGAATTTTCCCATTATGTGGAGACT

CGCCTTGCCCTAGCTGCTGACCCAACATTCTGTGCCTCCCTGAAAGCTGAGTTGGATCTG

GAGGAGCGCGTGATGGGGCCACGCTGTTCACAATGTGACTACATCATGCTACAGAACCTG

TCATCTGGGCTGATGCAGAACCTATCAGCTGGGCAGTTGCACCACCAAATATTTGCAACC

TATGCAGCTGTGTACAGTGTGGCTCAGGCCCTTCACAACACCCTGCAGTGCAATGTCTCA

CATTGCCACACATCAGAGCCTGTTCAACCCTGGCAGCTCCTGGAGAACATGTACAATATG

AGTTTCCGTGCTCGAGACTTGACACTGCAGTTTGATGCCAAAGGGAGTGTAGACATGGAA

TATGACCTGAAGATGTGGGTGTGGCAGAGCCCTACACCTGTACTACATACTGTAGGCACC

TTCAACGGCACCCTTCAGCTGCAGCACTCGAAAATGTATTGGCCAGGCAACCAGGTGCCA

GTCTCCCAGTGCTCCCGGCAGTGCAAAGATGGCCAGGTGCGCAGAGTAAAGGGCTTTCAT

TCCTGCTGCTATGACTGTGTGGACTGCAAGGCAGGGAGCTACCGGAAGCATCCAGATGAC

TTCACCTGTACTCCATGTGGCAAGGATCAGTGGTCCCCAGAAAAAAGCACAACCTGCTTA

CCTCGCAGGCCCAAGTTTCTGGCTTGGGGGGAGCCAGCTGTGCTGTCACTTCTCCTGCTG

CTTTGCCTGGTGCTGGGCCTGACACTGGCTGCCCTGGGGCTCTTTGTCCACTACTGGGAC

AGCCCTCTTGTTCAGGCCTCAGGTGGGTCACTGTTCTGCTTTGGCCTGATCTGCCTAGGC

CTCTTCTGCCTCAGTGTCCTTCTGTTCCCAGGACGACCACGCTCTGCCAGCTGCCTTGCC

CAACAACCAATGGCTCACCTCCCTCTCACAGGCTGCCTGAGCACACTCTTCCTGCAAGCA

GCCGAGATCTTTGTGGAGTCTGAGCTGCCACTGAGTTGGGCAAACTGGCTCTGCAGCTAC

CTTCGGGGCCCCTGGGCTTGGCTGGTGGTACTGCTGGCCACTCTTGTGGAGGCTGCACTA

TGTGCCTGGTACTTGATGGCTTTCCCTCCAGAGGTGGTGACAGATTGGCAGGTGCTGCCC

ACGGAGGTACTGGAACACTGCCGCATGCGTTCCTGGGTCAGCCTGGGCTTGGTGCACATC

ACCAATGCAGTGTTAGCTTTCCTCTGCTTTCTGGGCACTTTCCTGGTACAGAGCCAGCCT

GGTCGCTATAACCGTGCCCGTGGCCTCACCTTCGCCATGCTAGCTTATTTCATCATCTGG

GTCTCTTTTGTGCCCCTCCTGGCTAATGTGCAGGTGGCCTACCAGCCAGCTGTGCAGATG

GGTGCTATCTTATTCTGTGCCCTGGGCATCCTGGCCACCTTCCACCTGCCCAAATGCTAT

GTACTTCTGTGGCTGCCAGAGCTCAACACCCAGGAGTTCTTCCTGGGAAGGAGCCCCAAG

GAAGCATCAGATGGGAATAGTGGTAGTAGTGAGGCAACTCGGGGACACAGTGAATGA
```

Also, the following conceptual translations, which correspond to the C-termini of two orthologous pairs of fish T1 Rs, are derived from unpublished genomic sequence fragments and provided. Fugu T1RA was derived from accession 'scaffold 164'; Fugu T1RB was derived from accession LPC61711; Tetradon T1RA was derived from accession AL226735; Tetradon T1 RB was derived from accession AL222381. Ambiguities in the conceptual translations ('X') result from ambiguities in database sequences.

```
T1RA Fugu
PSPFRDIVSYPDKIILGCFMNLKTSSVSFVLLLLLCLLCFIFSYMGKDLPKNYNEAKAIT  SEQ ID NO 12

FCLLLLILTWIIFTTASLLYQGKYIHSLNALAVLSSIYSFLLWYFLPKCYIIIFQPQKNT

QKYFQGLIQDYTKTISQ
```

-continued

```
T1RA Tetradon
FAVNYNTPVVRSAGGPMCFLILGCLSLCSISVFFYFERPTEAFCILRFMPFLLFYAVCLA  SEQ ID NO 13

CFAVRSFQIVIIFKIAAKFPRVHSWWMKYHGQWLVISMTFVLQAVVIVIGFSSNPPLPYX

XFVSYPDKIILGCDVNLNMASTSFFLLLLLCILCFTFSYMGKDLPKNYNEAKAITFCLLL

LILTWIIFATAFMLYHGKYIHTLNALAVLSSAYCFLLWYFLPKCYIIIFQPHKNTQKYFQ

LS

T1RB Fugu
KKQGPEVDIFIVSVTILCISVLGVAVGPPEPSQDLDFYMDSIVLECSNTLSPGSFIELCY  SEQ ID NO 14

VCVLSVLCFFFSYMGKDLPANYNEAKCVTFSLMVYMISWISFFTVYLISRGPFTVAAYVC

ATLVSVLAFFGGYFLPKIYIIVLKPQMNTTAHFQNCIQMYTMSKQ

T1RB Tetradon
APKSSQRXLRRTRLXLEWDHPMSVALLFFLVCCLLMTSSSAVILLLNINTPVAKSAGGXT  SEQ ID NO 15

CXLKLAALTAAAMSSXCHFGQPSPLASKLKQPQFTFSFTVCLACNRCALATGHLHFXIRV

ALPPAYNXWAKNHGPXATIFIASAAILCVLCLRVAVGPPQPSQBLBFXTNSIXLXXSNTL

SPGSFVELCNVSLLSAVCFVFSXMGKBLPANYNEAKCVTFSLMVNXISWISFFTVY
```

Additionally, the accession number and reference citations relating to mouse and rat T1Rs and allelic variants thereof in the public domain are is set forth below: rT1 R1 (Accession # MD18069) (Hoon et al., Cell 96 (4): 541-51 (1999)); rT1 R2 (Accession # MD18070) (Hoon et al., Cell 96(4): 541-59 (1999)); mT1R1 (Accession # MK39437); mT1R2 (Accession #AAK 39438); mT1R3 (Accession MK 55537) (Max et al., Nat. Genet. 28(1): 58-63 (2001)); rT1 R1 (Accession # AAK07092) (Li et al., Mamm. Genome (1 2(1):13-16 (2001)); mT1R1 (Accession # NP 114073); mT1R1 (Accession # MK07091) (Li et al., Mamm. Genome (121):13-16 (2001)); rT1R2 (Accession # MD18070) (Hoon et al., Cell 9664): 541-551 (1999)); mT1 R2 (Accession # NP114079); mT1 R3 (Accession # AAK39436); mT1 R3 (Accession # BAB47181); (Kitagawa et al., Biochem. Biophys. Res. Comm. 283(1):23642 (2001)); mT1R3 (Accession #NP114078); mT1R3 (Accession # AAK55536) (Max et al., Nat. Genet. 28(1):58-63 (2001)); and mT1 R3 (Accession No. AAK01937).

Example 2

Sequence Alignment of Human and Rat T1Rs

Cloned T1R sequences selected from those identified above were aligned against the corresponding rat T1Rs. As shown in FIG. 1, human T1R1, human T1R2 and human T1R3 and rat T1R3 were aligned with previously described T1Rs (rT1R1 having Accession # MD18069 and rT1R2 having Accession # MD18070), the rat mGluR1 metabotropic, glutamate receptor (Accession # P23385); and the human calcium-sensing receptor (Accession #P41180). For clarity of the comparison, the mGluR1 and calcium-sensing receptor C-termini are truncated. The seven potential transmembrane segments are boxed in blue. Residues that contact the glutamate side-chain carbutylate in the mGluR1 crystal structure are boxed in red, and residues that contact the glutamate α-amino acid moiety are boxed in green. The mGluR1 and calcium-sensing receptor cysteine residues implicated in intersubunit disulfide-based formation are circled in purple. These cysteines are not conserved in T1R1 and T1R2, but are located in a degraded region of the alignment that contains a potentially analogous T1R3 cysteine residue, also circled.

Example 3

Demonstration by RT-PCR that hT1 R2 and hT1 R3 are Expressed in Taste Tissue As shown in FIG. 2, hT1R2 and hT1R3 are expressed in taste tissue: expression of both genes can be detected by RT-PCR from resected human circumvallate papillae.

Example 4

Methods for Heterologous Expression of T1Rs in Heterologous Cells

An HEK-293 derivative (Chandrashekar et al., Cell 100 (6): 703-11 (2000)), which stably expresses Gal 5, was grown and maintained at 37° C. in Dulbecco's Modified Eagle Medium (DMEM, Gibco BRL) supplemented with 10% FBS, MEM non-essential amino acids (Gibco BRL), and 3 μg/ml blasticidin. For calcium-imaging experiments, cells were first seeded onto 24-well tissue-culture plates (approximately 0.1 million cells per well), and transfected by lipofection with Mirus Translt-293 (PanVera). To minimize glutamate-induced and glucose-induced desensitization, supplemented DMEM was replaced with low-glucose DMEM/GlutaMAX (Gibco BRL) approximately 24 hours after transfection. 24 hours later, cells were loaded with the calcium dye Fluo-4 (Molecular Probes), 3 μM in Dulbecco's PBS buffer (DPBS, GibcoBRL), for 1.5 hours at room temperature. After replacement with 250 μl DPBS, stimulation was performed at room temperature by addition of 2001 DPBS supplemented with taste stimuli. Calcium mobilization was monitored on a Axiovert S100 TV microscope (Zeiss) using Imaging Workbench 4.0 software (Axon). T1R1/T1R3 and TI R2/T1R3 responses were strikingly transient—calcium increases rarely persisted longer than 15 seconds—and asynchronous. The number of responding cells was thus relatively constant over time; therefore, cell responses were quantitated by manually counting the number of responding cells at a fixed time point, typically 30 seconds after stimulus addition.

Example 5

Human T1R2/T1R3 Functions as a Sweet Taste Receptor

Figure 3A:
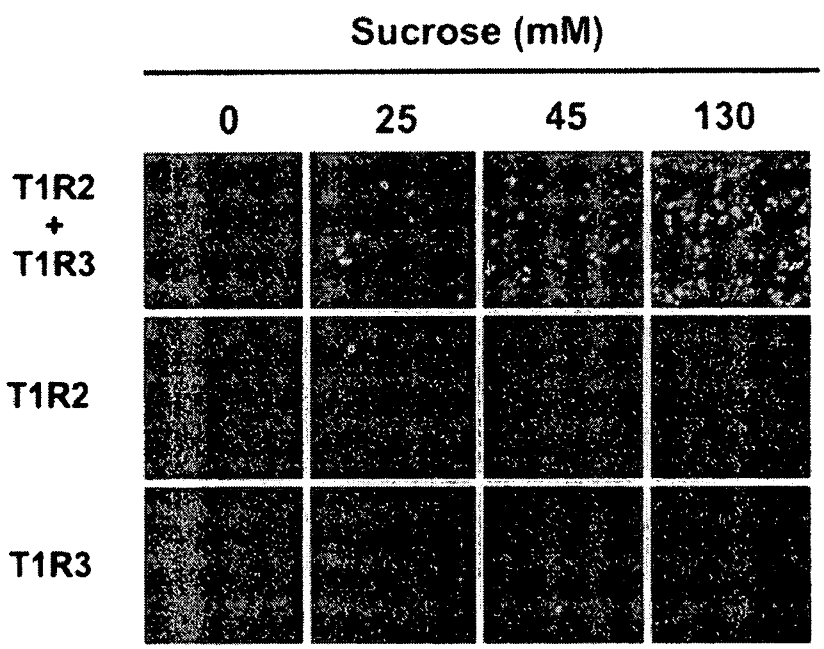
FIGS. 3*a*-3*c* contain functional data (intracellular calcium responses) elicited by different sweet taste stimuli in HEK cells stably expressing $G_{\alpha 15}$ that are transiently transfected with human T1R2, T1R3 and T1R2/T1R3 at various concentrations of sweet taste stimuli (FIG. 3*a*); human T1R2/T1R3 dose responses for several sweet taste stimuli (FIG. 3*b*); human T1R2/T1R3 responses to sucrose in the presence of gurmarin, and endogenous β2-adrenergic receptor responses to isoproterenol in the presence of gurmarin.
Figure 3B:
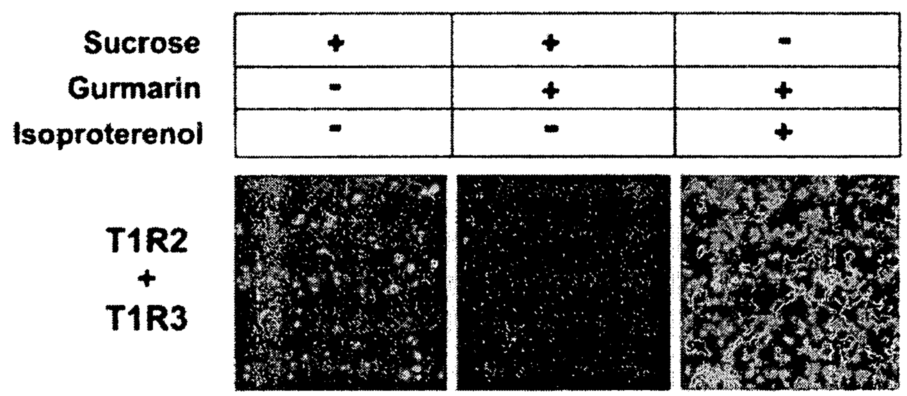
Figure 3C:
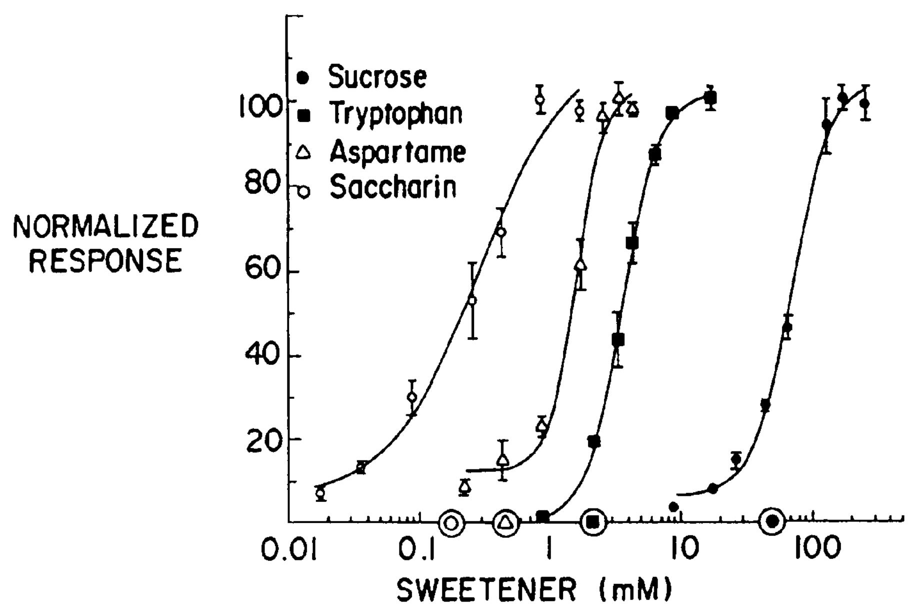

HEK cells stably expressing Gα15 were transiently transfected with human T1R2, T1R3 and T1R2/T1R3, and assayed for increases in intracellular calcium in response to increasing concentrations of sucrose (FIG. 3(*a*)). Also, T1R2/T1R3 dose responses were determined for several sweet taste stimuli (FIG. 3(*b*)). The maximal percentage of responding cells was different for different sweeteners, ranging from 10-30%. For clarity, dose responses were normalized to the maximal percentage of responding cells. The values in FIG. 3 represent the mean±s.e. of four independent responses. X-axis circles mark psychophysical detection thresholds determined by taste testing. Gurmarin (50-fold dilution of a filtered 10 g/l *Gymnema sylvestre* aqueous extract) inhibited the response of T1R2/T1R3 to 250 mM sucrose, but not the response of endogenous β2-adrenergic receptor to 20 μM isoproterenol (FIG. 3(*b*)). FIG. 3(*c*) contains the normalized response of T1R2/T1R3 co-expressing cell lines to different sweeteners (sucrose, aspartame, D-tryptophan and saccharin).

Example 6

Rat T1R2/T1R3 also Functions as a Sweet Taste receptor

Figure 4:
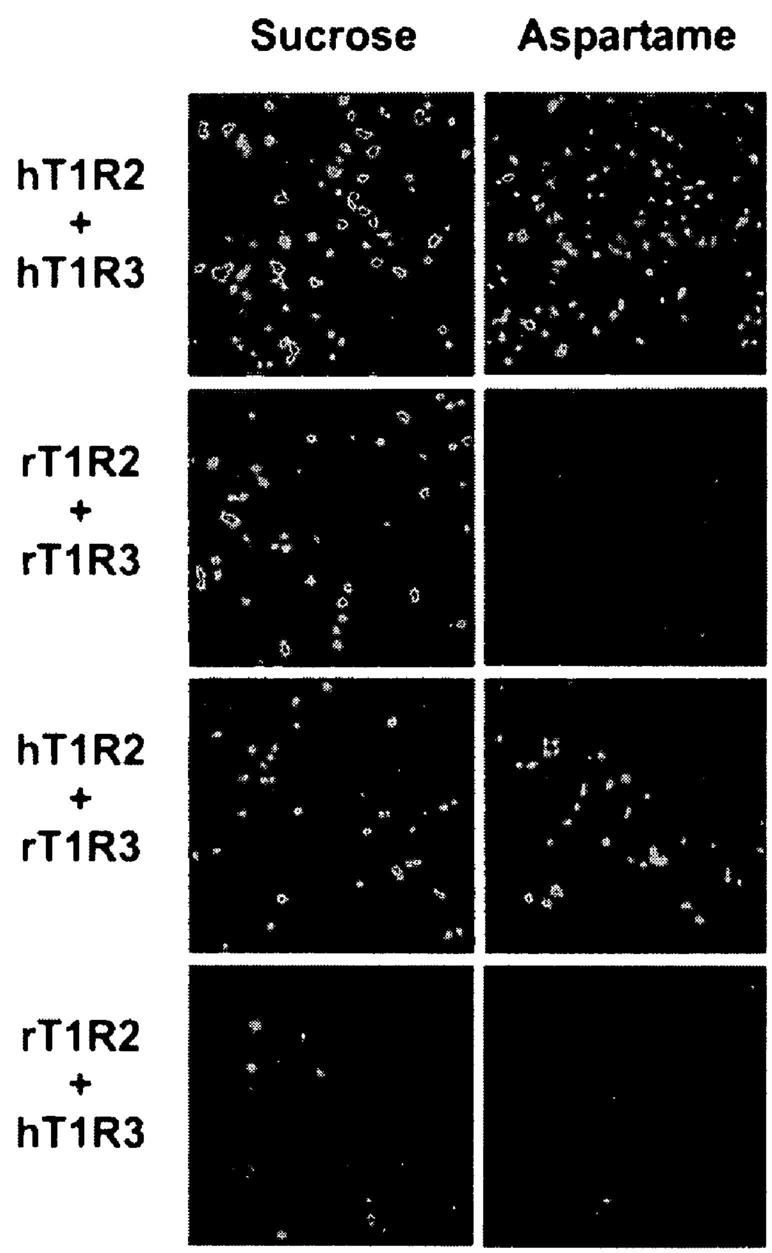
FIG. 4 contains intracellular calcium responses in HEK cells stably expressing Gα15, transiently transfected with hT1R2/hT1R3, rT1R2/rT1R3, hT1R2/rT1R3 and rT1R2/hT1R3 in response to 350 mM sucrose, 25 mM tryptophan, 15 mM aspartame, and 0.05% monellin.

HEK cells stably expressing Gα15 were transiently transfected with hT1R2/hT1R3, rT1R2/rT1R3, hT1R2/rT1R3, and rT1R2/hT1R3. These These transfected cells were then assayed for increased intracellular calcium in response to 350 mM sucrose, 25 mM tryptophan, 15 mM aspartame, and 0.05% of monellin. The results with sucrose and aspartame are contained in FIG. 4 and indicate that rT1R2/rT1R3 also functions as a sweet taste receptor. Also, these results suggest that T1R2 may control T1R2/T1R3 ligand specificity.

Example 7

T1R2/T1R3 Responses Using an Automated Fluorescence Based Assay

Figure 6:
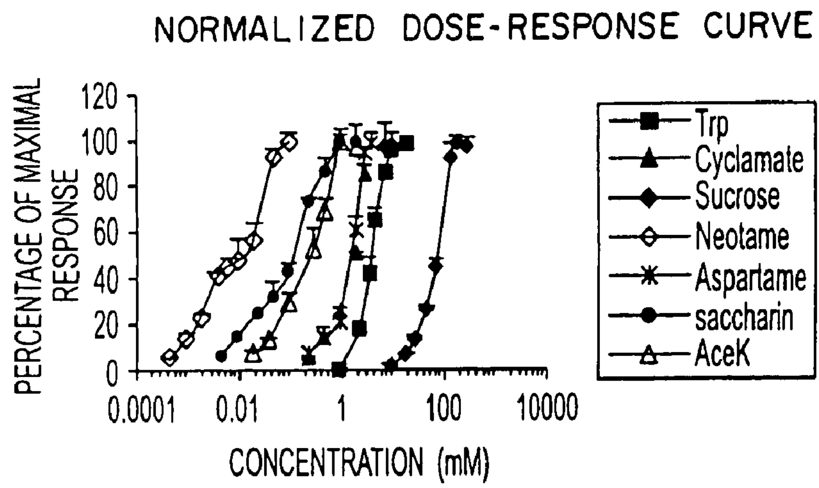
FIG. 6 contains normalized dose-response curves which show that hT1R2 and hT1R3 function in combination as the human sweet receptor based on their dose-specific interaction with various sweet stimuli (trp, cyclamate, sucrose, neotame, asparame, saccharin and Acek).
Figure 5:
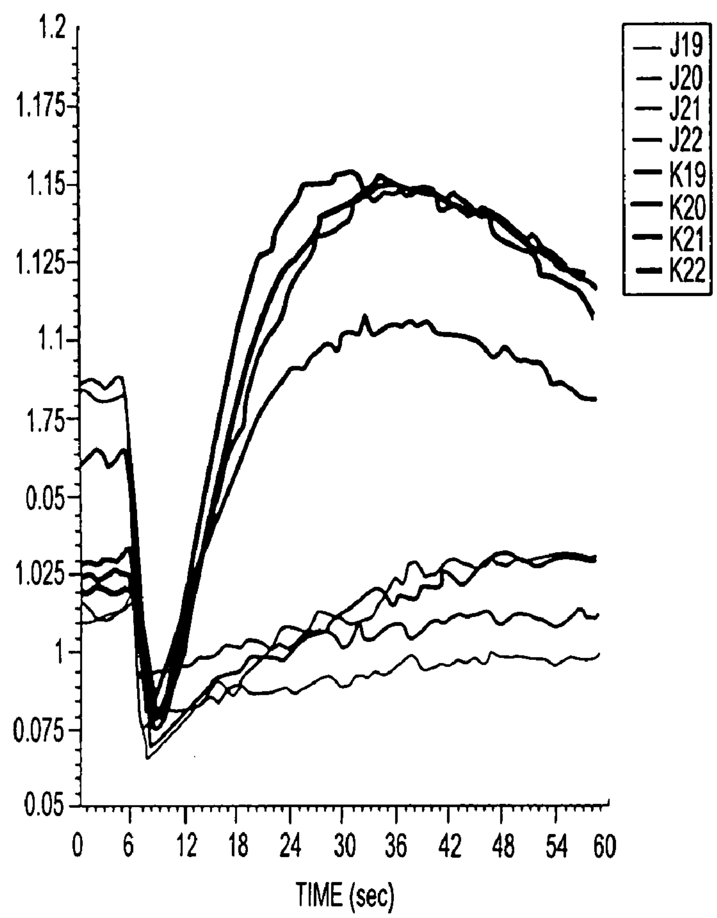
FIG. 5 contains the results of a fluorescence plate reactor based assay wherein HEK cells stably expressing Gα15 were transiently transfected with hT1R2 and hT1R3 or hT1R3 alone and contacted with the calcium dye Fluo-4 and a sweet taste stimulus (12.5 mM cyclamate).
Figure 7:
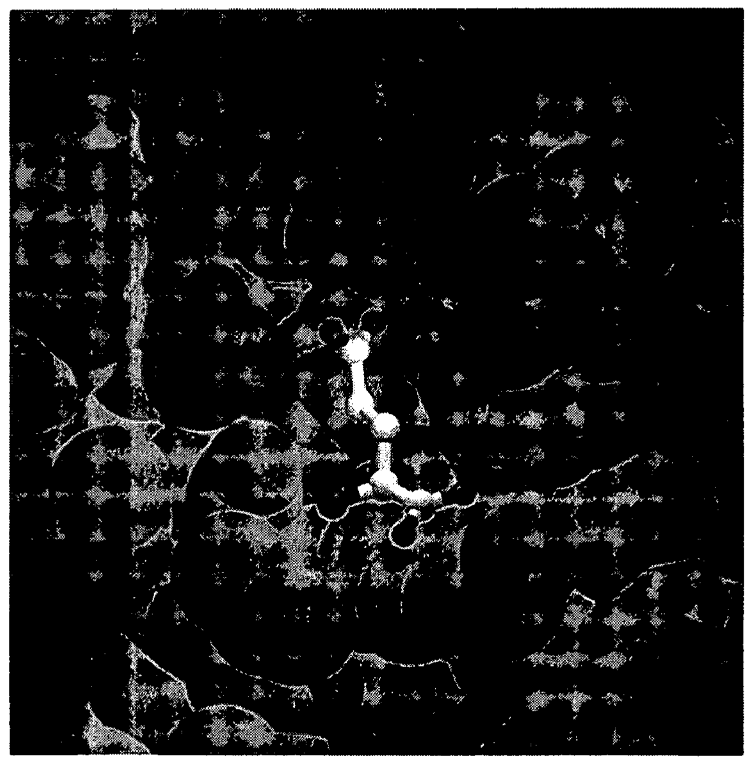
FIG. 7 contains structural information relating to mGluR1 and T1R1 showing the key ligand binding residues are observed in these molecules.

HEK cells stably expressing Gα15 were transiently transfected with hT1R2 and hT1R3. These cells were loaded with the calcium dye Fluo-4, and their responses to a sweetener measured using a fluorescence plate reader. FIG. 5 contains cyclamate (12.5 mM) responses for cells expressing hT1R2/hT1R3 and for cells expressing only hT1R3 (J19-22). The fluorescence results obtained indicate that responses to these taste stimuli only occurred in the cells expressing hT1R2/hT1R3. FIG. 6 contains normalized dose-response curves, the results of which show that hT1R2 and hT1R3 function together as a human taste receptor based on their dose-specific interaction with various sweet stimuli. Particularly, FIG. 6 contains dose-responses for sucrose, tryptophan and various other commercially available sweeteners. These results indicate that T1R2/T1R3 is a human sweet taste receptor as the rank order and threshold values obtained in the assay closely mirror values for human sweet taste.

Example 8

Ligand-binding Residues of mGluR1 are Conserved in T1R1

As shown in FIG. 6, the key ligand-binding residues of mGluR1 are conserved in T1R1. The interaction of glutamate with mGluR1 is shown with several key residues highlighted according to the same color scheme as FIG. 1.

Example 9

Human T1R1/T1R3 Functions as Umami Taste Receptors

Figure 8C:
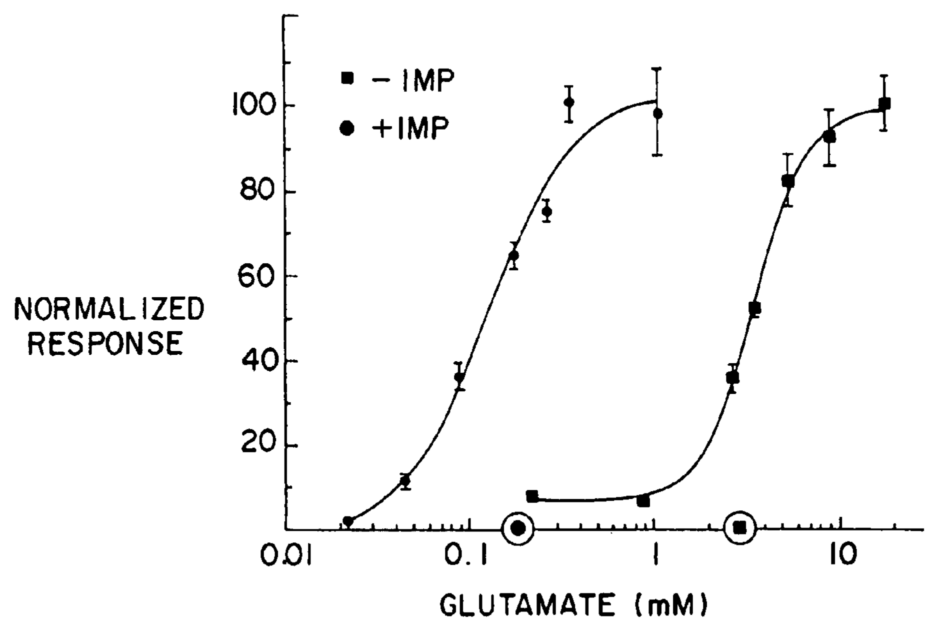
FIGS. 8*a*-8*c* contain functional data showing HEK cells which stably express Gα15 that are transiently transfected with T1 R1/T1R3 respond to glutamate in an intracellular calcium-based assay.
Figure 8A:
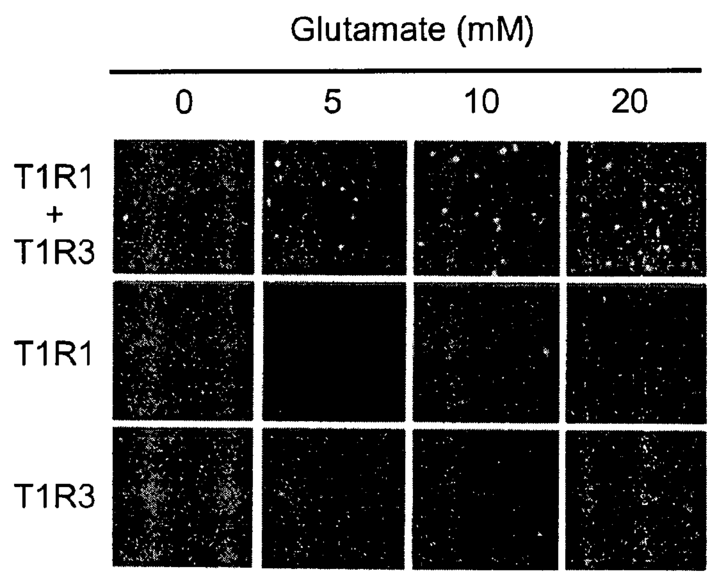
Figure 8B:
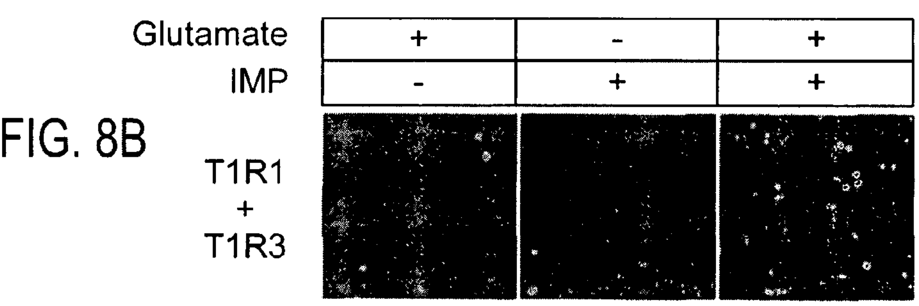

HEK cells stably expressing Gα15 were transiently transfected with human T1R1, T1R3 and T1R1/T1R3 and assayed for increases in intracellular calcium in response to increasing concentrations of glutamate (FIG. 8(*a*)), and 0.5 mM glutamate), 0.2 mM IMP, and 0.5 mM glutamate plus 0.2 mM IMP (FIG. 8(*b*)). Human T1R1/T1R3 dose responses were determined for glutamate in the presence and absence of 0.2 mM IMP (FIG. 8(*c*)). The maximal percentages of responding cells was approximately 5% for glutamate and approximately 10% for glutamate plus IMP. For clarity, does responses are normalized to the maximal percentage of responding cells. The values represent the mean±s.e. of four independent responses. X-axis circles mark taste detection thresholds determined by taste testing.

Example 10

PDZIP as an Export Sequence

Figure 9A:
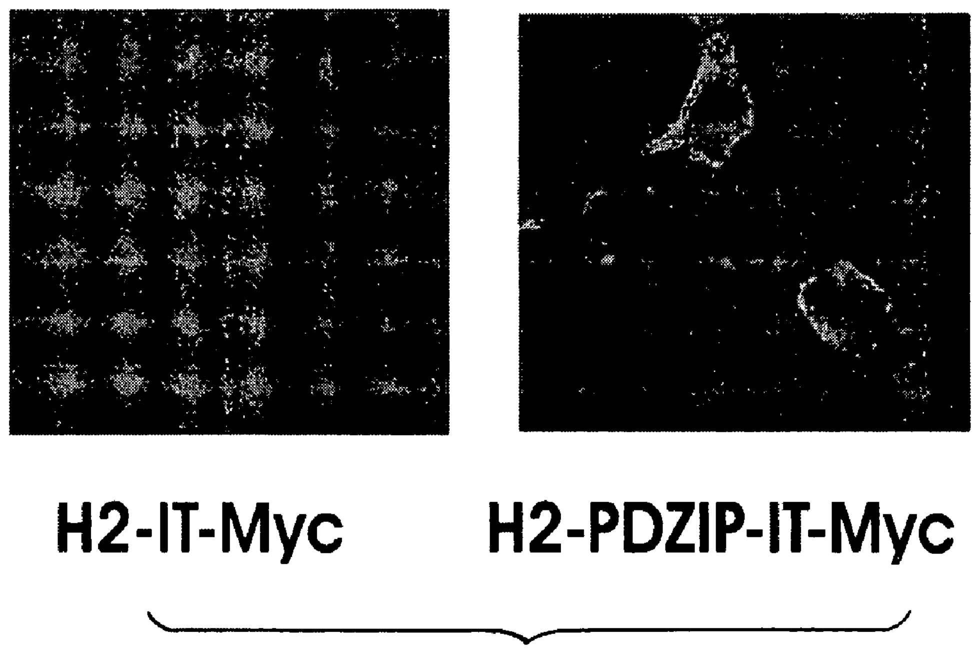
FIGS. 9*a*-9*b* respectively contain the results of an immunofluorescence staining assay using Myc-tagged hT1R2 and a FACS experiment showing that the incorporation of the PDZIP peptide (SEQ ID No: 1) enhanced the expression of a T1 R (hT1R2) on the plasma membrane.
Figure 9B:
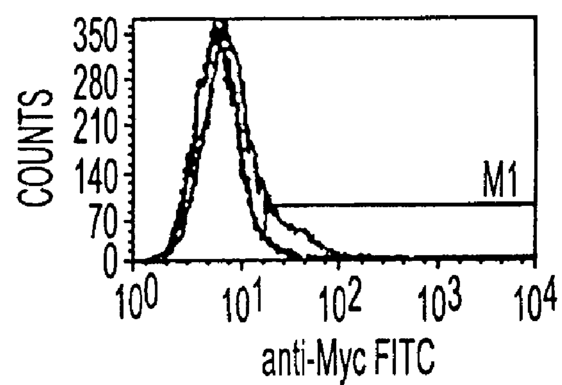
Figure 10:
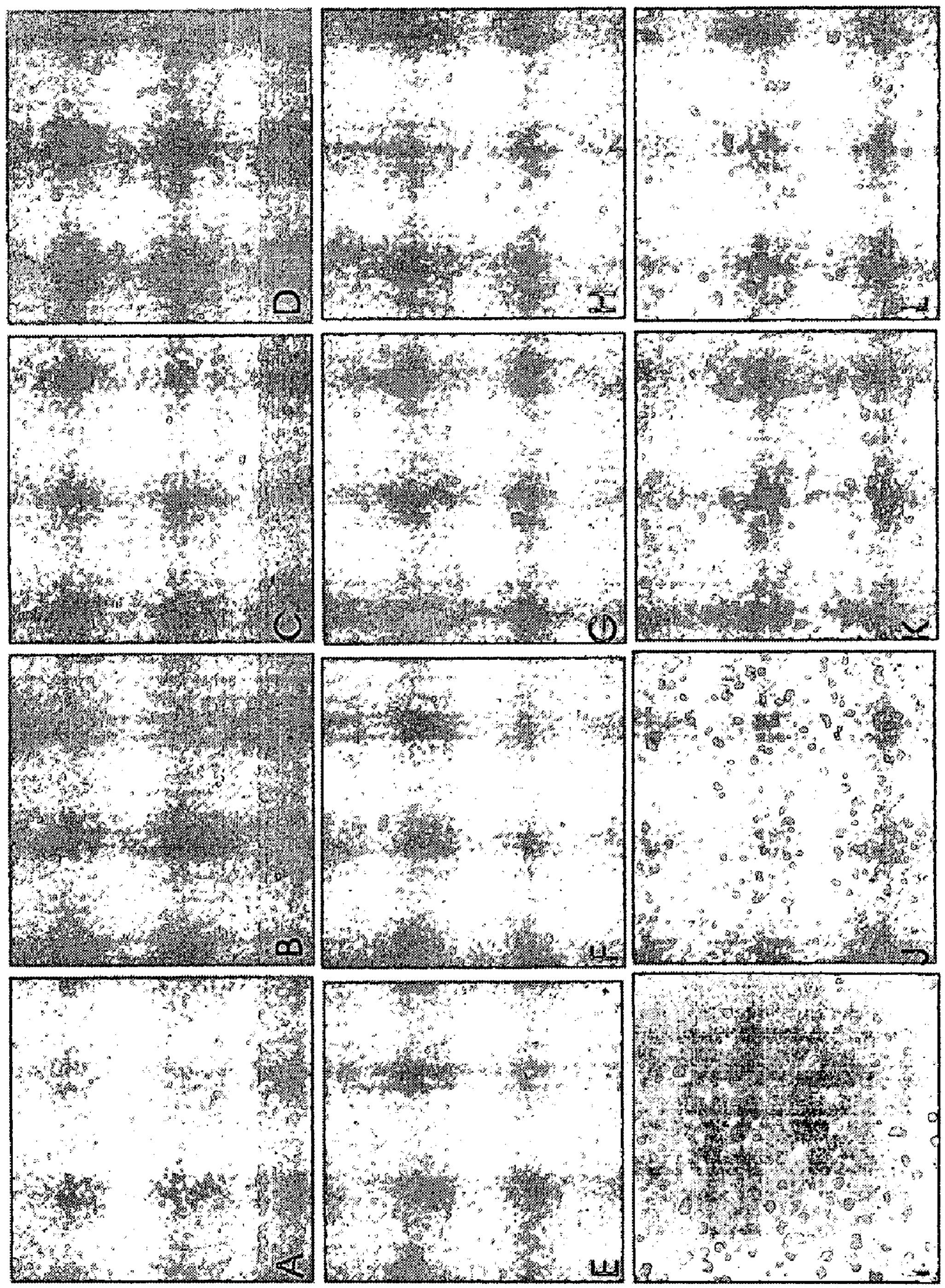
FIGS. 10A-10L contain calcium imaging data demonstrating that h1TR2/hT1R3 respond to different sweet stimuli.

The six residue PDZIP sequence (SVSTW (SEQ ID NO:1)) was fused to the C-terminus of hT1R2 and the chimeric receptor (i.e. hT1R2-PDZIP) was transfected into an HEK-293 host cell. The surface expression of hT1R2 was then monitored using immunofluorescence and FACS scanning data. As shown in FIGS. 9A and 9B, the inclusion of the PDZIP sequence increased the surface expression of hT1R2-PDZIP relative to hT1R2. More specifically, FIG. 9A shows an immunofluorescence staining of myc-tagged hT1R2 demonstrating that PDZIP significantly increases the amount of hT1R2 protein on the plasma membrane. FIG. 9B shows FACS analysis data demonstrating the same result-Cells expressing myc-tagged hT1R2 are indicated by the dotted line and cells expressing myc-tagged hT1R2-PDZIP are indicated by the solid line. Particularly, FIG. 10A shows untransfected Gα15 stable host cells in HBS buffer, FIG. 10B shows hT1R2-PDZIP transfected Gα15 stable hose cells in sweetener pool no. 5 (saccharin, sodium cyclamate, Acesulfame K, and Aspartame-20 mM each in HBS buffer), FIG. 10C shows T1R3-PDZIP transfected Gα15 stable host cells in sweetener pool no. 5, and FIG. 10D shows hT1R2-PDZIP/hT1R3-PDZIP co-transfected Gα15 stable host cells in sweetener pool no. 5. Further, FIGS. 10E-10H show dose-dependent response of hT1R2/hT1R3 co-transfected Gα15 stable host cells to sucrose-E: 0 mM in HBS buffer; F: 30 mM; G: 60 mM; and H: 250 mM. FIGS. 10I-10L shown the responses of hT1R2/hT1R3 co-transfected Gα15 stable host cells to individual sweeteners—I: Aspartame (1.5 mM); J: Acesulfame K (1 mM); K: Neotame (20 mM); L: Sodium cyclamate (20 mM). As demonstrated by the calcium-images of FIG. 10, hT1R2 and hT1R3 are both required for the activities triggered by the sweet stimuli.

Example 11

Generation of Cell Lines that Stably Co-Express TI R1/T1R3 or T1R2/T1R3

Human cell lines that stably co-express human T1R2/T1R3 or human T1R1/T1R3 were generated by transfecting linearized PEAK10-derived (Edge Biosystems) vectors and PcDNA 3.1/ZEO-derived (Invitrogen) vectors respectively containing hT1R1 or hT1R2 expression construct (plasmid SAV2485 for T1R1, SAV2486 for T1R2) and hT1R3 (plasmid SXV550 for T1R3) into a $G_{\alpha 15}$ expressing cell line. Specifically, T1R2/T1R3 stable cell lines were produced by co-transfecting linearized SAV2486 and SXV550 into Aurora Bioscience's HEK-293 cell line that stably expresses $G_{\alpha 15}$. T1 µl/T1R3 stable cell lines were produced by co-transfecting linearized SAV2485 and SXV550 into the same HEK-293 cell line that stably expresses $G_{\alpha 15}$. Following SAV2485/SXV550 and SAV2486/SXV550 transfections, puromycin-resistant and zeocin-resistant colonies were selected, expanded, and tested by calcium imaging for responses to sweet or umami taste stimuli. Cells were selected in 0.0005 mg/ml puromycin (CALBIOCHEM) and 0.1 mg/ml zeocin (Invitrogen) at 37° C. in low-glucose DMEM supplemented with GlutaMAX, 10% dialyzed FBS, and 0.003 mg/ml blasticidin. Resistant colonies were expanded, and their responses to sweet taste stimuli evaluated by Fluorescence microscopy. For automated fluorimetric imaging on VIPR-II instrumentation (Aurora Biosciences), T1R2/T1R3 stable cells were first seeded onto 96-well plates (approximately 100,000 cells per well). Twenty-four hours later, cells were loaded with the calcium dye fluo-3-AM (Molecular Probes), 0.005 mM in PBS, for one hour at room temperature. After replacement with 70 µl PBS, stimulation was performed at room temperature by addition of 70 µl PBS supplemented with taste stimuli. Fluorescence (480 nm excitation and 535 nm emission) responses from 20 to 30 seconds following compound addition were averaged, corrected for background fluorescence measured prior to compound addition, and normalized to the response to 0.001 mM ionomycin (CALBIOCHEM), a calcium ionophore.

It was then observed that when these cell lines were exposed to sweet or umami stimuli, that for active clones typically 80-100% of cells responded to taste stimuli. Unexpectedly, the magnitude of individual cell responses was markedly larger than that of transiently transfected cells.

Figure 11:
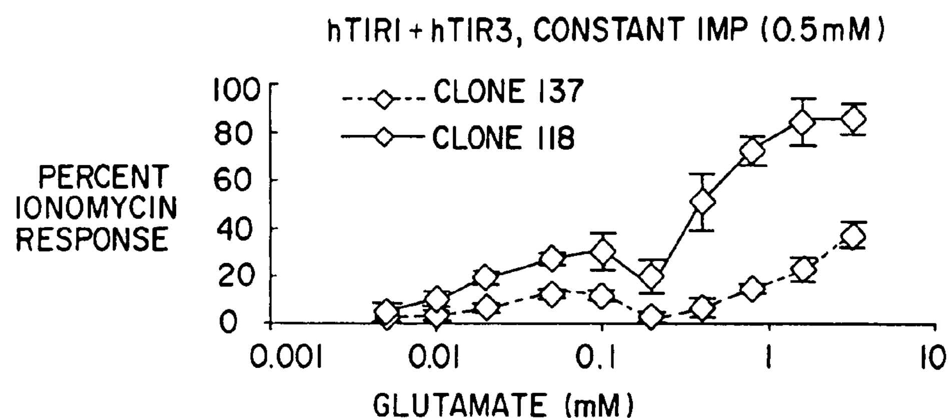
FIG. 11 shows the responses of cell lines which stably express hT1R1/hT1R3 by automated fluorescence imaging to umami taste stimuli.
Figure 12:
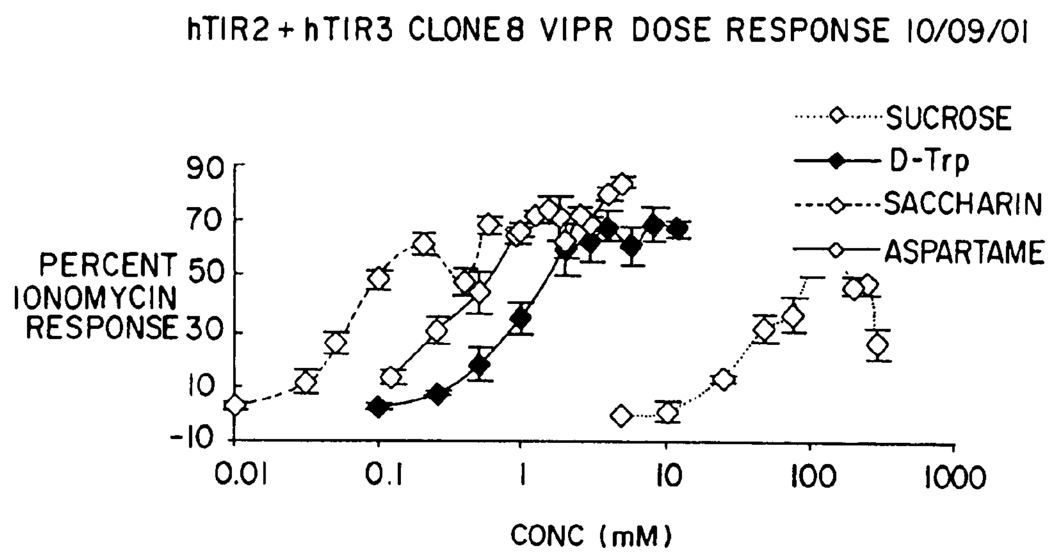
FIG. 12 shows the responses of a cell line which stably expresses hT1R2/hT1R3 by automated fluorescence imaging to sweet taste stimuli.

Based on this observation, the inventors tested the activity of T1R stable cell lines by automated fluorescence imaging using Aurora Bioscience's VIPR instrumentation as described above. The responses of two T1R1/T1R3 and one T1R2/T1R3 cell line are shown in FIG. 11 and FIG. 12 respectively.

Remarkably, the combination of increased numbers of responding cells and increased response magnitudes resulted in a greater than 10-fold increase in activity relative to transiently transfected cells. (By way of comparison, the percent ionomycin response for cells transiently transfected with T1R2/T1R3 was approximately 5% under optimal conditions.) Moreover, dose responses obtained for stably expressed human T1R2/T1R3 and T1R1/T1R3 correlated with human taste detection thresholds. The robust T1R activity of these stable cell lines suggests that they are well suited for use in high-throughput screening of chemical libraries in order to identify compounds, e.g. small molecules, that modulate the sweet or umami taste receptor and which therefore modulate, enhance, block or mimic sweet or umami taste.

Example 12

Generation of Cell Lines that Inducibly Co-express T1R1/T1R3 which Selectively Respond to Umami Taste Stimuli T1R1/T1R3 HEK 293 cell lines that stably expressed the umami taste receptor display robust improved activity relative to transiently tranfected cites. However, a disadvantage is that they can rapidly lose activity during cell propagation.

Also, these findings support the inventors' hypothesis that (i) T1R1/T1R3 is a umami taste receptor, i.e., and (ii) that cell lines which robustly express T1R1/T1R3, preferably stable and/or inducible T1R1/T1R3 cell lines can be used in assays, preferably for high throughput screening of chemical libraries to identify novel modulators of umami taste. Modulators that enhance umami taste may be used.

To overcome the instability of the T1R1/T1R3 stable cell lines, the HEK-$G_{\alpha 15}$ cells have been engineered to inducibly express T1R1/T1R3 using the GeneSwitch system (Invitrogen). pGene-derived zeocin-resistant expression vectors for human T1R1 and T1R3 (plasmid SXV603 for T1R1 and SXV611 for T1R3) and a puromycin-resistant pSwitch-derived vector that carries the GeneSwitch protein (plasmid SXV628) were linearized and cotransfected into the HEK-$G_{\alpha 15}$ cell line. Zeocin-resistant and puromycin-resistant colonies were selected, expanded, induced with variable amounts of mifepristone, and tested by calcium imaging for responses to umami taste stimuli.

Inducible expression of T1 µl/T1R3 resulted in robust activity. For example, approximately 80% of induced cells but only approximately 10% of transiently transfected cells responded to L-glutamate; More specifically, pGene derived Zeocin-resistant expression vectors that express human T1R1 and human T1R3 and a puromycn-resistant pSwitch-derived vector that carries the GeneSwitch protein were linearized and co-tranfected into $G_{\alpha 15}$ cells. Cells were selected in 0.5 µg/ml puromycin (CAL BIOCHEM) and 100 µg/ml Zeocin (Invitrogen) at 37° C. in Dulbecco's Modified Eagle Medium supplemented with GlutaMAX, (10% dialyzed FBS, and 3 ug/ml blasticidin. Resistant colonies were expanded, and their responses to umami taste stimuli following induction with $10^{-10}$ M mifepristone determined by fluorescence microscopy following the methods of Li et al., PNAS 99(7): 4692-4696 (2002).

For automated fluorometric imaging on FLIPR instrumentation (Molecular Device), cells from one clone (designated clone I-17) were seeded into 96-well plates (approximately 80,000 cell per well) in the presence of $10^{-10}$ M mifepristone and incubated for 48 hours. Cells were then loaded with the calcium dye fluo-4-AM (Molecular Probes), 3 µM in PBS, for 1.5 hours at room temperature.

After replacement with 50 µl PBS, stimulation was performed at room temperature by the addition of 50 µl PBS supplemented with different stimuli. In contrast to previous transient T1R1/T1R3 umami receptor expression systems that necessitated quantifying T1R1/T1R3 receptor activity by individually counting responding cells (Li et al., PNAS 99(7): 4692-4696 (2002)) (because of the low activity of the receptor therein), the subject inducible expression system resulted in a clone I-17 having substantially increased activity that allowed receptor activity to be quantified by determining maximal fluorescence increases (480 nm excitation and 535 nm emission) summated over fields of imaged cells. The maximal fluorescence from four independent determinations were averaged, corrected for background fluorescence measured prior to compound addition, and normalized to the response to 0.002 mM ionomycin (CALBIOCHEM).

Figure 13:
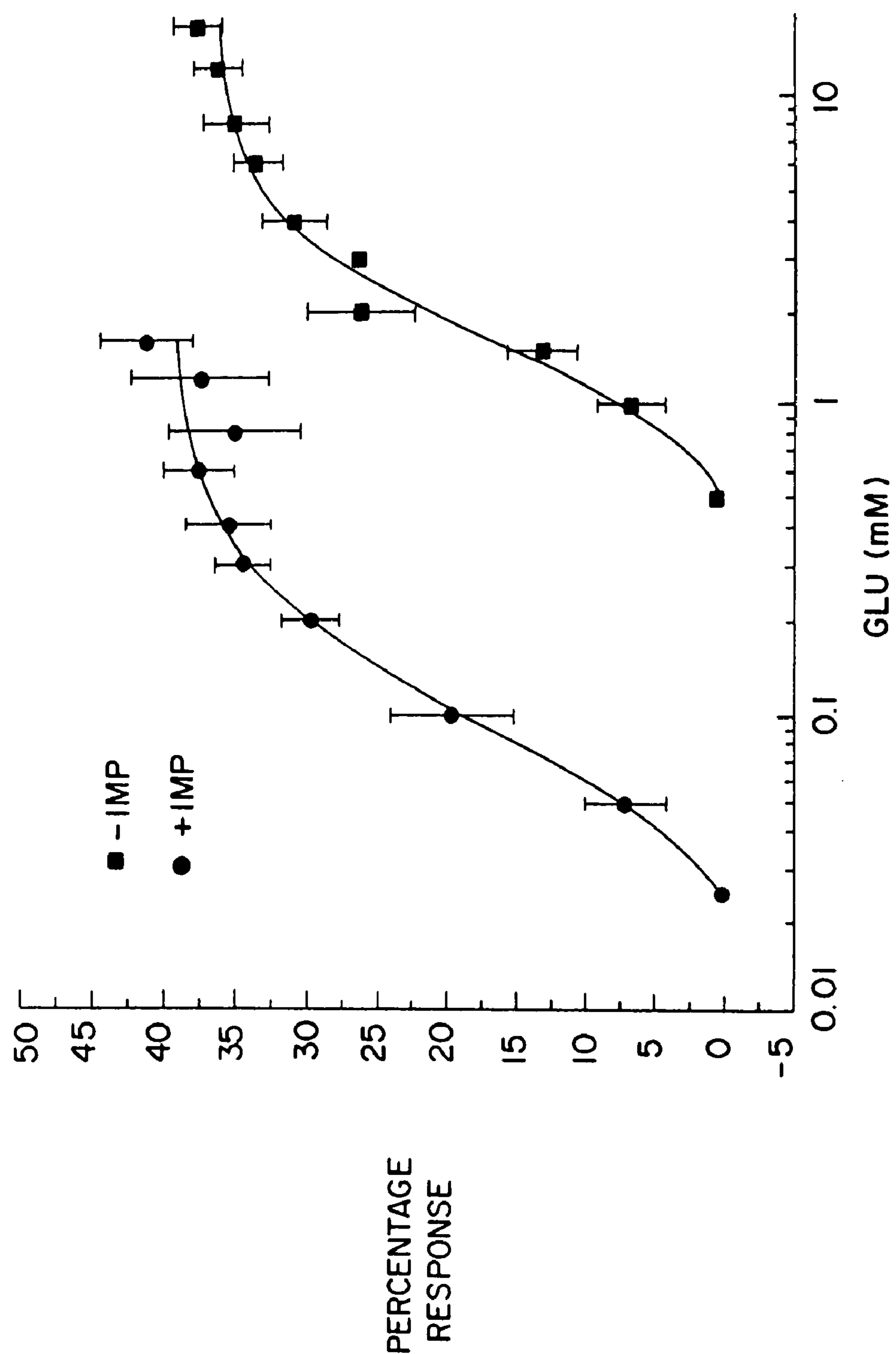
FIG. 13 shows dose-response curves determined using automated fluorescence imaging for a cell line that inducibly expresses the human T1R1/T1R3 taste receptor for L-glutamate in the presence and absence of 0.2 mM IMP.

These results are contained in FIG. 13. Particularly, FIG. 13 contains a dose-response curve determined for L-glutamate in the presence and absence of 0.2 mM IMP. In the figure, each value represents average summated maximal fluorescence (corrected for background fluorescence) for four independent determinations. These dose-response curves correspond to those determined for cells transiently transfected with T1R1/T1R3.

The selectivity of the umami T1R1/T1R3 taste receptor was also evaluated by screening with different L-amino acids. The results obtained indicated that T1R1/T1R3 is selectively activated by the umami-tasting L-amino acids (L-glutamate and L-aspartate).

Figure 14:
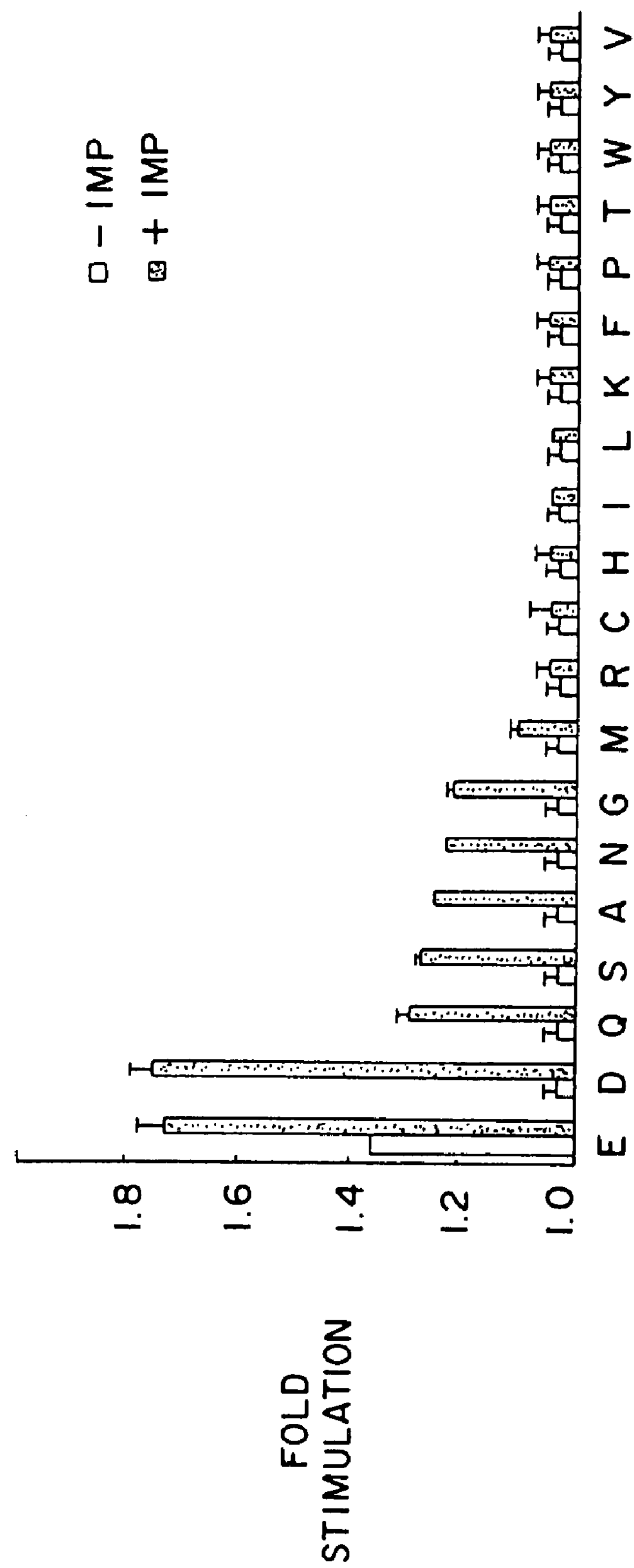
FIGS. 14 and 15 show the response of a cell line that inducibly expresses the human T1R1/T1R3 taste receptor (I-17 clone) to a panel of L-amino acids.
Figure 15:
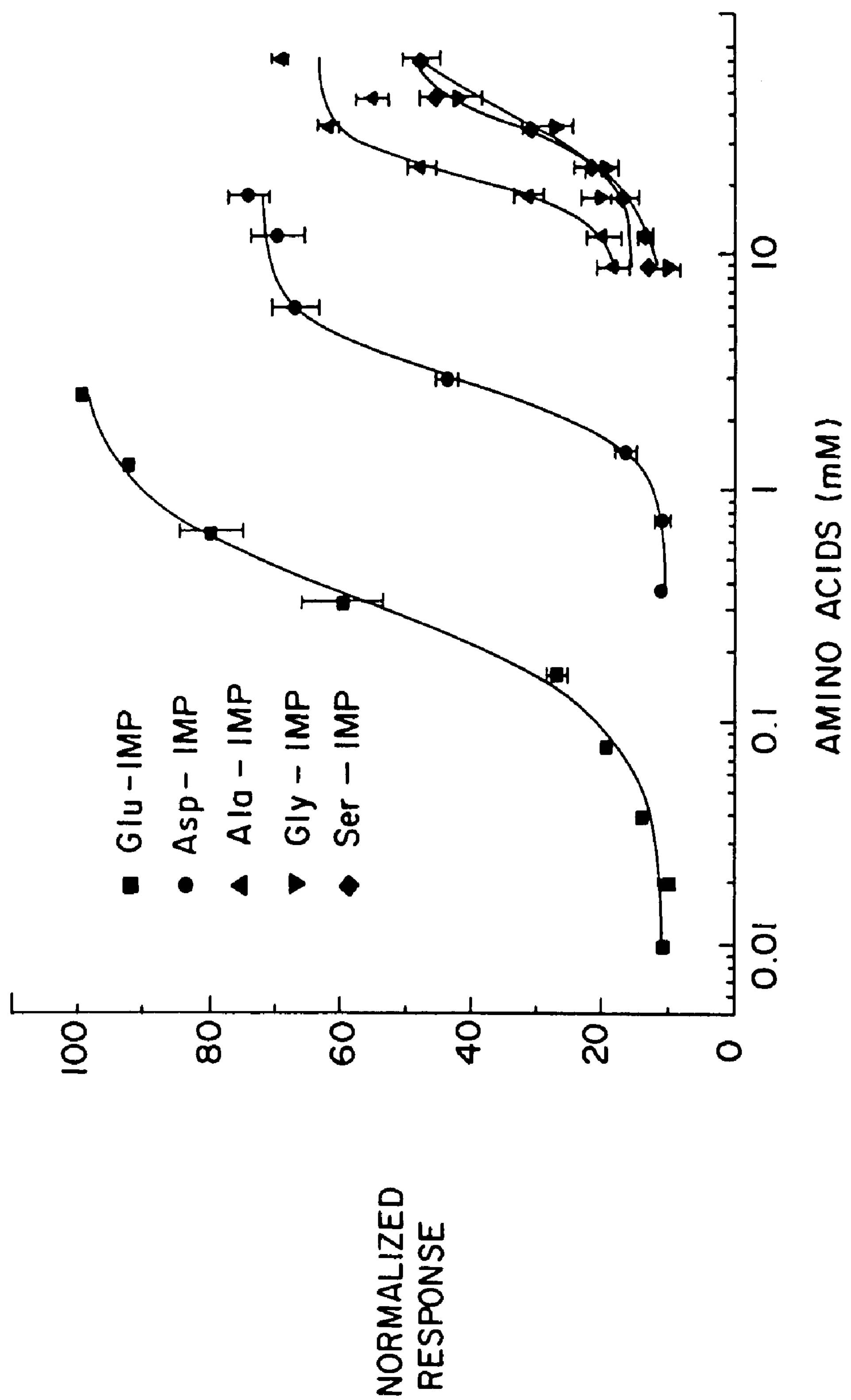

The results of experiments wherein the responses of the I-17 clone was resulted in tested in the presence of different L-amino acids are contained in FIG. 14 and FIG. 15. FIG. 14 shows the results of an experiment wherein the I-17 cell line was contacted with different L-amino acids at a concentration of 10 mM in the presence and absence of 1 mM IMP. FIG. 15 contains a dose-response curve for active amino acids determined in the presence of 0.2 mM IMP. Each value represents the average of four independent determinations.

The results obtained in these experiments support the specificity and selectivity of the umami taste receptor to umami taste stimuli. Whereas the umami taste stimuli L-glutamate and L-aspartate significantly activated the T1R1/T1R3 receptor at different concentrations (see FIGS. 14 and 15), the other L-amino acids which activated the human T1R1/T1R3 receptor only activated the receptor weakly and at much higher concentrations.

Therefore, these results support the selectivity of the T1R1/T1R3 receptor for umami taste stimuli and the suitability of this inducible stable expression system for use in high throughput screening assays using automated fluorometric imaging instrumentation to identify compounds that activate the umami taste receptor, for example L-glutamate or L-aspartate, or which enhance the activity of L-glutamate to activate the umami taste receptor, for example 5'-IMP or 5'-GMP, or block the activation of the umami taste receptor by umami taste stimuli such as L-glutamate and L-aspartate.

Compounds identified using these assays have potential application as flavorants in foods and beverage compositions for mimicing or blocking umami taste stimuli.

Example 13

Lactisole Inhibits the Receptor Activities of Human T1R2/T1R3 and T1R1/T1R3, and Sweet and Umami Taste Lactisole, an aralkyl carboxylic acid, was thought to be a selective sweet-taste inhibitor (See e.g., Lindley (1986) U.S. Pat. No. 4,567,053; and Schiffman et al. Chem Senses 24:439-447 (1999)). Responses of HEK-$G_{\alpha 15}$ cells transiently transfected with T1R2/T1R3 to 150 mM sucrose in the presence of variable concentrations of lactisole were measured. Lactisole inhibits the activity of human T1R2/T1R3 with an $IC_{50}$ of 24 μM.

The T1R1/T1R3 umami and T1R2/T1R3 sweet taste receptor may share a common subunit. It has therefore been theorized that lactisole, which inhibit the T1R2/T1R3 sweet taste receptor, may have a similar effect on the T1R1/T1R3 umami taste receptor. The present inventors tested the effect of lactisole on the response of human T1R1/T1R3 to 10 mM L-Glutamate. As with the T1R2/T1R3 sweet receptor, lactisole inhibited T1R1/T1R3 with an $IC_{50}$ of 165 μM. Lactisole inhibition likely reflects antagonism at the T1R receptors instead of, for example, non-specific inhibition of $G_{\alpha 15}$-mediated signaling because the response of muscarinic acetylcholine receptors was not inhibited by lactisole.

Figure 16B:
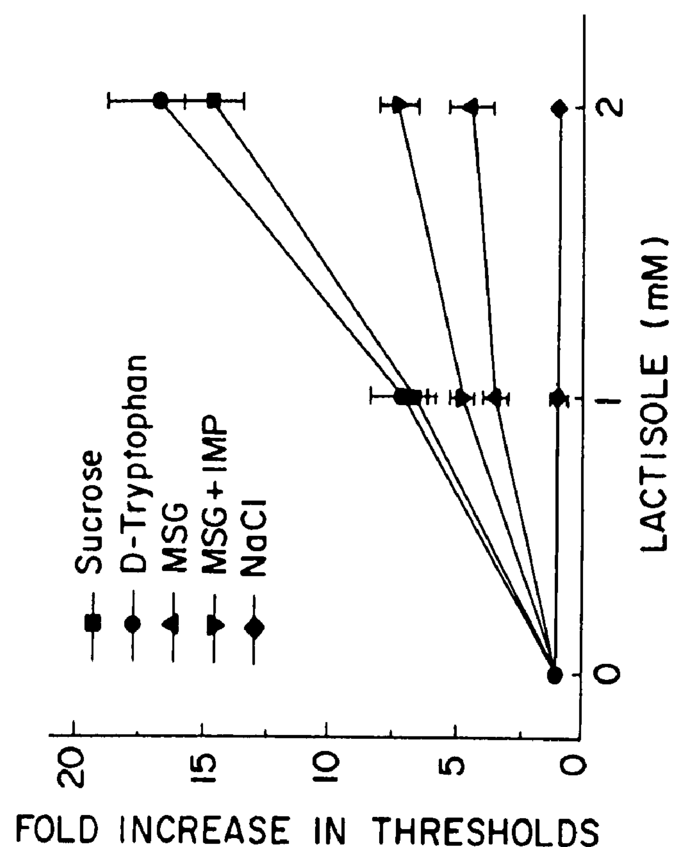
FIGS. 16*a* and 16*b* show that lactisole inhibits the receptor activities of human T1R2/T1R3 and human T1 R1/T1 R3.
Figure 16A:
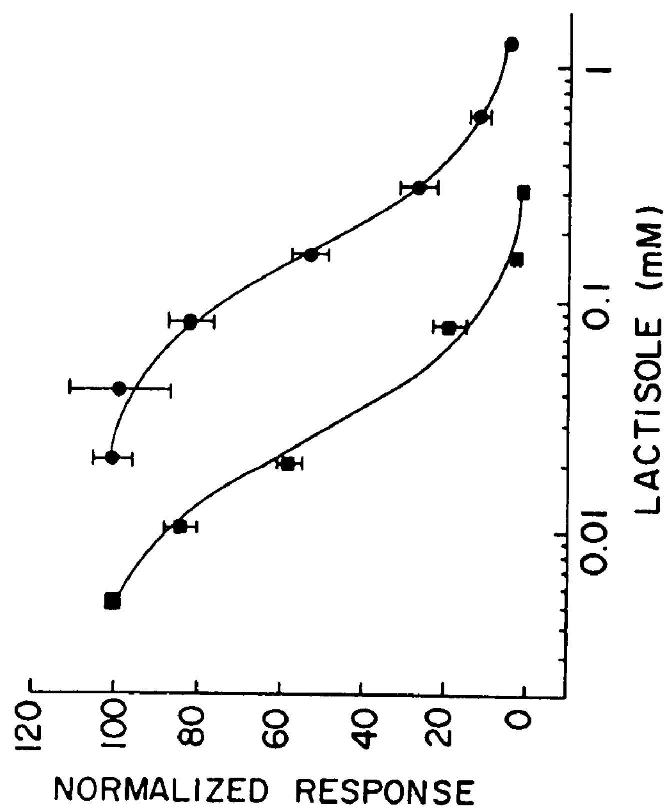

The present inventors then evaluated the effect of lactisole on human umami taste. Taste thresholds in the presence of 1 and 2 mM lactisole were determined for the umami taste stimuli L-Glutamate with or without 0.2 mM IMP, the sweet taste stimuli sucrose and D-tryptophan, and the salty taste stimulus sodium chloride following the methods of Schiffman et al. (Chem. Senses 24: 439-447 (1989)). Millimolar concentrations of lactisole dramatically increased detection thresholds for sweet and umami but not salt taste stimuli. These results are contained in FIG. 16.

In conclusion, (i) these findings further support the inventors' hypothesis that T1R1/T1R3 is the only umami taste receptor, and (ii) the T1R1/T1R3 and T1R2/T1R3 receptors may share a structurally related lactisole-binding domain.

While the foregoing detailed description has described several embodiments of the present invention, it is to be understood that the above description is illustrative only and not limiting of the disclosed invention. The invention is to be limited only by the claims which follow.

What is claimed:

1. An isolated cell that expresses a heteromeric taste receptor, wherein said receptor is comprised of at least one T1R1 polypeptide and at least one T1R3 polypeptide, wherein said T1R1 polypeptide is (i) encoded by a nucleic acid sequence comprising SEQ. ID. NO: 8, (ii) encoded by a nucleic acid sequence comprising a nucleic acid that hybridizes to SEQ. ID. NO: 8 under stringent hybridization conditions which are conducting the hybridization reaction at 42° C. in a solution comprising 50% formamide, 5×SSC, and 1% SDS and washing at 65° C. in a solution comprising 0.2×SSC and 0.1% SDS, or (iii) a T1R1 polypeptide possessing at least 95% sequence identity to the T1R1 polypeptide of SEQ. ID. NO: 5;

wherein said T1R3 polypeptide is (i) encoded by a nucleic acid sequence comprising SEQ. ID. NO: 9; (ii) encoded by a nucleic acid sequence that hybridizes to SEQ. ID. NO: 9 under stringent hybridization conditions which are conducting the hybridization reaction at 42° C. in a solution comprising 50% formamide, 5×SSC, 10% SDS; and washing at 65° C. in a solution comprising 0.2×SCC and 0.1% SDS, or (iii) a T1R3 polypeptide possessing at least 95% sequence identity to the T1R3 polypeptide of SEQ. ID. NO: 7;

and wherein said isolated cell expresses a heteromeric taste receptor that specifically binds to a ligand that specifically binds to an endogenous (wild-type) human heteromeric T1R1/T1R3 receptor comprised of at least one endogenous T1R1 polypeptide and at least one endogenous T1R3 polypeptide.

2. The cell of claim 1, wherein the T1R1 polypeptide has the polypeptide sequence of SEQ ID NO: 5 and the T1R3 polypeptide has the polypeptide sequence of SEQ ID NO: 7.

3. The cell of claim 1 wherein said T1R1 and T1R3 are of the same species.

4. The cell of claim 1, wherein said T1R1 polypeptide possesses at least 96% sequence identity to the polypeptide of SEQ. ID NO: 5.

5. The cell of claim 1, wherein said T1R3 polypeptide possesses at least 96% sequence identity to the polypeptide of SEQ. ID NO: 7.

6. The cell of claim 1, wherein said T1R1 polypeptide possesses at least 97% sequence identity to the polypeptide of SEQ ID NO: 5.

7. The cell of claim 1, wherein said T1R3 polypeptide possesses at least 97% sequence identity to the polypeptide of SEQ. ID NO: 7.

8. The cell of claim 1, wherein said T1R1polypeptide possesses at least 98% sequence identity to the polypeptide of SEQ ID NO: 5.

9. The cell of claim 1, wherein said T1R3 polypeptide possesses at least 98% sequence identity to the polypeptide of SEQ. ID NO: 7.

10. The cell of claim 1, wherein said T1R1 polypeptide possesses at least 99% sequence identity to the polypeptide of SEQ ID NO: 5.

11. The cell of claim 1, wherein said T1 R3 polypeptide possesses at least 99% sequence identity to the polypeptide of SEQ. ID NO: 7.

12. The cell of claim 1, wherein said cell is a prokaryotic cell.

13. The cell of claim 1, wherein said cell is a eukaryotic cell.

14. The cell of claim 1, wherein the cell is a CHO, HEK-293, COS, HeLa or Xenopus oocyte.

15. The cell of claim 1, wherein the cell is an endogenous taste cell.

16. The cell of claim 15, wherein the cell is a taste cell present in foliate, circumvallate or fungiform papillae.

17. The cell of claim 15, wherein the cell is a taste cell present in geschmackstreifen, oral cavity, gastrointestinal epithelium or epiglottis.

18. The cell of claim 17, wherein the cell is a taste cell present in gastrointestinal epithelium.

19. The cell of claim 1, wherein said T1R1 and T1R3 nucleic acid sequences are stably integrated into said cell.

20. The cell of claim 19, wherein T1R1 and T1R3 nucleic acid sequences comprise an extrachromosomal element.

21. The cell of claim 19, wherein T1R1 and T1R3 nucleic acid sequences are operably linked to a constitutive promoter.

22. The cell of claim 19, wherein T1R1 and T1R3 nucleic acid sequences that are operably linked to an inducible promoter.

23. The cell of claim 19, which further expresses a G protein.

24. The cell of claim 23, wherein said G protein is a promiscuous G protein, $G\alpha_{15}$, $G\alpha_{16}$, or a chimera of $G\alpha_{15}$ or $G\alpha_{16}$ with gustducin, transducin, or Gi.

25. The cell of claim 19, wherein said cell is a prokaryotic cell.

26. The cell of claim 19, wherein said cell is a eukaryotic cell.

27. The cell of claim 19, wherein the cell is a CHO, HEK-293, COS, HeLa or Xenopus oocyte.

28. The cell of claim 27 which is an HEK-293 cell line.

29. The cell of claim 28 which expresses a G protein.

30. The cell of claim 29 wherein said G protein is a promiscuous G protein.

31. The cell of claim 19, wherein receptor expression is induced by the GeneSwitch protein.

32. The cell of claim 19, wherein said T1R1 and T1R3 are of the same species.

33. The cell of claim 19 which co-expresses the nucleotide sequences of in SEQ ID NO: 8 and SEQ ID NO: 9.

* * * * *

UNITED STATES PATENT AND TRADEMARK OFFICE

CERTIFICATE OF CORRECTION

PATENT NO. : 7,368,285 B2
APPLICATION NO. : 10/179373
DATED : May 6, 2008
INVENTOR(S) : Mark Zoller et al.

It is certified that error appears in the above-identified patent and that said Letters Patent is hereby corrected as shown below:

In the claims

Column 119, Claim 1, lines 29-30 please change “10% SDS” to --1% SDS--.

Signed and Sealed this
Twelfth Day of July, 2011

David J. Kappos
*Director of the United States Patent and Trademark Office*